US011730806B2

(12) United States Patent
Starks et al.

(10) Patent No.: US 11,730,806 B2
(45) Date of Patent: Aug. 22, 2023

(54) METHODS OF MANUFACTURING AN IMMUNOGENIC COMPOSITION COMPRISING A RECOMBINANT PROTEIN

(71) Applicant: Boehringer Ingelheim Vetmedica GmbH, Ingelheim am Rhein (DE)

(72) Inventors: Andrea J. Headrick Starks, Agency, MO (US); Fuad Tawfiq Haddadin, St. Joseph, MO (US); Gregory Brian Haiwick, Ankeny, IA (US); Merrill Lynn Schaeffer, St. Joseph, MO (US); Curtis Robert Edwards, Gower, MO (US)

( * ) Notice: Subject to any disclaimer, the term of this patent is extended or adjusted under 35 U.S.C. 154(b) by 240 days.

(21) Appl. No.: 16/879,471

(22) Filed: May 20, 2020

(65) Prior Publication Data

US 2020/0345834 A1    Nov. 5, 2020

Related U.S. Application Data

(62) Division of application No. 15/801,754, filed on Nov. 2, 2017, now Pat. No. 10,660,952.

(30) Foreign Application Priority Data

Nov. 3, 2016  (EP) ..................... 16197089

(51) Int. Cl.
| | | |
|---|---|---|
| *A61K 39/23* | (2006.01) | |
| *A61P 31/20* | (2006.01) | |
| *A61P 31/14* | (2006.01) | |
| *A61K 39/12* | (2006.01) | |
| *A61K 39/00* | (2006.01) | |

(52) U.S. Cl.
CPC ............ *A61K 39/23* (2013.01); *A61K 39/12* (2013.01); *A61P 31/14* (2018.01); *A61P 31/20* (2018.01); *A61K 2039/5252* (2013.01); *A61K 2039/5254* (2013.01); *A61K 2039/552* (2013.01); *A61K 2039/70* (2013.01); *C12N 2750/14322* (2013.01); *C12N 2770/10034* (2013.01)

(58) Field of Classification Search
None
See application file for complete search history.

(56) References Cited

U.S. PATENT DOCUMENTS

| | | | |
|---|---|---|---|
| 5,498,413 A | 3/1996 | Casal Alvarez et al. | |
| 5,925,359 A | 7/1999 | Van Woensel et al. | |
| 6,001,370 A | 12/1999 | Burch et al. | |
| 6,015,663 A | 1/2000 | Wesley et al. | |
| 6,042,830 A | 3/2000 | Chladek et al. | |
| 6,110,467 A | 8/2000 | Paul et al. | |
| 6,217,883 B1 | 4/2001 | Allan et al. | |
| 7,700,285 B1 | 4/2010 | Eichmeyer et al. | |
| 9,561,270 B2* | 2/2017 | Kohler ................ A61K 39/12 |
| 2002/0058021 A1 | 5/2002 | Audonnet et al. | |
| 2011/0059126 A1* | 3/2011 | Kohler ................ A61K 39/12 |
| | | | 424/202.1 |
| 2011/0150770 A1 | 6/2011 | Bautista et al. | |
| 2012/0164170 A1 | 6/2012 | Kuo et al. | |
| 2014/0170180 A1 | 6/2014 | Iyer et al. | |
| 2014/0234354 A1 | 8/2014 | Iyer et al. | |
| 2014/0322267 A1 | 10/2014 | Haiwick et al. | |
| 2015/0246113 A1 | 9/2015 | Iyer et al. | |
| 2015/0283229 A1 | 10/2015 | Hernandez et al. | |
| 2015/0283230 A1 | 10/2015 | Iyer et al. | |
| 2018/0133309 A1 | 5/2018 | Bucklin et al. | |
| 2018/0147278 A1 | 5/2018 | Klocke et al. | |
| 2020/0345834 A1* | 11/2020 | Starks ................ A61P 31/14 |

FOREIGN PATENT DOCUMENTS

| | | |
|---|---|---|
| CL | 2019001049 A1 | 8/2019 |
| CN | 102488895 A | 6/2012 |
| CN | 102727881 A | 10/2012 |
| CN | 104288760 A | 1/2015 |
| EP | 0117767 A1 | 9/1984 |
| EP | 0551449 A1 | 7/1993 |
| EP | 2460818 A2 | 6/2012 |
| JP | 2013503893 A | 2/2013 |
| RU | 2004108484 A | 9/2005 |
| WO | 198802026 A1 | 3/1988 |
| WO | 2011028888 A2 | 3/2011 |
| WO | 2011107534 A1 | 9/2011 |
| WO | 2013024113 A1 | 2/2013 |
| WO | 2014099669 A1 | 6/2014 |
| WO | 2014127084 A1 | 8/2014 |
| WO | 2018083154 A1 | 5/2018 |
| WO | 2018083156 A1 | 5/2018 |

OTHER PUBLICATIONS

Geneseq db 2003 access No. AAR29079 alignment with SEQ ID No. 2.*
PIR_80 db 1993 access No. A60006 alignment with SEQ ID No. 2.*
Geneseq db 2013 access No. BAJ21009 alignment with SEQ ID No. 2.*
Sequence alignment of SEQ ID No. 2 with UniProt database accession No. Q32Z58 9VIRU by Streck et al 2011.*
Zhou H. et al., Production and purification of VP2 protein of porcine parvovirus expressed in an insect-baculovirus c

(56) References Cited

OTHER PUBLICATIONS

Cui et al., "Genome Sequence of Chinese Porcine Parvovirus Strain PPV2010". Journal of Virology, vol. 86, No. 4, 2012, p. 2379.
Database UniProt Accession No. K4K2G7, Jan. 9, 2013, Retrieved from EBI accession No. Uniprot: K4K2G7, pp. 1-3.
Database UniProt Accession No. K4K4H5, Jan. 9, 2013, Retrieved from EBI accession No. Uniprot: K4K4H5, pp. 1-3.
Database UniProt Accession No. Q32Z58, Dec. 6, 2005, Retrieved from EBI accession No. Uniprot: Q32Z58, pp. 1-3.
GenBank Accession No. JX896318, Xiao et al., "Identification of a new porcine parvovirus: an evidence for the coexistence of different intermediates during the evolution of parvovirus". College of Veterinary Medicine, Iowa State University, Department of Veterinary Diagnostic and Production Animal Medicine, Oct. 2012, pp. 1-4.
GenBank Accession No. JX896320.1, Xiao et al., "Complete Genome Sequence of a Novel Porcine Parvovirus (PPV) Provisionally Designated PPV5". Genome Announcement, vol. 1, No. 1, E00021-12, 2012, pp. 1-3.
GenBank Accession No. JX896321.1, Xiao et al., "Porcine parvovirus 5 isolate IA469 clone 1, complete genome". College of Veterinary Medicine, Iowa State University, Department of Veterinary Diagnostic and Production Animal Medicine, 2013, pp. 1-3.
GenBank Accession No. AFM73871.1 Cadar et al., "Comparative genetic characterization, phylogeography and evolution of novel porcine parvoviruses.". Direct Submission, Mar. 31, 2012, Jun. 26, 2012, 1 page.
Martinez et al., "Production of porcine parvovirus empty capsids with high immunogenic activity". Vaccine, vol. 10, No. 10, 1992, pp. 684-690.
Mengeling et al., "The effect of porcine parvovirus and porcine reproductive and respiratory syndrome virus on porcine reproductive performance." Animal Reproduction Science, vol. 60-61, 2000, pp. 199-210.
Preuss et al., "Comparison of Two Different Methods for Inactivation of Viruses in Serum." Clinical and Diagnostic Laboratory Immunology, vol. 4, No. 5, Sep. 1997, pp. 504-508.
Puig et al., "Vaccination with the Mixed Administration of ERYSENG@ Parvo and Unistrain@ PRRS in Gilts Clinically Protects Against a Heterologous PRRSV Infection". European Symposium of Porcine Health Management, 2015, 1 page. [Accessed at: https://www.hipra.com/portal/en/hipra/knowledge/pubdetail/Vaccination-with-the-mixed-administration-of-ERYSENG-Parvo-and-UNISTRAIN-PRRS-in-gilts-clinically-protects-against-a-heterologous-PRRSV-Infection; Retrieved on Mar. 7, 2017].
Streck et al., "High rate of viral evolution in the capsid protein of porcine parvovirus." Journal of General Virology, vol. 92, No. 11, 2011, pp. 2628-2636.
Xu et al., "Induction of Immune Responses in Mice after Intragastric Administration of Lactobacillus casei Producting Porcine Parvovirus VP2 Protein." Applied and Environmental Microbiology, vol. 73, No. 21, Nov. 2007, pp. 7041-7047.
Zeeuw et al., "Study of the virulence and cross-neutralization capability of recent porcine parvovirus field isolates and vaccine viruses in experimentally infected pregnant gilts." Journal of General Virology, vol. 88, 2007, pp420-427.
Rose et al., Preventative Veterinary Medicine, vol. 61, 2003, pp. 209-225.
Ranz et al., Journal of General Virology, vol. 70, 1989, pp. 2541-2553.
Dokland, Virus Research, vol. 154, 2010, pp. 86-97.
Sequence alignment of Seq Id No. 1 with UniProt database accession No. Q32Z58_9VIRU by Streck et al. 2011.
Sequence alignment of Seq Id No. 10 with UniProt database accession No. Q32Z58_9VIRU by Streck et al. 2011.
Opriessnig et al., Clinical and Vaccine Immunology, vol. 18, No. 8, pp. 1261-1268.
Geneseq db 2013 access No. AAR29079 alignment with Seq ID No. 2.
Javier Lopez-Vidal, "Improved production efficiency of virus-like particles by the baculovirus expression vector system", PLoS One, Oct. 12, 2015, pp. 1-13.
International Search Report and Written Opinion for PCT/EP2017/078020 dated Mar. 29, 2018.
Antonis et al., Vaccine, 2006, pp. 5481-5490.
Daniel Cadar et al., "Phylogeny and evolutionary genetics of porcine parvovirus in wild boars", Infection, Genetics and Evolution, vol. 12, No. 6, Aug. 1, 2012, pp. 1163-1171.
Han et al., Journal of Comparative Pathology, 2014, 150 (2-3), pp. 297-305.

\* cited by examiner

|                    | D28  | D31  | D35  | D38  | D42  | D49  |
|--------------------|------|------|------|------|------|------|
| ReproCyc PRRS+PPV  | 0.00 | 3.45 | 1.00 | 1.62 | 0.25 | 0.50 |
| ReproCyc PRRS      | 0.00 | 3.61 | 1.36 | 2.25 | 1.00 | 0.50 |
| Control            | 0.00 | 3.74 | 4.77 | 3.33 | 0.75 | 1.51 |

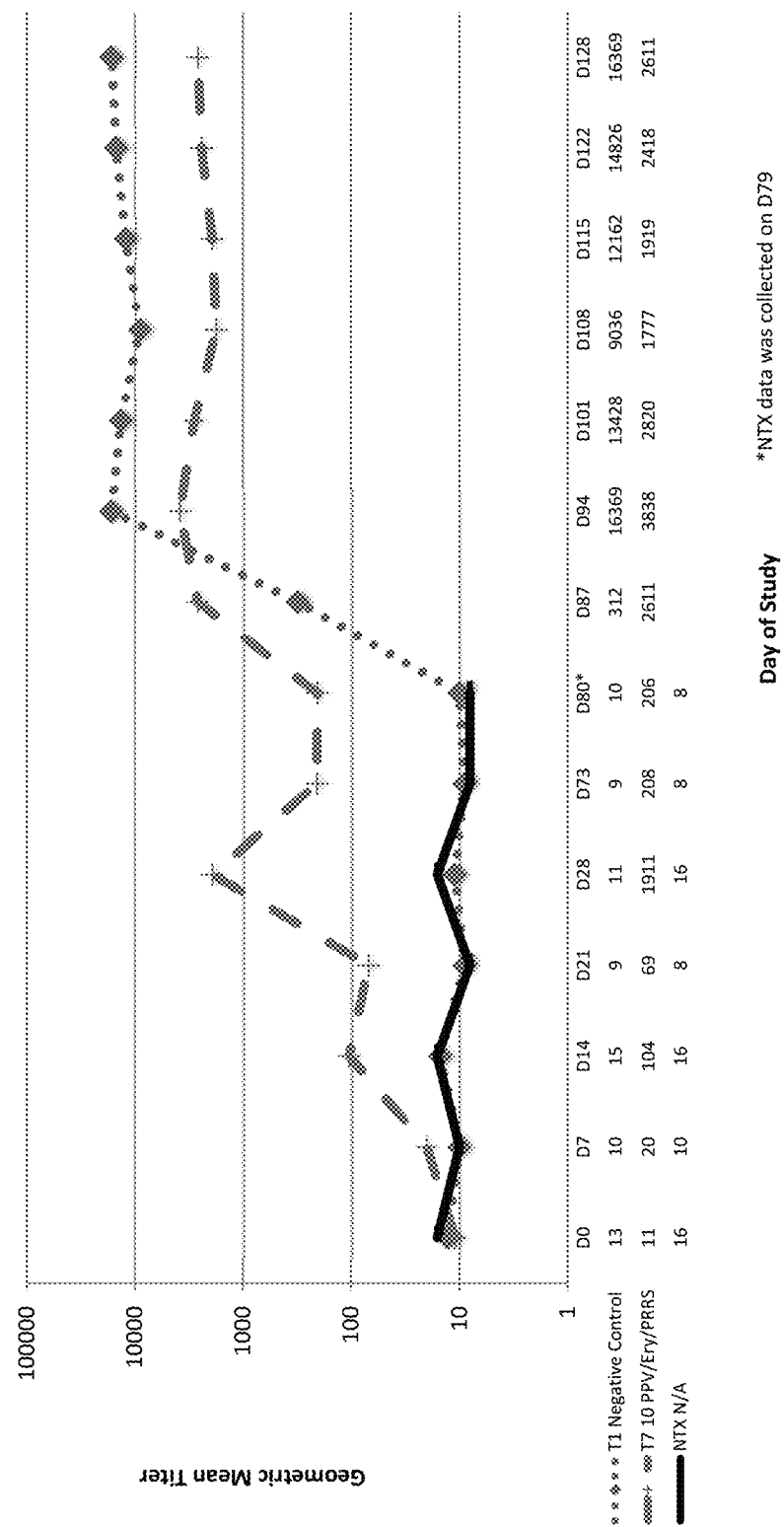

METHODS OF MANUFACTURING AN IMMUNOGENIC COMPOSITION COMPRISING A RECOMBINANT PROTEIN

SEQUENCE LISTING

This application contains a sequence listing in accordance with 37 C.F.R. 1.821-1.825. The sequence listing accompanying this application is hereby incorporated by reference in its entirety.

CROSS-REFERENCE TO RELATED APPLICATIONS

This application claims priority to U.S. patent application Ser. No. 15/801,754 filed on Nov. 2, 2017; which claims priority to E.P. application 16197089.2 filed on Nov. 3, 2016, each of which is incorporated by reference herein, in their entirety.

INCORPORATION BY REFERENCE

All references cited herein, are incorporated by reference herein, in their entirety.

BACKGROUND OF THE INVENTION

A. Field of the Invention

In a first consideration, the present invention relates to a porcine parvovirus and porcine reproductive and respiratory syndrome virus vaccine specific to the isolates which are capable of reducing clinical signs of disease caused by porcine parvovirus and/or porcine reproductive and respiratory syndrome virus. In a second consideration, the present invention further relates to methods of producing immunogenic compositions as well as such immunogenic compositions exhibiting reduced virucidal activity.

B. Description of the Related Art

Porcine reproductive and respiratory syndrome virus (PRRSV) is a member of the virus family Arteriviridae and belongs, together with the Coronaviridae, to the virus order Nidovirales. PRRSV is an enveloped virus with a single-stranded, positive-sense RNA genome of about 15 kilobases comprising nine open reading frames (ORFs), namely ORF1a, ORF1ab, ORF2a, ORF 2ab, and ORFs 3 through ORF7. ORFs 1a and 1ab encode large polyproteins that are processed into the viral nonstructural proteins (nsp) by auto- and trans-cleavages of viral proteases nsp1, nsp2, and nsp4 (Snijder and Meulenberg, 1998). ORF4 encodes a minor glycoprotein (GP4) which is, next to a major glycoprotein (GP5) and two other minor glycoproteins (GP2a and GP3), found in the viral envelope, wherein all of said glycoproteins are important for infectious virus production.

PRRSV is considered one of the economically most important infectious agents in pigs causing late-term reproductive failure in sows and respiratory disease in growing pigs. Often, PRRSV infection is complicated by secondary bacterial infections being attributed to the immunosuppressive nature of the virus. Also, PRRSV viremia lasts for weeks, and virus then still can be detected in lymphoid organs for several months, demonstrating difficulties or failure of the host's immune response to clear the virus (Allende et al., 2000).

There are two distinct viral PRRSV genotypes causing similar clinical symptoms that diverge by about 40% on nucleotide sequence level, genotype I (EU) and genotype II (US). The North American (US) prototype strain is VR-2332, while the European (EU) prototype strain is Lelystad virus.

Porcine parvovirus is an autonomous replicating virus of the Parvovirinae subfamily of the genus Protoparvovirus within the family Parvoviridae containing a single stranded DNA molecule of about 5100 nucleotides (Cotmore et al., 2014: Arch Virol.: 159(5): 1239-1247; Molitor et al., 1984: Virology: 137(2):241-54.). Only the minus strand of the DNA is packaged into virions. The genome of the virus encodes three capsid proteins (VP1, VP2, VP3) and one non-structural protein (NS1). The capsid of parvovirus is about 22-25 nanometers in diameter and is comprised of VP1 and VP2 subunits. These proteins are derived from alternatively spliced versions of the same RNA molecule and thus overlap in sequence. Further, porcine parvovirus exhibits a high level of sequence similarity to feline pan-leukopenia virus, canine parvoviruses and rodent parvovirus (Ranz et al., 1989: J. gen. Virol: 70:2541-2553).

Although there are differences in porcine parvovirus strains, some being extremely pathogenic and others being less pathogenic or totally non-pathogenic, when the virus becomes established or endemic in a country, the pathogenic strains appear to circulate in the population.

Porcine parvovirus (PPV) infection is a common cause of reproductive failure in breeding pigs throughout the world. Serological studies show that porcine parvovirus is widespread in all swine producing regions of the world with up to 80% of animals showing seroconversion.

The Porcine Parvovirus (PPV) causes reproductive failure in swine, resulting in death and fetal mummification, still births and other reproductive failures in pregnant sows. (Joo & Johnson. 1976. Veterinary Bulletin 46, 653-660; Mengling. 1978. J. Am. Vet. Med. Assoc. 172, 1291-1294).

The PPV induces reproductive failure when susceptible (non-immune) gilts and sows are infected during pregnancy. This is the only time the virus causes disease. Infection in the pig occurs following ingestion or inhalation of the virus. The PPV then circulates in the bloodstream and in the pregnant pig crosses the placenta and infects the developing embryos and fetuses. Following natural infection, active immunity develops that probably lasts for the life of the pig. If active immunity occurs before pregnancy then the developing piglets are not affected. At birth the piglets receive maternal immunity in the colostrum from the sow and this maternal immunity lasts for up to 20 weeks of age. The greater the level of active immunity in the sow, the more maternal immunity that she passes onto her piglets. Thereafter, natural infection with PPV can occur.

The disease caused by PPV in pigs is often referred to as a SMEDI (an acronym of stillbirth, mummification, embryonic death, and infertility). If infection occurs at days 0-30 of pregnancy, embryonic mortality can occur resulting in decreased litter size. The most obvious feature following infection at 30-70 days of pregnancy is the birth of mummified piglets. Mummification is the process of sterile digestion of the tissues of the piglets that die in the uterus after the skeleton has started to solidify. PPV infection is also associated with stillbirths and weak born pigs if infection occurs in the later stages of pregnancy. Abortion can also be the result of PPV infection, but is not a common clinical sign of this disease. Overall, PPV infection decreases the number of pigs born per sow per year.

Currently available PPV vaccines are produced by growing native virus on primary cells of porcine origin or in established cell lines. After this, infectious virus is isolated and inactivated with chemical agents to end up with a whole cell killed virus vaccine. However, such processes of growing native infectious virus are problematic for biosecurity and safety considerations.

Subunit vaccines based on recombinant proteins can suffer from poor immunogenicity owing to incorrect folding of the target protein or poor presentation to the immune system. Further, whole cell killed vaccines present all antigens of the native virus, whereas in a subunit vaccine there is a limitation to a specific amino acid sequence.

Recombinant PPV vaccines have already been described in the prior art. However, until now only whole cell killed vaccines are commercially available. Thus, it seems that so far no appropriate recombinant PPV subunit vaccines have been developed and shown to be effective and safe. The recombinant PPV subunit vaccines described so far have not been tested in controlled, laboratory challenge experiments. The recombinant PPV subunit vaccines that have been evaluated, have not worked as well as whole cell killed PPV vaccines or the recombinant PPV subunit vaccines have not been safe (shown adverse reactions).

Field isolates of PPV have been identified that differ genetically and antigenically from the vaccine strains. PPV Genotype 2 virus, PPV-27a, is highly virulent in pregnant gilts after experimental infection, as demonstrated by the high mortality among the fetuses of sows infected with PPV-27a (85%) compared with sows infected with the other strains of PPV, e.g. PPV-NADL-2. However, the currently available commercial vaccines against PPV are based on inactivated whole-virus preparations of PPV genotype 1 strains isolated some 30 years ago (Jozwik et al 2009; Journal of General Virology; 90; 2437-2441).

Further art is as follows:

Adriaan F. G. Antonis. "A novel recombinant virus-like particle vaccine for prevention of porcine parvovirus-induced reproductive failure" Vaccine 24 (2006) 5481-5490.

Chen Y. Guo W. "A novel recombinant pseudorabies virus expressing parvovirus VP2 gene: Immunogenicity and protective efficacy in swine" Virology Journal 2011, 8:307.

Merenga et al. "Large scale production and downstream processing of a recombinant porcine parvovirus vaccine" Appl Microbiol Biotechnol. 2002 June; 59(1):45-50. Epub 2002 Apr. 16.

A. Jozwik, J. Manteufel, H.-J. Selbitz and U. Truyen. Vaccination against porcine parvovirus protects against disease, but does not prevent infection and virus shedding after challenge infection with a heterologous virus strain. Journal of General Virology (2009), 90, 2437-2441.

Chinese patent application CN 102 488 895 A discloses a triplex virus-like particle vaccine consisting of porcine circovirus, porcine parvovirus and PRRSV. This triple VLP vaccine contains PCV-2 major structural protein CAP protein, PPV VP2 protein epitope and PRRSV GP5 protein epitope.

Russian patent application RU 2004108484 A discloses an inactivated vaccine against PRRSV and PPV. This inactivated vaccine contains antigenic material from PRRS virus strain, reproduced in passaged cell culture Marc-145 and inactivated with aminoethylethyleneimine (AEEI) and antigenic material from PPV strain reproduced in passaged YPK cell culture and inactivated with AEEI.

Chinese patent application CN 104 288 760 A discloses a vaccine composition comprising an immune amount of a porcine circovirus type 2 antigen, an immune amount of a PRRSV antigen and a PPV antigen.

Chinese patent application CN 102 727 881 A discloses a highly pathogenic PRRS JXAI-R strain and PPV bigeminal live vaccine.

Puig et al. (info.hipra.com/DOCS/UNISTRAIN/PUBLICATIONS/ESPHM-2015/1-Clinical-protection.pdf) relate to vaccination of the mixed administration of the inactivated ERYSENG Parvo and inactivated UNISTRAIN PRRS vaccines manufactured by Hipra.

Zeew E J L et al. (Journal of General Virology 2007, 88(2): 420-427) describes a study of the virulence and cross-neutralization capability of recent parvovirus field isolates and vaccine viruses in experimentally infected pregnant gilts.

US patent application US 2014/0322267 A1 relates to ORF2 protein of PCV2 subtype A (PCV2A) for use in cross-protection.

EP patent application EP 2 460 818 A2 relates to PCV2 immunogenic compositions and methods of producing such compositions.

U.S. Pat. No. 7,700,285 B1 relates to PCV2 immunogenic compositions and methods of producing such compositions.

PCT patent application WO 2013/024113 relates to influenza H5 vaccines.

US patent application US 2015/0283229 A1 relates to porcine epidemic diarrhea virus vaccine.

Disadvantages of the art are, for instance, (i) concerns that the PPV component in a conventional killed vaccine is not completely inactivated (which would then introduce live PPV into a herd); (ii) lack of cross-protection against heterologous strains of PPV; lack of vaccination scheme that protects breeding age gilts and sows and fetuses from PPV and PRRSV associated reproductive disease.

There is a need for new combination and/or associated use vaccines of PRRSV and PPV that can be successfully employed against infections with PRRSV and/or PPV. There is also a need for novel methods of reducing the virucidal activity of compositions that would normally exhibit some degree of virucidal activity; as well as for immunogenic compositions with reduced or no virucidal activity.

SUMMARY OF THE INVENTION

The solution to the above technical problem(s) is achieved by the description and the embodiments characterized in the claims and clauses disclosed herein.

Thus, the invention in its different aspects is implemented according to the claims and clauses disclosed herein.

First Consideration of the Present Invention

In a first consideration the present invention relates to an immunogenic composition or a combination vaccine or a combination comprising:
  a) at least one porcine parvo virus (PPV) antigen, wherein the at least one PPV antigen is any antigen contained in PPV, and
  b) at least one porcine reproductive and respiratory syndrome (PRRS) virus antigen, wherein the at least one PRRS virus antigen is any antigen contained in PRRS virus.

The present invention further relates to a kit comprising the immunogenic composition or combination vaccine or combination as herein described and/or claimed.

The present invention further relates to the use of the immunogenic composition or combination vaccine or combination as herein described and/or claimed or the kit as herein described and/or claimed for the preparation of a medicament, preferably of a vaccine.

Advantageously, the experimental data provided by the present invention disclose that the PPV VP2 subunit vaccine component of the present invention is safe and efficacious in preventing viremia and PPV infection in fetuses. Further, the experimental data provided by the present invention disclose that the PPV VP2 subunit vaccine component of the present invention has a broad protection spectrum as the vaccine protects against heterologous North American as well as heterologous European challenge strains.

Advantageously, the experimental data provided by the present invention disclose that the PPV VP2 subunit vaccine component of the present invention is as efficacious as the whole killed virus. Extensive inactivation processes (which are necessary for inactivating native PPV when generating whole killed virus vaccines) could be avoided by utilizing a recombinant subunit vaccine comprised of PPV VP2.

Further advantages of the underlying invention are, for instance, (i) reduction of the number of vaccine injections administered to animals, thus increasing animal welfare reducing the stress for the animals; (ii) reduction of manpower; (iii) same efficacy as a single administration; (iv) vaccine timing as both components address reproductive disease in pregnant swine; (v) prevention of PPV viremia in vaccinated gilts post-challenge with a heterologous PPV strain; (vi) reduction in the number of stillbirths and mummified piglets in the vaccinated groups after PPV challenge; (vii) increase in the total number of fetuses in the PPV vaccinated sows; (viii) 100% of PPV vaccinated piglets are protected after PPV challenge; (ix) duration of immunity (DOI): 6 months; (x) both REPROCYC® PRRS EU and mixed REPROCYC® PRRS EU+PPV VP2 were efficacious based on reduction of viral load and proportion viremic post-challenge; (xi) lack of interference with efficacy against PRRSV vaccination was demonstrated; (xii) four-week onset of immunity can be established for REPROCYC® PRRS EU; (xiii) a combination vaccine (PPV VP2 10 µg+Ery) with INGELVAC® PRRS MLV was demonstrated to be efficacious in preventing viremia and PPV infection of fetuses at day 40 after gestation (40 dG).

Second Consideration of the Present Invention

In a second consideration the present invention relates to a method of producing an immunogenic composition comprising a recombinant protein, wherein the method comprises the steps in the following order:
(i) providing/obtaining a mixture comprising:
   a first liquid,
   recombinant protein and/or quaternary structures composed of a plurality of said recombinant protein, and
   a vector comprising a nucleic acid sequence encoding said recombinant protein;
(ii) adding a second liquid to the mixture of step (i), wherein the second liquid is different from the first liquid;
(iii) washing, and optionally finally concentrating, the recombinant protein and/or quaternary structures composed of a plurality of said recombinant protein in the mixture by further adding additional second liquid to the mixture resulting from step (ii) and removing a portion of the first and/or second liquid from such combined mixture;
(iv) inactivating the vector by adding an inactivating agent to the mixture resulting from step (iii);
(v) neutralizing the inactivating agent by adding a neutralizing agent to the mixture resulting from step (iv).

The present invention further relates to the method as herein described and/or claimed, wherein the mixture of step (i) supra is obtainable by a procedure comprising the steps of:
(a) permitting infection of susceptible cells in culture with a vector comprising a nucleic acid sequence encoding said recombinant protein and/or quaternary structures composed of a plurality of said recombinant protein, wherein said recombinant protein and/or quaternary structures composed of a plurality of said recombinant protein is expressed by said vector,
(b) thereafter recovering the recombinant protein and/or quaternary structures composed of a plurality of said recombinant protein from the cell culture, wherein preferably cell debris is separated from the recombinant protein and/or quaternary structures composed of a plurality of said recombinant protein via a separation step, preferably including a micro filtration through at least one filter, more preferably two filters, wherein the at least one filter preferably has a pore size larger than the recombinant protein and/or quaternary structures composed of a plurality of said recombinant protein, in particular has a pore size of about 0.1 µm to about 4 µm.

As for PPV antigen preparations, when the Baculovirus inactivation at 37° C. was performed after clarification and before diafiltration a heavy degree of precipitation (aggregation) was observed. This aggregation, although not related to the PPV antigen, is thought to interfere with inactivation kinetics and virucidal testing. Preliminary data suggest that a diafiltration process after culture clarification and before Baculovirus inactivation considerably reduces the degree of aggregation in the PPV virus-like-particles (VLP) harvest during the inactivation process. Data show that the degree of aggregation is intensified at higher temperature (37° C.), and minimized at lower temperatures (27° C. or 4° C.) over time: a diafiltration process before Baculovirus inactivation at 37° C. additionally eliminates the virucidal activity of the inactivant's neutralization agent sodium thiosulfate and ExCell 420 media reaction. The validated process confirms that an inactivated Baculovirus expressed PPV VLP product has been consistently non-virucidal to PRRSV vaccine. Such PPV VLP vaccine possesses in particular an advantageous long term stability after mixing with PRRSV based on the missing virucidal effect thereby rendering it possible to mix both PPV and PRRSV components freshly before administration and/or to commercialize a ready-to-use administration form (e.g., combination vaccine or kit).

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 3 shows the geometric mean PPV HI titers by Group and Day.

DETAILED DESCRIPTION

Figure 1:
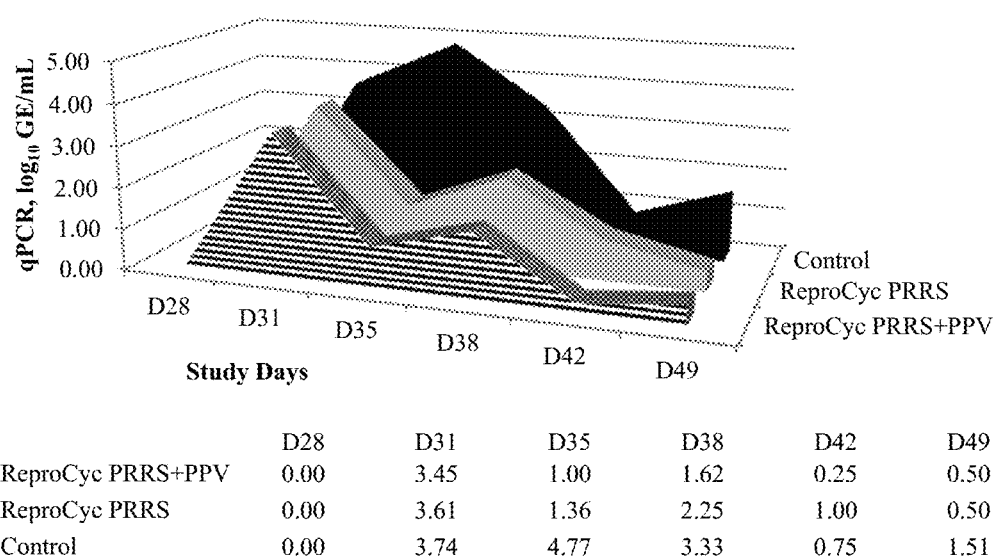
FIG. 1 shows PRRSV Viremia (qPCR, log 10 GE/mL) by Group and Day.

Before the aspects of the present invention are described, it must be noted that as used herein and in the appended claims, the singular forms "a", "an", and "the" include plural reference unless the context clearly dictates otherwise. Thus, for example, reference to "an antigen" includes a plurality of antigens; reference to the "virus" is a reference to one or more viruses and equivalents thereof known to those skilled in the art, and so forth. Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies as reported in the publications which might be used in connection with the invention. Nothing herein is to be construed as an admission that the invention is not entitled to antedate such disclosure by virtue of prior invention.

First Consideration of the Present Invention

In one aspect, the present invention concerns an immunogenic composition or a combination vaccine or a combination comprising
(a) at least one porcine parvo virus (PPV) antigen, wherein the at least one PPV antigen is any antigen contained in PPV, and
(b) at least one porcine reproductive and respiratory syndrome (PRRS) virus antigen, wherein the at least one PRRS virus antigen is any antigen contained in PRRS virus.

The term "porcine parvovirus" or "PPV" is well known to the person skilled in the art. However, "porcine parvovirus" is an autonomous replicating virus of the genus parvovirus within the family Parvoviridae containing a single stranded DNA molecule. The genome of the virus encodes three capsid proteins (VP1, VP2, VP3) and one non-structural protein (NS1). The disease caused by PPV in pigs is often referred to as a SMEDI (an acronym of stillbirth, mummification, embryonic death, and infertility). The term "Porcine parvovirus" in the scope of the present invention encompasses all strains, genotypes and serotypes of the porcine parvovirus as well as of the parvovirinae subfamily of the genus Protoparvovirus within the family Parvoviridae.

The terms "porcine reproductive and respiratory syndrome virus" or "PRRS virus" or "PRRSV" is well known to the person skilled in the art. "Porcine reproductive and respiratory syndrome virus" is a member of the virus family Arteriviridae, belongs together with the Coronaviridae to the virus order Nidovirales, and is an enveloped virus with a single-stranded, positive-sense RNA genome of about 15 kilobases comprising nine open reading frames (ORFs), namely ORF1a, ORF1ab, ORF2a, ORF 2ab, and ORFs 3 through ORF7. ORFs 1a and 1ab encode large polyproteins that are processed into the viral nonstructural proteins (nsp) by auto- and trans-cleavages of viral proteases nsp1, nsp2, and nsp4 (Snijder and Meulenberg, 1998). ORF4 encodes a minor glycoprotein (GP4) which is, next to a major glycoprotein (GP5) and two other minor glycoproteins (GP2a and GP3), found in the viral envelope, wherein all of said glycoproteins are important for infectious virus production. There are two distinct viral PRRSV genotypes causing similar clinical symptoms that diverge by about 40% on nucleotide sequence level, genotype I (EU) and genotype II (US). The North American (US) prototype strain is VR-2332, while the European (EU) prototype strain is Lelystad virus. The term "porcine reproductive and respiratory syndrome virus" in the scope of the present invention encompasses all strains, genotypes and serotypes of the PRRSV.

In connection with PRRSV it is understood that the terms "genotype I" and "genotype II" are equivalent to the terms "genotype 1" and "genotype 2" or to the terms "type 1" and "type 2", as frequently used in the literature in the context of PRRSV.

The terms "at least one porcine parvo virus (PPV) antigen" and "at least one porcine reproductive and respiratory syndrome (PRRS) virus antigen" in the scope of the present invention encompasses every antigen(s) from single PPV and/or PRRSV antigens to whole viruses comprising a multitude of antigens.

In another aspect, the present invention concerns an immunogenic composition or combination vaccine or combination as herein described and claimed, wherein the PPV is selected from the group consisting of: live attenuated/modified live PPV virus, killed/inactivated PPV virus, killed/inactivated PPV strain 014, German field isolates of Porcine parvovirus PPV-27a and PPV-143a, and Porcine parvovirus vaccine viruses PPV-NADL-2 and PPV-IDT (MSV).

The terms "live attenuated" and "modified live" are interchangeably used in the course of the present invention and particularly relate to a reduced virulence of a PPV and/or PRRSV, in particular of a wild type PPV and/or PRRS virus, which is achieved by conventional multiple cell-line passaging of the PPV and/or PRRSV and/or which is achieved by genetic engineering, wherein "virulence" is understood to be the degree of pathogenicity, and wherein "pathogenicity" is directed to the ability of the virus to induce clinical signs in the host or the offspring of the host, such as for instance reproductive failure.

The terms "killed" or "inactivated" in the scope of the present invention relate to a PPV and/or PRRSV not having the ability of infecting an appropriate subject (as opposed to a live virus) and/or whose infectivity is not given as compared to a native virus. In particular, a killed/inactivated virus cannot infect its native host cells (anymore).

In another aspect, the present invention concerns an immunogenic composition or combination vaccine or combination as herein described and claimed, wherein the at least one PPV antigen is one or more PPV subunit(s).

In another aspect, the present invention concerns an immunogenic composition or combination vaccine or combination as herein described and claimed, wherein the at least one PPV subunit(s) is PPV viral protein 2 (VP2), wherein preferably the PPV VP2 is the only PPV antigen.

The term "viral protein 2" or "VP2" relates to the capsid protein VP2 of the porcine parvovirus. The term "viral protein 2" or "VP2" is well known to the person skilled in the art.

The term "protein", "amino acid" and "polypeptide" are used interchangeably. The term "protein" refers to a sequence of amino acid residues composed of the natural occurring amino acids as well as derivatives thereof. The naturally occurring amino acids are well known in the art and are described in standard text books of biochemistry. Within the amino acid sequence the amino acid residues are connected by peptide bonds. Further, the two ends of the amino acid sequence are referred to as the carboxyl terminus (C-terminus) and the amino terminus (N-terminus). The term "protein" encompasses essentially purified proteins or protein preparations comprising other proteins in addition.

Further, the term also relates to protein fragments. Moreover, it includes chemically modified proteins. Such modifications may be artificial modifications or naturally occurring modifications such as phosphorylation, glycosylation, myristylation and the like.

In another aspect, the present invention concerns an immunogenic composition or combination vaccine or combination as herein described and claimed, wherein the PPV VP2 has:
  at amino acid position 228 a glutamic acid residue or a glutamate residue, and/or
  at amino acid position 414 a serine residue, and/or
  at amino acid position 419 a glutamine residue, and/or
  at amino acid position 436 a threonine residue,
wherein the numbering of the amino acid positions refers to the amino acid sequence of wild type PPV VP2.

The term "wherein the numbering of the amino acid positions refers to the amino acid sequence of wild type PPV VP2" relates to the numbering of amino acid positions referring to the amino acid sequence of full length wild type PPV VP2 protein. Preferably, the numbering of the amino positions as mentioned herein is with reference to a wild type PPV VP2 protein sequence having 579 amino acid residues, including a methionine residue at the (N-terminal) amino acid position 1. The term "wherein the numbering of the amino acid positions refers to the amino acid sequence of wild type PPV VP2" encompasses wild type PPV VP2 as exemplarily given in SEQ ID NO:1 (PPV 27a VP2).

In another aspect, the present invention concerns an immunogenic composition or combination vaccine or combination according as herein described and claimed, wherein the PPV VP2 further has:
  at amino acid position 25 an isoleucine residue, and/or
  at amino acid position 36 a serine residue, and/or
  at amino acid position 37 an isoleucine residue,
wherein the numbering of the amino acid positions refers to the amino acid sequence of wild type PPV VP2.

In another aspect, the present invention concerns an immunogenic composition or combination vaccine or combination as herein described and claimed, wherein the numbering of the amino acid positions refers to the amino acid sequence as shown in SEQ ID NO:1.

In another aspect, the present invention concerns an immunogenic composition or combination vaccine or combination as herein described and claimed, wherein the PPV VP2 is a recombinant PPV VP2.

The term "recombinant" as used herein, in particular refers to a protein molecule which is expressed from a recombinant DNA molecule, such as a polypeptide which is produced by recombinant DNA techniques. An example of such techniques includes the case when DNA encoding the expressed protein (e.g. PPV VP2) is inserted into a suitable expression vector, preferably a baculovirus expression vector, which is in turn used to transfect, or in case of a baculovirus expression vector to infect, a host cell to produce the protein or polypeptide encoded by the DNA. The term "recombinant PPV VP2", as used herein, thus, in particular refers to a protein molecule which is expressed from a recombinant DNA molecule.

In another aspect, the present invention concerns an immunogenic composition or combination vaccine or combination as herein described and claimed, wherein the PPV VP2 is a recombinant baculovirus expressed PPV VP2.

The term "baculovirus" is well known to the person skilled in the art. As used herein "baculovirus" in particular means a system for producing a desired protein in an insect cell using a recombinant baculovirus vector designed to express said protein. A baculovirus expression system generally comprises all elements necessary to achieve recombinant protein expression in insect cells, and typically involves the engineering of a baculovirus vector to express a desired protein, the introduction of the engineered baculovirus vector into insect cells, the culturing of the insect cells containing the engineered baculovirus vector in a suitable growth medium such that the desired protein is expressed, and the recovery of the protein. Typically, engineering a baculovirus vector involves the construction and isolation of recombinant baculoviruses in which the coding sequence for a chosen gene is inserted behind the promoter for a nonessential viral gene, wherein most of the presently used baculovirus expression systems are based on the sequence of Autographa californica nuclear polyhedrosis virus (AcMNPV) ((Virology 202 (2), 586-605 (1994), NCBI Accession No.: NC_001623). Baculovirus expression systems are well known in the art and have been described, for example, in "Baculovirus Expression Vectors: A Laboratory Manual" by David R. O'Reilly, Lois Miller, Verne Luckow, pub. by Oxford Univ. Press (1994), "The Baculovirus Expression System: A Laboratory Guide" by Linda A. King, R. D. Possee, published by Chapman & Hall (1992). An exemplary non-limiting example of a baculovirus system for producing a recombinant protein is e.g. described in WO 2006/072065 A2.

Preferred baculovirus vectors include baculovirus such as BACULOGOLD® (BD Biosciences Pharmingen, San Diego, Calif.) or DiamondBac (Sigma Aldrich), in particular provided that the production cells are insect cells. Although the baculovirus expression system is preferred, it is understood by those of skill in the art that other expression systems will work for purposes of the present invention, namely the expression of PPV VP2 into the supernatant of a cell culture. Such other expression systems may require the use of a signal sequence in order to cause PPV VP2 expression into the media.

In another aspect, the present invention concerns an immunogenic composition or combination vaccine or combination as herein disclosed and claimed, wherein the PPV VP2 comprises or consists of an amino acid sequence having at least 90% sequence identity with the amino acid sequence of SEQ ID NO:1, SEQ ID NO:2 and/or SEQ ID NO:5 to 16.

In another aspect, the present invention concerns an immunogenic composition or combination vaccine or combination as herein disclosed and claimed, wherein the PPV VP2 comprises or consists of an amino acid sequence having at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity with the amino acid sequence of SEQ ID NO:1, SEQ ID NO:2 and/or SEQ ID NO:5 to 16.

In another aspect, the present invention concerns an immunogenic composition or combination vaccine or combination as herein disclosed and claimed, wherein the PPV VP2 comprises or consists of the amino acid sequence of SEQ ID NO:1, SEQ ID NO:2 or SEQ ID NO:5 to 16 or comprises or consists of any fragment having at least 210, at least 250 or at least 300 contiguous amino acid residues from SEQ ID NO:1, SEQ ID NO:2 or SEQ ID NO:5 to 16.

In another aspect, the present invention concerns an immunogenic composition or combination vaccine or combination as herein disclosed and claimed, wherein the PPV VP2 comprises or consists of the amino acid sequence of SEQ ID NO:1, SEQ ID NO:2 or SEQ ID NO:5 to 16.

In another aspect, the present invention concerns an immunogenic composition or combination vaccine or combination as herein disclosed and claimed, wherein the PPV VP2 is encoded by a nucleotide sequence encoding an amino acid sequence having at least 90% sequence identity with the amino acid sequence of SEQ ID NO:1, SEQ ID NO:2 and/or SEQ ID NO:5 to 16.

In another aspect, the present invention concerns an immunogenic composition or combination vaccine or combination as herein disclosed and claimed, wherein the PPV VP2 is encoded by a nucleotide sequence encoding an amino acid sequence having at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity with the amino acid sequence of SEQ ID NO:1, SEQ ID NO:2 and/or SEQ ID NO:5 to 16.

In another aspect, the present invention concerns an immunogenic composition or combination vaccine or combination as herein disclosed and claimed, wherein the PPV VP2 is encoded by a nucleotide sequence encoding an amino acid sequence of SEQ ID NO:1, SEQ ID NO:2 or SEQ ID NO:5 to 16.

SEQ ID NO:4 is a codon-optimized PPV 27a VP2 nucleotide sequence which was further modified to possess two ClaI restriction enzyme sites (amino acid position 25 is an isoleucine residue, amino acid position 36 is a serine residue, amino acid position 37 is an isoleucine residue) so as to flank the VP2 coding region comprised of Glycine repeats. The ClaI sites were introduced in a manner so as to not disrupt the VP2 coding region. SEQ ID NO:2 is the protein sequence corresponding to SEQ ID NO:4. SEQ ID NO:3 is a codon-optimized PPV 27a VP2 nucleotide sequence (without ClaI restriction enzyme sites). SEQ ID NO:1 is the protein sequence corresponding to SEQ ID NO:3.

The terms "nucleic acid" or "nucleic acid sequence" or "nucleotide sequence" or "polynucleotide" are used interchangeably herein and refer to polynucleotides including DNA molecules, RNA molecules, cDNA molecules or derivatives. The term encompasses single as well as double stranded polynucleotides. The nucleic acid of the present invention encompasses isolated polynucleotides (i.e. isolated from its natural context) and genetically modified forms. Moreover, comprised are also chemically modified polynucleotides including naturally occurring modified polynucleotides such as glycosylated or methylated polynucleotides or artificial modified one such as biotinylated polynucleotides. Further, the terms "nucleic acid" and "polynucleotide" are interchangeable and refer to any nucleic acid. The terms "nucleic acid" and "polynucleotide" also specifically include nucleic acids composed of bases other than the five biologically occurring bases (adenine, guanine, thymine, cytosine and uracil).

The term "identity" or "sequence identity" is known in the art and refers to a relationship between two or more polypeptide sequences or two or more polynucleotide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences. Upon such alignment, sequence identity is ascertained on a position-by-position basis, e.g., the sequences are "identical" at a particular position if at that position, the nucleotides or amino acid residues are identical. The total number of such position identities is then divided by the total number of nucleotides or residues in the reference sequence to give % sequence identity. Sequence identity can be readily calculated by known methods, including but not limited to, those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinge, G., Academic Press (1987); Sequence Analysis Primer, Gribskov, M. and Devereux, J., eds., M. Stockton Press, New York (1991); and Carillo, H., and Lipman, D., SIAM J. Applied Math., 48: 1073 (1988), the teachings of which are incorporated herein by reference. Preferred methods to determine the sequence identity are designed to give the largest match between the sequences tested. Methods to determine sequence identity are codified in publicly available computer programs which determine sequence identity between given sequences. Examples of such programs include, but are not limited to, the GCG program package (Devereux, J., et al., Nucleic Acids Research, 12(1):387 (1984)), BLASTP, BLASTN and FASTA (Altschul, S. F. et al., J. Molec. Biol., 215:403-410 (1990). The BLASTX program is publicly available from NCBI and other sources (BLAST Manual, Altschul, S. et al., NCVI NLM NIH Bethesda, Md. 20894, Altschul, S. F. et al., J. Molec. Biol., 215:403-410 (1990), the teachings of which are incorporated herein by reference). These programs optimally align sequences using default gap weights in order to produce the highest level of sequence identity between the given and reference sequences. As an illustration, by a polynucleotide having a nucleotide sequence having at least, for example, 85%, preferably 90%, even more preferably 95% "sequence identity" to a reference nucleotide sequence, it is intended that the nucleotide sequence of the given polynucleotide is identical to the reference sequence except that the given polynucleotide sequence may include up to 15, preferably up to 10, even more preferably up to 5 point mutations per each 100 nucleotides of the reference nucleotide sequence. In other words, in a polynucleotide having a nucleotide sequence having at least 85%, preferably 90%, even more preferably 95% identity relative to the reference nucleotide sequence, up to 15%, preferably 10%, even more preferably 5% of the nucleotides in the reference sequence may be deleted or substituted with another nucleotide, or a number of nucleotides up to 15%, preferably 10%, even more preferably 5% of the total nucleotides in the reference sequence may be inserted into the reference sequence. These mutations of the reference sequence may occur at the 5'- or 3-terminal positions of the reference nucleotide sequence or anywhere between those terminal positions, interspersed either individually among nucleotides in the reference sequence or in one or more contiguous groups within the reference sequence. Analogously, by a polypeptide having a given amino acid sequence having at least, for example, 85%, preferably 90%, even more preferably 95% sequence identity to a reference amino acid sequence, it is intended that the given amino acid sequence of the polypeptide is identical to the reference sequence except that the given polypeptide sequence may include up to 15, preferably up to 10, even more preferably up to 5 amino acid alterations per each 100 amino acids of the reference amino acid sequence. In other words, to obtain a given polypeptide sequence having at least 85%, preferably 90%, even more preferably 95% sequence identity with a reference amino acid sequence, up to 15%, preferably up to 10%, even more preferably up to 5% of the amino acid residues in the reference sequence may be deleted or substituted with another amino acid, or a number of amino acids up to 15%, preferably up to 10%, even more preferably up to 5% of the total number of amino acid residues in the reference sequence may be inserted into the reference sequence. These alterations of the reference sequence may occur at the amino- or the carboxy-terminal positions of the reference amino acid sequence or anywhere between those terminal positions, interspersed either individually among residues in the reference sequence or in the one or more contiguous groups within the reference sequence. Preferably, residue positions which are not identical differ by conservative amino acid substitutions. However, conservative substitutions are not included as a match when determining sequence identity.

The terms "identity", "sequence identity" and "percent identity" are used interchangeably herein. For the purpose of this invention, it is defined here that in order to determine the percent identity of two amino acid sequences or two nucleic acid sequences, the sequences are aligned for optimal comparison purposes (e.g., gaps can be introduced in the sequence of a first amino or nucleic acid for optimal alignment with a second amino or nucleic acid sequence). The amino acid or nucleotide residues at corresponding amino acid or nucleotide positions are then compared. When a position in the first sequence is occupied by the same amino acid or nucleotide residue as the corresponding position in the second sequence, then the molecules are identical at that position. The percent identity between the two sequences is a function of the number of identical positions shared by the sequences (i.e., % identity=number of identical positions/total number of positions (i.e. overlapping positions)×100). Preferably, the two sequences are the same length.

A sequence comparison may be carried out over the entire lengths of the two sequences being compared or over fragment of the two sequences. Typically, the comparison will be carried out over the full length of the two sequences being compared. However, sequence identity may be carried out over a region of, for example, twenty, fifty, one hundred or more contiguous amino acid residues.

The skilled person will be aware of the fact that several different computer programs are available to determine the homology between two sequences. For instance, a comparison of sequences and determination of percent identity between two sequences can be accomplished using a mathematical algorithm. In a preferred embodiment, the percent identity between two amino acid or nucleic acid sequences is determined using the Needleman and Wunsch (J. Mol. Biol. (48): 444-453 (1970)) algorithm which has been incorporated into the GAP program in the Accelrys GCG software package (available at accelrys.com/products/gcg/), using either a Blosum 62 matrix or a PAM250 matrix, and a gap weight of 16, 14, 12, 10, 8, 6, or 4 and a length weight of 1, 2, 3, 4, 5, or 6. The skilled person will appreciate that all these different parameters will yield slightly different results but that the overall percentage identity of two sequences is not significantly altered when using different algorithms.

The protein sequences or nucleic acid sequences of the present invention can further be used as a "query sequence" to perform a search against public databases to, for example, to identify other family members or related sequences. Such searches can be performed using the BLASTN and BLASTP programs (version 2.0) of Altschul, et al. (1990) J. Mol. Biol. 215:403-10. BLAST protein searches can be performed with the BLASTP program, score=50, wordlength=3 to obtain amino acid sequences homologous to protein molecules of the invention. To obtain gapped alignments for comparison purposes, Gapped BLAST can be utilized as described in Altschul et al. (1997) Nucleic Acids Res. 25(17): 3389-3402. When utilizing BLAST and Gapped BLAST programs, the default parameters of the respective programs (e.g., BLASTP and BLASTN) can be used. See the homepage of the National Center for Biotechnology Information at ncbi.nlm.nih.gov/.

In another aspect, the present invention concerns an immunogenic composition or combination vaccine or combination as herein disclosed and claimed, wherein the PRRS virus is selected from the group consisting of: PRRS virus genotype 1, PRRS virus genotype 2, PRRS virus genotype 1 comprising a genome encoded by a nucleotide sequence having at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, at least 99.9%, or 100% identity with the nucleic acid sequence of SEQ ID NO:17 (Lelystad wild-type sequence), PRRS virus genotype 2 comprising a genome encoded by a nucleotide sequence having at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, at least 99.9%, or 100% identity with the nucleic acid sequence of SEQ ID NO:18 (VR2332 wild-type sequence).

In another aspect, the present invention concerns an immunogenic composition or combination vaccine or combination as herein disclosed and claimed, wherein the PRRS virus is selected from the group consisting of: live attenuated/modified live PRRS virus, live attenuated/modified live PRRS virus type 1 genotype (e.g. PORCILIS® PRRS (Intervet, Inc.), Unistrain PRRS, Amervac PRRS, etc.), live attenuated/modified live PRRS virus type 2 genotype (e.g. INGELVAC® PRRS MLV, FOSTERA® PRRS (Zoetis Services LLC), etc.), live attenuated/modified live PRRS virus strain 94881 [(genotype 1), REPROCYC® PRRS EU], killed/inactivated PRRS virus, killed/inactivated PRRS virus type 1 genotype (e.g., Progressis), killed/inactivated PRRS virus type 2 genotype, Lelystad virus strain (CDI-NL-2.91, Institut Pasteur, Paris, France, deposit number I-1102), PRRS virus subunit(s), or other strains such as those deposited under the Accession Numbers ECACC 04102703, ECACC 04102702, ECACC 04102704, CNCM Accession No. I-1140, CNCM Accession No I-1387, CNCM Accession No I-1388, ATCC VR 2332, VR 2385, VR 2386, VR 2429, VR 2474, and VR 2402; CNCM I-1102, CNCM I-1140, CNCM I-1387, CNCM I-1388, or ECACC V93070108, North American PRRS virus pT7P129A (ATCC Accession No. 203488), ATCC deposit VR-2332, ATCC deposit VR-2368; ATCC VR-2495; ATCC VR 2385, ATCC VR 2386, ATCC VR 2429, ATCC VR 2474, and ATCC VR 2402.

The terms "immunogenic composition" or "combination vaccine" or "combination" refer to a composition that comprises at least one antigen, in case of combination vaccine" or "combination" at least two antigens, which elicit(s) an immunological response in the host to which the "immunogenic composition" or "combination vaccine" or "combination" is administered. Such immunological response may be a cellular and/or antibody-mediated immune response to the "immunogenic composition" or "combination vaccine" or "combination" of the invention. Preferably, the "immunogenic composition" or "combination vaccine" or "combination" induces an immune response and, more preferably, confers protective immunity against one or more of the clinical signs of a PPV and/or PRRSV infection. The host is also described as "subject". Preferably, any of the hosts or subjects described or mentioned herein are swine.

Usually, an "immunological response" includes but is not limited to one or more of the following effects: the production or activation of antibodies, B cells, helper T cells, suppressor T cells, and/or cytotoxic T cells and/or gamma-delta T cells, directed specifically to an antigen or antigens included in the "immunogenic composition" or "combination vaccine" or "combination" of the invention. Preferably, the host will display either a protective immunological response or a therapeutically response.

A "protective immunological response" or "protective immunity" will be demonstrated by either a reduction or lack of clinical signs normally displayed by an infected host, a quicker recovery time and/or a lowered duration of infectivity or lowered pathogen titer in the tissues or body fluids or excretions of the infected host.

In case where the host displays a protective immunological response such that resistance to new infection will be enhanced and/or the clinical severity of the disease reduced, the "immunogenic composition" or "combination" is described as a "vaccine".

In another aspect, the present invention concerns an immunogenic composition or combination vaccine or combination as herein disclosed and claimed, wherein the immunogenic composition or combination vaccine or combination is formulated for a single-dose administration.

The volume for the single-dose administration has been defined elsewhere herein.

The immunogenic composition or combination vaccine or combination as herein disclosed and claimed is, preferably, administered topically or systemically. Suitable routes of administration conventionally used are oral or parenteral administration, such as intranasal, intravenous, intramuscular, intraperitoneal, subcutaneous, as well as inhalation. However, depending on the nature and mode of action of a compound, the immunogenic composition or combination vaccine or combination as herein disclosed and claimed may be administered by other routes as well. Most preferred the immunogenic composition or combination vaccine or combination as herein disclosed and claimed is administered intramuscularly.

In another aspect, the present invention concerns an immunogenic composition or combination vaccine or combination as herein disclosed and claimed, wherein the immunogenic composition or combination vaccine or combination is administered intramuscularly.

In another aspect, the present invention concerns an immunogenic composition or combination vaccine or combination as herein disclosed and claimed, wherein the immunogenic composition or combination vaccine or combination is safe for gilts and/or sows during pregnancy and lactation.

In another aspect, the present invention concerns an immunogenic composition or combination vaccine or combination as herein disclosed and claimed, wherein the immunogenic composition or combination vaccine or combination is safe for gilts and/or sows from 30 days of gestation, preferably from 40 days of gestation.

In another aspect, the present invention concerns an immunogenic composition or combination vaccine or combination as herein disclosed and claimed, wherein the immunogenic composition or combination vaccine or combination further comprises at least one pharmaceutically acceptable carrier.

The term "pharmaceutical-acceptable carrier" includes any and all solvents, dispersion media, coatings, stabilizing agents, diluents, preservatives, antibacterial and antifungal agents, isotonic agents, adsorption delaying agents, adjuvants, immune stimulants, and combinations thereof.

"Diluents" can include water, saline, dextrose, ethanol, glycerol, phosphate buffered saline and the like. Isotonic agents can include sodium chloride, dextrose, mannitol, sorbitol, and lactose, among others. Stabilizers include albumin and alkali salts of ethylendiamintetracetic acid, among others.

In one aspect of the present invention the pharmaceutically acceptable carrier is a carbomer.

Preferably, the immunogenic composition can further include one or more other immunomodulatory agents such as, e.g. interleukins, interferons, or other cytokines. The amounts and concentrations of adjuvants and additives useful in the context of the present invention can readily be determined by the skilled artisan.

In some aspects, the immunogenic composition of the present invention contains an adjuvant. "Adjuvants" as used herein, can include aluminum hydroxide and aluminum phosphate, saponins e.g., QUIL-A®, QS-21 (Cambridge Biotech Inc., Cambridge Mass.), GPI-0100 (Galenica Pharmaceuticals, Inc., Birmingham, Ala.), water-in-oil emulsion, oil-in-water emulsion, water-in-oil-in-water emulsion. The emulsion can be based in particular on light liquid paraffin oil (European Pharmacopea type); isoprenoid oil such as squalane or squalene; oil resulting from the oligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the PLURONIC® products (BASF Corporation), especially L121. See Hunter et al., The Theory and Practical Application of Adjuvants (Ed. Stewart-Tull, D. E. S.), JohnWiley and Sons, NY, pp 51-94 (1995) and Todd et al., Vaccine 15:564-570 (1997). Exemplary adjuvants are the SPT emulsion described on page 147 of "Vaccine Design, The Subunit and Adjuvant Approach" edited by M. Powell and M. Newman, Plenum Press, 1995, and the emulsion MF59 described on page 183 of this same book.

A further instance of an adjuvant is a compound chosen from the polymers of acrylic or methacrylic acid and the copolymers of maleic anhydride and alkenyl derivative. Advantageous adjuvant compounds are the polymers of acrylic or methacrylic acid which are cross-linked, especially with polyalkenyl ethers of sugars or polyalcohols. These compounds are known by the term carbomer (Phameuropa Vol. 8, No. 2, June 1996). Persons skilled in the art can also refer to U.S. Pat. No. 2,909,462 (incorporated by reference) which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. The products sold under the name CARBOPOL®; (BF Goodrich, Ohio, USA) are particularly appropriate. They are cross-linked with an allyl sucrose or with allyl pentaerythritol. Among them, there may be mentioned CARBOPOL® 974P, 934P and 971P. Most preferred is the use of CARBOPOL® 971P. Among the copolymers of maleic anhydride and alkenyl derivative, are the copolymers EMA (Monsanto), which are copolymers of maleic anhydride and ethylene. The dissolution of these polymers in water leads to an acid solution that will be neutralized, preferably to physiological pH, in order to give the adjuvant solution into which the immunogenic, immunological or vaccine composition itself will be incorporated.

Further suitable adjuvants include, but are not limited to, the RIBI adjuvant system (Ribi Inc.), Block co-polymer (CytRx, Atlanta Ga.), SAF-M (Chiron, Emeryville Calif.), monophosphoryl lipid A, Avridine lipid-amine adjuvant, heat-labile enterotoxin from *E. coli* (recombinant or otherwise), cholera toxin, IMS 1314 or muramyl dipeptide, or naturally occurring or recombinant cytokines or analogs thereof or stimulants of endogenous cytokine release, among many others.

It is expected that an adjuvant can be added in an amount of about 100 μg to about 10 mg per dose, preferably in an amount of about 100 μg to about 10 mg per dose, more preferably in an amount of about 500 μg to about 5 mg per dose, even more preferably in an amount of about 750 μg to about 2.5 mg per dose, and most preferably in an amount of about 1 mg per dose. Alternatively, the adjuvant may be at a concentration of about 0.01% to 50%, preferably at a concentration of about 2% to 30%, more preferably at a concentration of about 5% to 25%, still more preferably at a concentration of about 7% to 22%, and most preferably at a concentration of 10% to 20% by volume of the final product.

In another aspect, the present invention concerns an immunogenic composition or combination vaccine or combination as herein disclosed and claimed, wherein the at least one pharmaceutically acceptable carrier is a carbomer.

In another aspect, the present invention concerns an immunogenic composition or combination vaccine or combination as herein disclosed and claimed, wherein the immunogenic composition or combination vaccine or combination comprises 0.1 μg to 50 μg of the PPV VP2 antigen, preferably 0.5 μg to 10 μg of the PPV VP2 antigen, more preferably 1.0 μg to 10 μg of the PPV VP2 antigen, and/or 3.9 to 7.0 $\log_{10}TCID_{50}$ of the PRRS virus.

In another aspect, the present invention concerns an immunogenic composition or combination vaccine or combination as herein disclosed and claimed comprises between about 0.1 μg and 50 μg of the PPV VP2 antigen. Preferably, the immunogenic composition comprises between about 0.2 μg and 40 μg, more preferably between about 0.3 μg and 30 μg, more preferably between about 0.4 μg and 20 μg and even more preferably between about 0.5 μg and 10 μg and even more preferably between about 1.0 μg and 10 μg with an amount of 0.5 μg, 0.75 μg, 1 μg, 1.25 μg, 1.5 μg, 2 μg, 2.5 μg, 3 μg, 3.5 μg, 4 μg, 4.5 μg, 5 μg, 5.5 μg, 6 μg, 6.5 μg, 7 μg, 7.5 μg, 8 μg, 8.5 μg, 9 μg, 9.5 μg or 10 μg of the PPV VP2 antigen most preferred.

In another aspect, the present invention concerns an immunogenic composition or combination vaccine or combination as herein disclosed and claimed comprises between about 3.9 to 7.0 $\log_{10}TCID_{50}$ of the PRRS virus.

In another aspect, the present invention concerns an immunogenic composition or combination as herein disclosed and claimed, wherein the immunogenic composition or combination is a vaccine.

The term "vaccine" already has been described elsewhere herein. However, in case where the host displays a protective immunological response such that resistance to new infection will be enhanced and/or the clinical severity of the disease reduced, the immunogenic composition or combination is described as a "vaccine.

In another aspect, the present invention concerns an immunogenic composition or combination vaccine or combination as herein disclosed and claimed protects against a homologous and/or a heterologous challenge. Advantageously, the experimental data provided by the present invention disclose that the immunogenic composition or combination vaccine or combination of the present invention has a broad protection spectrum as it protects against heterologous North American and/or heterologous European challenge strains.

The terms "protects" and "prophylaxis" and "preventing" are used interchangeably in this application. These terms have been defined elsewhere.

In another aspect, the present invention concerns an immunogenic composition or combination vaccine or combination as herein disclosed and claimed protects against a challenge with North American and/or European isolates.

The term "North American and/or European isolates" is well known to the person skilled in the art. The term "North American and/or European isolates" encompasses all isolates which have been or will be isolated in North America and Europe.

In another aspect, the present invention concerns an immunogenic composition or combination vaccine or combination as herein disclosed and claimed is cross protective against North American and/or European isolates.

In another aspect, the present invention concerns an immunogenic composition or combination vaccine or combination as herein disclosed and claimed is effective in the treatment and/or prophylaxis of clinical signs caused by a PPV and/or PRRSV infection in a subject of need. The terms "treatment and/or prophylaxis", "clinical signs" and "of need" have been defined elsewhere.

In another aspect, the present invention concerns an immunogenic composition or combination vaccine or combination as herein disclosed and claimed, wherein the immunogenic composition or combination vaccine or combination protects against a homologous and/or a heterologous challenge with PPV and/or a homologous and/or a heterologous challenge with PRRS virus.

In another aspect, the present invention concerns an immunogenic composition or combination vaccine or combination as herein disclosed and claimed, wherein the immunogenic composition or combination vaccine or combination protects against a challenge with North American and/or European isolates of PPV and/or against a challenge with North American and/or European isolates of PRRS virus.

In another aspect, the present invention concerns an immunogenic composition or combination vaccine or combination as herein disclosed and claimed, wherein the immunogenic composition or combination vaccine or combination is cross-protective against North American and/or European isolates of PPV and/or is cross-protective against North American and/or European isolates of PRRS virus.

In another aspect, the present invention concerns an immunogenic composition or combination vaccine or combination as herein disclosed and claimed, wherein the immunogenic composition or combination vaccine or combination is effective in the treatment and/or prophylaxis of clinical signs caused by a PPV infection and/or a PRRS virus infection in a subject of need.

Further, the present invention provides a virus like particle comprising the PPV VP2 as described and claimed herein.

The term "virus like particle" (VLP) encompasses a non-replicating, empty viral shell from a virus. VLPs are generally composed of one or more viral proteins, such as, but not limited to those proteins referred to as capsid, coat, shell, surface and/or envelope proteins, or particle-forming polypeptides derived from these proteins. VLPs can form spontaneously upon recombinant expression of the protein in an appropriate expression system. The presence of VLPs following recombinant expression of viral proteins can be detected using conventional techniques known in the art, such as by electron microscopy, X-ray crystallography, and the like. See, e.g., Baker et al., Biophys. J. (1991) 60: 1445-1456; Hagensee et al., J. Virol. (1994) 68: 4503-4505. For example, cryoelectron microscopy can be performed on vitrified aqueous samples of the VLP preparation in question, and images recorded under appropriate exposure conditions.

The term "virus like particle" (VLP) also encompasses VLPs which are composed of a plurality of PPV VP2.

In another aspect of the present invention the virus like particle is composed of a plurality of the PPV VP2 as described and claimed herein.

Further, the present invention provides a cell comprising the polynucleotide or the vector as described herein. Preferably, the vector is a baculovirus.

The term "cell" is well known to the person skilled in the art. The term "cell" encompasses eukaryotic cell such as an animal cell, protist cell, plant cell, or fungal cell. Preferably the eukaryotic cell is a mammalian cell such as CHO, BHK or COS, or a fungal cell such as *Saccharomyces cerevisiae*, or an insect cell such as Sf9.

In another aspect of the present invention the cell is an insect cell.

"Insect cell" as used herein means a cell or cell culture derived from an insect species. Of particular interest with respect to the present invention are insect cells derived from the species *Spodoptera frugiperda* and *Trichoplusia ni*.

Preferably, the insect cell, as mentioned herein, is a *Spodoptera Frugiperda* (Sf) cell or a cell from a cell line derived from *Spodoptera Frugiperda*, and is more preferably selected from the group consisting of Sf9 cell and Sf+ cell. Respectively, the insect cells, as mentioned herein, are preferably *Spodoptera Frugiperda* (Sf) cells or cells from a cell line derived from *Spodoptera Frugiperda*, and are more preferably selected from the group consisting of Sf9 cells and Sf+ cells.

In another aspect of the present invention the insect cell is selected from the group consisting of Sf9 cells and Sf+ cells.

Further, the present invention provides a method of producing the PPV VP2 as described and claimed herein, comprising transfecting a cell with the vector as described herein.

The term "vector" is well known to the person skilled in the art. The term "vector" as it is known in the art refers to a polynucleotide construct, typically a plasmid or a virus, used to transmit genetic material to a host cell. Vectors can be, for example, viruses, plasmids, cosmids, or phage. A vector as used herein can be composed of either DNA or RNA. In some embodiments, a vector is composed of DNA.

An "expression vector" is a vector that is capable of directing the expression of a protein encoded by one or more genes carried by the vector when it is present in the appropriate environment. Vectors are preferably capable of autonomous replication. Typically, an expression vector comprises a transcription promoter, a gene, and a transcription terminator. Gene expression is usually placed under the control of a promoter, and a gene is said to be "operably linked to" the promoter.

As used herein, the term "operably linked" is used to describe the connection between regulatory elements and a gene or its coding region. Typically, gene expression is placed under the control of one or more regulatory elements, for example, without limitation, constitutive or inducible promoters, tissue-specific regulatory elements, and enhancers. A gene or coding region is said to be "operably linked to" or "operatively linked to" or "operably associated with" the regulatory elements, meaning that the gene or coding region is controlled or influenced by the regulatory element. For instance, a promoter is operably linked to a coding sequence if the promoter effects transcription or expression of the coding sequence.

Vectors and methods for making and/or using vectors (or recombinants) for expression can be by or analogous to the methods disclosed in: U.S. Pat. Nos. 4,603,112, 4,769,330, 5,174,993, 5,505,941, 5,338,683, 5,494,807, 4,722,848, 5,942,235, 5,364,773, 5,762,938, 5,770,212, 5,942,235, 382, 425, PCT publications WO 94/16716, WO 96/39491, WO 95/30018; Paoletti, "Applications of pox virus vectors to vaccination: An update, "PNAS USA 93: 11349-11353, October 1996; Moss, "Genetically engineered poxviruses for recombinant gene expression, vaccination, and safety," PNAS USA 93: 11341-11348, October 1996; Smith et al., U.S. Pat. No. 4,745,051 (recombinant baculovirus); Richardson, C. D. (Editor), Methods in Molecular Biology 39, "Baculovirus Expression Protocols" (1995 Humana Press Inc.); Smith et al., "Production of Human Beta Interferon in Insect Cells Infected with a Baculovirus Expression Vector", Molecular and Cellular Biology, December, 1983, Vol. 3, No. 12, p. 2156-2165; Pennock et al., "Strong and Regulated Expression of *Escherichia coli* B-Galactosidase in Infect Cells with a Baculovirus vector, "Molecular and Cellular Biology March 1984, Vol. 4, No. 3, p. 406; EPAO 370 573; U.S. application No. 920,197, filed Oct. 16, 1986; EP Patent publication No. 265785; U.S. Pat. No. 4,769,331 (recombinant herpesvirus); Roizman, "The function of herpes simplex virus genes: A primer for genetic engineering of novel vectors," PNAS USA 93:11307-11312, October 1996; Andreansky et al., "The application of genetically engineered herpes simplex viruses to the treatment of experimental brain tumors," PNAS USA 93: 11313-11318, October 1996; Robertson et al., "Epstein-Barr virus vectors for gene delivery to B lymphocytes", PNAS USA 93: 11334-11340, October 1996; Frolov et al., "Alphavirus-based expression vectors: Strategies and applications," PNAS USA 93: 11371-11377, October 1996; Kitson et al., J. Virol. 65, 3068-3075, 1991; U.S. Pat. Nos. 5,591,439, 5,552,143; WO 98/00166; allowed U.S. application Ser. Nos. 08/675, 556, and 08/675,566 both filed Jul. 3, 1996 (recombinant adenovirus); Grunhaus et al., 1992, "Adenovirus as cloning vectors," Seminars in Virology (Vol. 3) p. 237-52, 1993; Ballay et al. EMBO Journal, vol. 4, p. 3861-65, Graham, Tibtech 8, 85-87, April, 1990; Prevec et al., J. Gen Virol. 70, 42434; PCT WO 91/11525; Felgner et al. (1994), J. Biol.

Chem. 269, 2550-2561, Science, 259: 1745-49, 1993; and McClements et al., "Immunization with DNA vaccines encoding glycoprotein D or glycoprotein B, alone or in combination, induces protective immunity in animal models of herpes simplex virus-2 disease", PNAS USA 93: 11414-11420, October 1996; and U.S. Pat. Nos. 5,591,639, 5,589,466, and 5,580,859, as well as WO 90/11092, WO 93/19183, WO 94/21797, WO 95/11307, WO 95/20660; Tang et al., Nature, and Furth et al., Analytical Biochemistry, relating to DNA expression vectors, inter alia. See also WO 98/33510; Ju et al., Diabetologia, 41: 736-739, 1998 (lentiviral expression system); Sanford et al., U.S. Pat. No. 4,945,050; Fischbach et al. (Intracel); WO 90/01543; Robinson et al., Seminars in Immunology vol. 9, pp. 271-283 (1997), (DNA vector systems); Szoka et al., U.S. Pat. No. 4,394,448 (method of inserting DNA into living cells); McCormick et al., U.S. Pat. No. 5,677,178 (use of cytopathic viruses); and U.S. Pat. No. 5,928,913 (vectors for gene delivery), all incorporated by reference; as well as other documents cited herein.

The term "regulatory element" and "expression control element" are used interchangeably and refer to nucleic acid molecules that can influence the expression of an operably linked coding sequence in a particular host organism. These terms are used broadly to and cover all elements that promote or regulate transcription, including promoters, core elements required for basic interaction of RNA polymerase and transcription factors, upstream elements, enhancers, and response elements. Exemplary regulatory elements in prokaryotes include promoters, operator sequences and a ribosome binding sites. Regulatory elements that are used in eukaryotic cells can include, without limitation, transcriptional and translational control sequences, such as promoters, enhancers, splicing signals, polyadenylation signals, terminators, protein degradation signals, internal ribosome-entry element (IRES), 2A sequences, and the like, that provide for and/or regulate expression of a coding sequence and/or production of an encoded polypeptide in a host cell.

As used herein, the term "promoter" is a nucleotide sequence that permits binding of RNA polymerase and directs the transcription of a gene. Typically, a promoter is located in the 5' non-coding region of a gene, proximal to the transcriptional start site of the gene. Sequence elements within promoters that function in the initiation of transcription are often characterized by consensus nucleotide sequences. Examples of promoters include, but are not limited to, promoters from bacteria, yeast, plants, viruses, and mammals (including humans). A promoter can be inducible, repressible, and/or constitutive. Inducible promoters initiate increased levels of transcription from DNA under their control in response to some change in culture conditions, such as a change in temperature.

As used herein, the term "enhancer" refers to a type of regulatory element that can increase the efficiency of transcription, regardless of the distance or orientation of the enhancer relative to the start site of transcription.

Generation of a viral vector can be accomplished using any suitable genetic engineering techniques well known in the art, including, without limitation, the standard techniques of restriction endonuclease digestion, ligation, transformation, plasmid purification, and DNA sequencing, for example as described in Sambrook et al. (Molecular Cloning: A Laboratory Manual. Cold Spring Harbor Laboratory Press, N.Y. (1989)).

Further, the present invention provides a method of producing the PPV VP2 as described herein, comprising infecting a cell, preferably an insect cell, with the baculovirus as described herein.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration preferably for administration to animals, especially swine. Associated with such container(s) can be a notice in the form prescribed by a governmental agency regulating the manufacture, use or sale of pharmaceuticals or biological products, which notice reflects approval by the agency of manufacture, use or sale for human administration.

In another aspect, the present invention concerns an immunogenic composition or combination vaccine or combination as herein disclosed and claimed, wherein the at least one porcine parvovirus (PPV) antigen and the at least one porcine reproductive and respiratory syndrome (PRRS) virus antigen are contained together in one single container or are spatially separated from each other, preferably are contained in two or more separate containers.

In another aspect, the present invention concerns a kit comprising the immunogenic composition or combination vaccine or combination as herein disclosed and claimed.

In another aspect, the present invention concerns a kit as herein disclosed and claimed, wherein the at least one porcine parvo virus (PPV) antigen and the at least one porcine reproductive and respiratory syndrome (PRRS) virus antigen are contained separately from each other in two or more separate containers, preferably both independently from each other either in lyophilized or in frozen form, and wherein the kit further comprises an instruction manual for mixing the spatially separated at least one PPV antigen and at least one PRRS virus antigen, wherein preferably such instruction manual contains directions to combine the contents of the container(s) containing the at least one PPV antigen with the contents of the container(s) containing the at least one PPRS virus antigen, wherein more preferably such instruction manual contains directions that the at least one porcine parvovirus (PPV) antigen and the at least one porcine reproductive and respiratory syndrome (PRRS) virus antigen are to be administered to the subject simultaneously, more preferably separately simultaneously at the same or different administration sites, sequentially (in any order), and/or in a chronologically staggered fashion.

In another aspect, the present invention concerns a kit as herein disclosed and claimed, wherein the kit further comprises directions for the treatment and/or prophylaxis of diseases in swine and/or further comprises directions for the treatment and/or prophylaxis of PPV infections and/or PRRS virus infections, preferably such kit further comprises directions for the associated use of the PPV component (preferably as separated kit component) and the PRRSV component (preferably as separated kit component) of the immunogenic composition or combination vaccine or combination as herein disclosed and claimed and contained in such kit.

The term "associated use" in the scope of the present invention relates to the use of the two vaccines or vaccine components PRRSV and PPV (each independently from each other also herein referred to as "separated kit component") by mixing the two vaccines before the administration at one injection site or the administration of the two vaccines at the same time but at different administration sites. Preferably, such two vaccines are administered simultaneously, more preferably separately simultaneously at the same or different administration sites, sequentially (in any order), and/or in a chronologically staggered fashion.

In another aspect of the present invention the PPV and/or PRRSV of the present invention has been inactivated resulting in whole inactivated virus with a viral protein 2 (VP2) as described herein.

Any conventional inactivation method can be used for purposes of the present invention. Thus, inactivation can be performed by chemical and/or physical treatments which are known to the person skilled in the art. Preferred inactivation methods include the addition of cyclized binary ethylenimine (BEI) including the addition of a solution of 2-bromoethyleneamine hydrobromide (BEA), which has been cyclized to binary ethylenimine (BEI). Preferred further chemical inactivation agents comprise but are not limited to Triton X-100, Sodium deoxycholate, Cetyltrimethylammonium bromide, β-Propiolactone, Thimerosal, Phenol and Formaldehyde (Formalin). However, the inactivation may also comprise a neutralization step. Preferred neutralization agents include but are not limited to sodium thiosulfate, sodium bisulfite and the alike.

Preferred formalin inactivation conditions include formalin concentration between from about 0.02% (v/v)-2.0% (v/v), more preferably from about 0.1% (v/v)-1.0% (v/v), still more preferably from about 0.15% (v/v)-0.8% (v/v), even more preferably from about 0.16% (v/v)-0.6% (v/v), and most preferably about 0.2% (v/v)-0.4% (v/v). Incubation time depends on the resistance of the PPV and/or PRRSV. In general, the inaction process is performed until no growth of the PPV and/or PRRSV can be detected in a suitable cultivation system.

Preferably, the inactivated PPV and/or PRRSV of the present invention is formalin inactivated, preferably using the concentrations as described hereinabove.

Preferably, the inactivated PPV and/or PRRSV of the present invention is cyclized binary ethylenimine (BEI) inactivated, including the addition of a solution of 2-bromoethyleneamine hydrobromide (BEA), which has been cyclized to binary ethylenimine (BEI).

The inactivated PPV and/or PRRSV of the invention may be incorporated into liposomes using known technology such as that described in Nature, 1974, 252, 252-254 or Journal of Immunology, 1978, 120, 1109-1113. In another embodiment of the invention, the inactivated PPV of the invention may be conjugated to suitable biological compounds such as polysaccharides, peptides, proteins, or the like, or a combination thereof.

The term "immunizing" relates to an active immunization by the administration of an immunogenic composition to a subject to be immunized, thereby causing an immunological response against the antigen included in such immunogenic composition.

Preferably, immunization results in lessening of the incidence of the particular PPV and/or PRRSV infection in a herd or in the reduction in the severity of clinical signs caused by or associated with the particular PPV and/or PRRSV infection.

Further, the immunization of a subject in need with the immunogenic compositions as provided herewith, results in preventing infection of a subject by PPV and/or PRRSV infection. Even more preferably, immunization results in an effective, long-lasting, immunological-response against PPV and/or PRRSV infection. It will be understood that the said period of time will last more than 1 month, preferably more than 2 months, preferably more than 3 months, more preferably more than 4 months, more preferably more than 5 months, more preferably more than 6 months. It is to be understood that immunization may not be effective in all subjects immunized. However, the term requires that a significant portion of subjects of a herd are effectively immunized.

Preferably, a herd of subjects is envisaged in this context which normally, i.e. without immunization, would develop clinical signs caused by or associated with a PPV and/or PRRSV infection. Whether the subjects of a herd are effectively immunized can be determined without further ado by the person skilled in the art. Preferably, the immunization shall be effective if clinical signs in at least 33%, at least 50%, at least 60%, at least 70%, at least 80%, at least 90%, still more preferably in at least 95% and most preferably in 100% of the subjects of a given herd are lessened in incidence or severity by at least 10%, more preferably by at least 20%, still more preferably by at least 30%, even more preferably by at least 40%, still more preferably by at least 50%, even more preferably by at least 60%, still more preferably by at least 70%, even more preferably by at least 80%, still more preferably by at least 90%, still more preferably by at least 95% and most preferably by 100% in comparison to subjects that are either not immunized or immunized with an immunogenic composition that was available prior to the present invention but subsequently infected by the particular PPV.

In another aspect, the present invention concerns the use of the immunogenic composition or combination vaccine or combination or the kit as herein described and claimed for the preparation of a medicament, preferably of a vaccine.

In another aspect, the present invention concerns the use of the immunogenic composition or combination vaccine or combination or the kit as herein described and claimed for the treatment and/or prevention of an infection with PPV and/or PRRS virus, the reduction, prevention or treatment of clinical signs caused by an infection with PPV and/or PRRS virus, or for the treatment and/or prevention of a disease caused by an infection with PPV and/or PRRS virus.

In another aspect, the present invention concerns a method of immunizing a subject comprising administering to such subject an immunogenic composition or combination vaccine or combination (or separated kit components) as herein described and claimed.

In another aspect, the present invention concerns a method of treating and/or preventing clinical signs caused by a PPV infection and/or a PRRS virus infection, preferably Porcine Reproductive and Respiratory Syndrome, preferably in swine, in a subject of need, the method comprising administering to the subject a therapeutically effective amount of an immunogenic composition or combination vaccine or combination (or separated kit components) as herein described and claimed.

In another aspect, the present invention concerns a method of reducing the reproductive failure in a subject in comparison to a subject of a non-immunized control group of the same species, the method comprising administering to the subject a therapeutically effective amount of an immunogenic composition or combination vaccine or combination (or separated kit components) as herein described and claimed.

In another aspect, the present invention concerns a method of reducing embryonic and fetal death in a subject in comparison to a subject of a non-immunized control group of the same species, the method comprising administering to the subject a therapeutically effective amount of an immunogenic composition or combination vaccine or combination (or separated kit components) as herein described and claimed.

In another aspect, the present invention concerns a method for active immunization of breeding pigs (sows and gilts) for protection of embryos and fetuses against porcine parvovirus infection, the method comprising administering to such pigs (sows and gilts) a therapeutically effective amount of an immunogenic composition or combination vaccine or combination (or separated kit components) as herein described and claimed.

In another aspect, the present invention concerns the methods as herein described and claimed, wherein said subject is selected from the group consisting of swine, cattle, cat and dog, preferably swine, more preferably sow and/or gilt.

In another aspect, the present invention concerns the methods as herein described and claimed, wherein the immunogenic composition or combination vaccine or combination (or separated kit components) is administered once or at two or more doses.

In another aspect, the present invention concerns the methods as herein described and claimed, wherein the immunogenic composition or combination vaccine or combination (or separated kit components) is administered intramuscularly.

In another aspect, the present invention concerns the methods as herein described and claimed, wherein the immunogenic composition or combination vaccine or combination (or separated kit components) is administered to gilts and/or sows, preferably to gilts and/or sows being at least 3 weeks of age, more preferably to gilts and/or sows before pregnancy, even more preferably to sows during pregnancy and lactation.

In another aspect, the present invention concerns the methods as herein described and claimed, wherein the immunogenic composition or combination vaccine or combination (or separated kit components) is safe for gilts and/or sows during pregnancy and lactation and gilts before pregnancy.

In another aspect, the present invention concerns the methods as herein described and claimed, wherein the immunogenic composition or combination vaccine or combination (or separated kit components) is safe for sows and/or gilts from 30 days of gestation, preferably from 40 days of gestation.

In another aspect, the present invention concerns the methods as herein described and claimed, wherein the immunogenic composition or combination vaccine or combination (or separated kit components) comprises 0.1 µg to 50 µg of the PPV VP2 antigen, preferably 0.5 µg to 10 µg of the PPV VP2 antigen, more preferably 1.0 µg to 10 µg of the PPV VP2 antigen and/or 3.9 to 7.0 $\log_{10}TCID_{50}$ of the PRRS virus.

In another aspect, the present invention concerns the methods as herein described and claimed, wherein the immunogenic composition or combination vaccine or combination (or separated kit components) protects against a homologous and/or a heterologous challenge with PPV and/or a homologous and/or a heterologous challenge with PRRS virus.

In another aspect, the present invention concerns the methods as herein described and claimed, wherein the immunogenic composition or combination vaccine or combination (or separated kit components) protects against a challenge with North American and/or European isolates of PPV and/or against a challenge with North American and/or European isolates of PRRS virus.

In another aspect, the present invention concerns the methods as herein described and claimed, wherein the immunogenic composition or combination vaccine or combination (or separated kit components) is cross-protective against North American and/or European isolates of PPV and/or is cross-protective against North American and/or European isolates of PRRS virus.

In another aspect, the present invention concerns the methods as herein described and claimed, wherein said method results in an improvement of at least one efficacy parameter selected from the group consisting of: reduced transient leukopenia and reproductive failure characterized by embryonic and/or fetal infection and death, or combinations thereof, in comparison to a subject of a non-immunized control group of the same species.

In another aspect, the present invention concerns the immunogenic composition or combination vaccine or combination (or separated kit components) as herein described and claimed for use in a method of immunizing a subject comprising administering said immunogenic composition or combination vaccine or combination to such subject (or separated kit components).

In another aspect, the present invention concerns the immunogenic composition or combination vaccine or combination (or separated kit components) as herein described and claimed for use in a method of treating and/or preventing clinical signs caused by a PPV infection and/or a PRRS virus infection, preferably Porcine Reproductive and Respiratory Syndrome, preferably in swine, in a subject of need, the method comprising administering to the subject a therapeutically effective amount of said immunogenic composition or combination vaccine or combination (or separated kit components).

In another aspect, the present invention concerns the immunogenic composition or combination vaccine or combination (or separated kit components) as herein described and claimed for use in a method of reducing the reproductive failure in a subject in comparison to a subject of a non-immunized control group of the same species, the method comprising administering to the subject a therapeutically effective amount of said immunogenic composition or combination vaccine or combination (or separated kit components).

In another aspect, the present invention concerns the immunogenic composition or combination vaccine or combination (or separated kit components) as herein described and claimed for use in a method of reducing embryonic and fetal death in a subject in comparison to a subject of a non-immunized control group of the same species, the method comprising administering to the subject a therapeutically effective amount of said immunogenic composition or combination vaccine or combination (or separated kit components).

In another aspect, the present invention concerns the immunogenic composition or combination vaccine or combination (or separated kit components) as herein described and claimed for use in a method for active immunization of breeding pigs (sows and gilts) for protection of embryos and fetuses against porcine parvovirus infection, the method comprising administering to such pigs (sows and gilts) said immunogenic composition or combination vaccine or combination (or separated kit components).

In another aspect, the present invention concerns the immunogenic composition or combination vaccine or combination (or separated kit components) as herein described and claimed for the use as herein described and claimed, wherein said subject is selected from the group consisting of swine, cattle, cat and dog, preferably swine, more preferably sow and/or gilt.

In another aspect, the present invention concerns the immunogenic composition or combination vaccine or combination (or separated kit components) as herein described and claimed for the use as herein described and claimed, wherein the immunogenic composition or combination vaccine or combination (or separated kit components) is administered once or at two or more doses.

In another aspect, the present invention concerns the immunogenic composition or combination vaccine or combination (or separated kit components) as herein described and claimed for the use as herein described and claimed, wherein the immunogenic composition or combination vaccine or combination (or separated kit components) is administered intramuscularly.

In another aspect, the present invention concerns the immunogenic composition or combination vaccine or combination (or separated kit components) as herein described and claimed for the use as herein described and claimed, wherein the immunogenic composition or combination vaccine or combination (or separated kit components) is administered to gilts and/or sows, preferably to sows being at least 3 weeks of age, more preferably to sows before pregnancy, even more preferably to sows during pregnancy and lactation.

In another aspect, the present invention concerns the immunogenic composition or combination vaccine or combination (or separated kit components) as herein described and claimed for the use as herein described and claimed, wherein the immunogenic composition or combination vaccine or combination (or separated kit components) is safe for gilts and/or sows during pregnancy and lactation.

In another aspect, the present invention concerns the immunogenic composition or combination vaccine or combination (or separated kit components) as herein described and claimed for the use as herein described and claimed, wherein the immunogenic composition or combination vaccine or combination (or separated kit components) is safe for gilts and/or sows from 30 days of gestation, preferably from 40 days of gestation.

In another aspect, the present invention concerns the immunogenic composition or combination vaccine or combination (or separated kit components) as herein described and claimed for the use as herein described and claimed, wherein the immunogenic composition or combination vaccine or combination (or separated kit components) comprises 0.1 µg to 50 µg of the PPV VP2 antigen, preferably 0.5 µg to 10 µg of the PPV VP2 antigen, more preferably 1.0 µg to 10 µg of the PPV VP2 antigen, and/or 3.9 to 7.0 $\log_{10}TCID_{50}$ of the PRRS virus.

In another aspect, the present invention concerns the immunogenic composition or combination vaccine or combination (or separated kit components) as herein described and claimed for the use as herein described and claimed, wherein the immunogenic composition or combination vaccine or combination (or separated kit components) protects against a homologous and/or a heterologous challenge with PPV and/or protects against a homologous and/or a heterologous challenge with PRRS virus.

In another aspect, the present invention concerns the immunogenic composition or combination vaccine or combination (or separated kit components) as herein described and claimed for the use as herein described and claimed, wherein the immunogenic composition or combination vaccine or combination (or separated kit components) protects against a challenge with North American and/or European isolates of PPV and/or protects against a challenge with North American and/or European isolates of PRRS virus.

In another aspect, the present invention concerns the immunogenic composition or combination vaccine or combination (or separated kit components) as herein described and claimed for the use as herein described and claimed, wherein the immunogenic composition or combination vaccine or combination (or separated kit components) is cross-protective against North American and/or European isolates of PPV and/or is cross-protective against North American and/or European isolates of PRRS virus.

In another aspect, the present invention concerns the immunogenic composition or combination vaccine or combination (or separated kit components) as herein described and claimed for the use as herein described and claimed, wherein said method results in an improvement of at least one efficacy parameter selected from the group consisting of: reduced transient leukopenia and reproductive failure characterized by embryonic and/or fetal infection and death, or combinations thereof, in comparison to a subject of a non-immunized control group of the same species.

The term "treatment and/or prophylaxis" refers to the lessening of the incidence of the particular PPV and/or PRRSV infection in a herd or the reduction in the severity of clinical signs caused by or associated with the particular PPV and/or PRRSV infection. Thus, the term "treatment and/or prophylaxis" also refers to the reduction of the number of animals in a herd that become infected with the particular PPV and/or PRRSV (=lessening of the incidence of the particular PPV and/or PRRSV infection) or to the reduction of the severity of clinical signs normally associated with or caused by a PPV and/or PRRSV infection in a group of animals which animals have received an effective amount of the immunogenic composition or combination vaccine or combination as provided herein in comparison to a group of animals which animals have not received such the immunogenic composition or combination vaccine or combination.

The "treatment and/or prophylaxis" generally involves the administration of an effective amount of the immunogenic composition or combination vaccine or combination of the present invention to a subject or herd of subjects in need of or that could benefit from such a treatment/prophylaxis. The term "treatment" refers to the administration of the effective amount of the immunogenic composition or combination vaccine or combination once the subject or at least some animals of the herd is/are already infected with such PPV and/or PRRSV and wherein such animals already show some clinical signs caused by or associated with such PPV and/or PRRSV infection. The term "prophylaxis" refers to the administration of a subject prior to any infection of such subject with PPV and/or PRRSV or at least where such animal or none of the animals in a group of animals do not show any clinical signs caused by or associated with the infection by such PPV and/or PRRSV. The terms "prophylaxis" and "preventing" are used interchangeably in this application.

The term "an effective amount" as used herein means, but is not limited to an amount of antigen, that elicits or is able to elicit an immune response in a subject. Such effective amount is able to lessen the incidence of the particular PPV and/or PRRSV infection in a herd or to reduce the severity of clinical signs of the particular PPV and/or PRRSV infection.

Preferably, clinical signs are lessened in incidence or severity by at least 10%, more preferably by at least 20%, still more preferably by at least 30%, even more preferably by at least 40%, still more preferably by at least 50%, even more preferably by at least 60%, still more preferably by at least 70%, even more preferably by at least 80%, still more preferably by at least 90%, still more preferably by at least 95% and most preferably by 100% in comparison to subjects that are either not treated or treated with an immunogenic composition or combination vaccine or combination that was available prior to the present invention but subsequently infected by the particular PPV and/or PRRSV.

The term "clinical signs" as used herein refers to signs of infection of a subject from PPV and/or PRRSV. The clinical signs of infection depend on the pathogen selected. Examples for such clinical signs include but are not limited to reduced transient leukopenia and reproductive failure characterized by embryonic and/or fetal infection and death, or combinations thereof. Examples for clinical signs that are directly observable include reduced litter size, increased mummification of the embryo or fetus per litter, autolysation of the embryo or fetus, reduced size of the embryo or fetus, reduced weight of the embryo or fetus and the alike or combinations thereof. Further examples of such clinical signs include but are not limited to increased viremia, increased viral load within the targeted tissues and blood, increased transmission/shed spread of PPV to pen mates and the alike or combinations thereof.

Preferably, the clinical signs lessened in incidence or severity in a treated subject compared to subjects that are either not treated or treated with an immunogenic composition that was available prior to the present invention but subsequently infected by the particular PPV and/or PRRSV refer to a transient leukopenia and reproductive failure characterized by embryonic and/or fetal infection and death, or combinations thereof.

The term "in need" or "of need", as used herein means that the administration/treatment is associated with the boosting or improvement in health or clinical signs or any other positive medicinal effect on health of the animals (including its embryos or fetuses) which receive the immunogenic composition in accordance with the present invention.

The term "reducing" or "reduced" or "reduction" or lower" are used interchangeably in this application. The term "reduction" means, that the clinical sign is reduced by at least 10%, more preferably by at least 20%, still more preferably by at least 30%, even more preferably by at least 40%, still more preferably by at least 50%, even more preferably by at least 60%, still more preferably by at least 70%, even more preferably by at least 80%, even more preferably by at least 90%, still more preferably by at least 95% most preferably by 100% in comparison to subjects that are not treated (not immunized) but subsequently infected by the particular PPV and/or PRRSV.

In one aspect of the present invention the immunogenic composition or combination vaccine or combination (or separated kit components) as described and claimed herein is administered once. It is understood, that a single-dose is administered only once.

The dose volume per subject depends on the route of vaccination and the age of the subject. Preferably, the single-dose has a total volume between about 0.2 ml and 2.5 ml, more preferably between about 0.2 ml and 2.0 ml, even more preferably between about 0.2 ml and 1.75 ml, still more preferably between about 0.2 ml and 1.5 ml, even more preferably between about 0.4 ml and 1.25 ml, even more preferably between about 0.4 ml and 1.0 ml with a single 0.5 ml dose or 1.0 ml dose being the most preferred. Most preferred the single-dose has a total volume of 0.5 ml, 1 ml, 1.5 ml or 2 ml.

In one aspect of the present invention the immunogenic composition or combination vaccine or combination (or separated kit components) as described and claimed herein is administered at two or more doses.

However, the immunogenic composition or combination vaccine or combination can be administered at two or more doses, with a first dose being administered prior to the administration of a second (booster) dose. Preferably, the second dose is administered at least 15 days after the first dose. More preferably, the second dose is administered between 15 days and 40 days after the first dose. Even more preferably, the second dose is administered at least 17 days after the first dose. Still more preferably, the second dose is administered between 17 days and 30 days after the first dose. Even more preferably, the second dose is administered at least 19 days after the first dose. Still more preferably, the second dose is administered between 19 days and 25 days after the first dose. Most preferably the second dose is administered at least 21 days after the first dose. Even more preferably, the second dose is administered at about 21 days after the first dose or at 21 days after the first dose. In a preferred aspect of the two-time administration regimen, both the first and second doses of the immunogenic composition are administered in the same amount. Preferably, each dose is in the preferred amounts specified above, with a dose of 1 ml or 2 ml for the first and second dose being most preferred. In addition to the first and second dose regimen, an alternate embodiment comprises further subsequent doses. For example, a third, fourth, or fifth dose could be administered in these aspects. Preferably, subsequent third, fourth, and fifth dose regimens are administered in the same amount as the first dose, with the time frame between the doses being consistent with the timing between the first and second doses mentioned above. The above administration regimens are preferably applied for gilts only. Sows are preferably only administered the immunogenic composition or combination vaccine or combination as a single administration/single shot.

In one aspect of the present invention the subject is selected from the group consisting of swine, cattle, cat and dog.

Preferably, the subject is swine. It has to be understood that swine comprises female and male animals. Semen may contain PPV and, for that reason female and male breeding animals are encompassed by the wording "swine". Thus, the wording "swine" comprises male animals such as boars as well as female animals such as gilts and sows.

The term "gilt", as used herein, refers to a porcine, preferably a pig, before and during first gestation/pregnancy. In contrast, the term "sow", as used herein, refers to a porcine, preferably a pig, after first farrowing,—as a positive result of its first gestation/pregnancy.

The dose volume per subject depends on the route of vaccination and the age of the subject. Preferably, the total volume is between about 0.2 ml and 5 ml, more preferably between about 0.5 ml and 3.0 ml, even more preferably between about 1.0 ml and 2.5 ml, even more preferably between about 1.0 ml and 2.0 ml. Most preferred the volume is 1 ml, 1.5 ml, 2 ml or 2.5 ml per dose.

The immunogenic composition or combination vaccine or combination (or separated kit components) is, preferably, administered topically or systemically. Suitable routes of administration conventionally used are oral or parenteral administration, such as intranasal, intravenous, intradermal, transdermal, intramuscular, intraperitoneal, subcutaneous, as well as inhalation. However, depending on the nature and mode of action of a compound, the immunogenic composition may be administered by other routes as well. For example, such other routes include intracutaneously, intravenously, intravascularly, intraarterially, intraperitnoeally, intrathecally, intratracheally, intracutaneously, intracardially, intralobally, intralobarly, intramedullarly, intrapulmonarily, intrarectally, and intravaginally. However, more preferred the immunogenic composition or combination vaccine or combination is administered subcutaneously or intramuscularly. Most preferred the immunogenic composition or combination vaccine or combination is administered intramuscular.

The following clauses are described herein:

1. An immunogenic composition or a combination vaccine or a combination comprising:
   a) at least one porcine parvo virus (PPV) antigen, wherein the at least one PPV antigen is any antigen contained in PPV, and
   b) at least one porcine reproductive and respiratory syndrome (PRRS) virus antigen, wherein the at least one PRRS virus antigen is any antigen contained in PRRS virus.

2. The immunogenic composition or combination vaccine or combination according to clause 1, wherein the PPV is selected from the group consisting of: live attenuated/modified live PPV virus, killed/inactivated PPV virus (e.g., PORCILIS® Parvo (Intervet, Inc.)), killed/inactivated PPV strain 014, German field isolates of Porcine parvovirus PPV-27a and PPV-143a and Porcine parvovirus vaccine viruses PPV-NADL-2 and PPV-IDT (MSV).

3. The immunogenic composition or combination vaccine or combination according to any one of clauses 1 to 2, wherein the at least one PPV antigen is one or more PPV subunit(s).

4. The immunogenic composition or combination vaccine or combination according to any one of clauses 1 to 3, wherein the at least one PPV subunit(s) is PPV viral protein 2 (VP2).

5. The immunogenic composition or combination vaccine or combination according to clause 4, wherein the PPV VP2 is the only PPV antigen.

6. The immunogenic composition or combination vaccine or combination according to any one of clauses 4 to 5, wherein the PPV VP2 has:
   at amino acid position 228 a glutamic acid residue or a glutamate residue, and/or
   at amino acid position 414 a serine residue, and/or
   at amino acid position 419 a glutamine residue, and/or
   at amino acid position 436 a threonine residue,
wherein the numbering of the amino acid positions refers to the amino acid sequence of wild type PPV VP2.

7. The immunogenic composition or combination vaccine or combination according to clause 6, wherein the PPV VP2 further has:
   at amino acid position 25 an isoleucine residue, and/or
   at amino acid position 36 a serine residue, and/or
   at amino acid position 37 an isoleucine residue.

8. The immunogenic composition or combination vaccine or combination according to any one of clauses 6 to 7, wherein the numbering of the amino acid positions refers to the amino acid sequence as shown in SEQ ID NO:1.

9. The immunogenic composition or combination vaccine or combination according to any one of clauses 4 to 8, wherein the PPV VP2 is a recombinant PPV VP2.

10. The immunogenic composition or combination vaccine or combination according to clause 9, wherein the PPV VP2 is a recombinant baculovirus expressed PPV VP2.

11. The immunogenic composition or combination vaccine or combination according to any one of clauses 4 to 10, wherein the PPV VP2 comprises or consists of an amino acid sequence having at least 90% sequence identity with the amino acid sequence of SEQ ID NO:1, SEQ ID NO:2 and/or SEQ ID NO:5 to 16.

12. The immunogenic composition or combination vaccine or combination according to clause 11, wherein the PPV VP2 comprises or consists of an amino acid sequence having at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity with the amino acid sequence of SEQ ID NO:1, SEQ ID NO:2 and/or SEQ ID NO:5 to 16.

13. The immunogenic composition or combination vaccine or combination according to clause 12, wherein the PPV VP2 comprises or consists of the amino acid sequence of SEQ ID NO:1, SEQ ID NO:2 or SEQ ID NO:5 to 16 or comprises or consists of any fragment having at least 210, at least 250 or at least 300 contiguous amino acid residues from SEQ ID NO:1, SEQ ID NO:2 or SEQ ID NO:5 to 16.

14. The immunogenic composition or combination vaccine or combination according to clause 13, wherein the PPV VP2 comprises or consists of the amino acid sequence of SEQ ID NO:1, SEQ ID NO:2 or SEQ ID NO:5 to 16.

15. The immunogenic composition or combination vaccine or combination according to any one of clauses 4 to 14, wherein the PPV VP2 is encoded by a nucleotide sequence encoding an amino acid sequence having at least 90% sequence identity with the amino acid sequence of SEQ ID NO:1, SEQ ID NO:2 and/or SEQ ID NO:5 to 16.

16. The immunogenic composition or combination vaccine or combination according to clause 15, wherein the PPV VP2 is encoded by a nucleotide sequence encoding an amino acid sequence having at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity with the amino acid sequence of SEQ ID NO:1, SEQ ID NO:2 and/or SEQ ID NO:5 to 16.

17. The immunogenic composition or combination vaccine or combination according to clause 16, wherein the PPV VP2 is encoded by a nucleotide sequence encoding an amino acid sequence of SEQ ID NO:1, SEQ ID NO:2 or SEQ ID NO:5 to 16.

18. The immunogenic composition or combination vaccine or combination according to any one of clauses 1 to 16, wherein the PRRS virus is selected from the group consisting of: PRRS virus genotype 1, PRRS virus genotype 2, PRRS virus genotype 1 comprising a genome encoded by a nucleotide sequence having at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, at least 99.9%, or 100% identity with the nucleic acid sequence of SEQ ID NO:17 (Lelystad wild-type sequence), PRRS virus genotype 2 comprising a genome encoded by a nucleotide sequence having at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, at least 99.9%, or 100% identity with the nucleic acid sequence of SEQ ID NO:18 (VR2332 wild-type sequence).

19. The immunogenic composition or combination vaccine or combination according to clause 18, wherein the PRRS virus is selected from the group consisting of: live attenuated/modified live PRRS virus, live attenuated/modified live PRRS virus type 1 genotype (e.g. PORCILIS® PRRS (Intervet, Inc.), Unistrain PRRS, Amervac PRRS), live attenuated/modified live PRRS virus type 2 genotype (e.g. INGELVAC® PRRS MLV, FOSTERA® PRRS (Zoetis)), live attenuated/modified live PRRS virus strain 94881 [(genotype 1), REPROCYC® PRRS EU], killed/inactivated PRRS virus, killed/inactivated PRRS virus type 1 genotype (e.g., Progressis), killed/inactivated PRRS virus type 2 genotype, Lelystad virus strain (CDI-NL-2.91, Institut Pasteur, Paris, France, deposit number I-1102), PRRS virus subunit(s), or other strains such as those deposited under the Accession Numbers ECACC 04102703, ECACC 04102702, ECACC 04102704, CNCM Accession No. 1-1140, CNCM Accession No 1-1387, CNCM Accession No 1-1388, ATCC VR 2332, VR 2385, VR 2386, VR 2429, VR 2474, and VR 2402; CNCM 1-1102, CNCM 1-1140, CNCM 1-1387, CNCM 1-1388, or ECACC V93070108, North American PRRS virus pT7P129A (ATCC Accession No. 203488), ATCC deposit VR-2332, ATCC deposit VR-2368; ATCC VR-2495; ATCC VR 2385, ATCC VR 2386, ATCC VR 2429, ATCC VR 2474, and ATCC VR 2402.

20. The immunogenic composition or combination vaccine or combination according to any one of clauses 1 to 19, wherein the at least one PPV antigen is one or more PPV subunit(s), preferably wherein the at least one PPV antigen is PPV viral protein 2 (VP2), wherein more preferably the PPV VP2 is the only PPV antigen, and wherein the at least one PRRS virus antigen is live attenuated/modified live PRRS virus, preferably live attenuated/modified live PRRS virus type 1 genotype (e.g., PORCILIS® PRRS (Intervet, Inc.), Unistrain PRRS, Amervac PRRS), more preferably live attenuated/modified live PRRS virus strain 94881 [(genotype 1), REPROCYC® PRRS EU] and live attenuated/modified live PRRS virus type 2 genotype (e.g. INGELVAC® PRRS MLV, FOSTERA® PRRS (Zoetis)).

21. The immunogenic composition or combination vaccine or combination according to any one of clauses 1 to 20, wherein the immunogenic composition or combination vaccine or combination is formulated for a single-dose administration or a two-dose administration.

22. The immunogenic composition or combination vaccine or combination according to any one of clauses 1 to 21, wherein the immunogenic composition or combination vaccine or combination is administered intramuscularly.

23. The immunogenic composition or combination vaccine or combination according to any one of clauses 1 to 22, wherein the immunogenic composition or combination vaccine or combination is safe for gilts and/or sows during pregnancy and lactation.

24. The immunogenic composition or combination vaccine or combination of according to clause 23, wherein the immunogenic composition or combination vaccine or combination is safe for gilts and/or sows from 30 days of gestation, preferably from 40 days of gestation.

25. The immunogenic composition or combination vaccine or combination according to any one of clauses 1 to 24, wherein the immunogenic composition or combination vaccine or combination further comprises at least one pharmaceutically acceptable carrier.

26. The immunogenic composition or combination vaccine or combination according to clause 25, wherein the at least one pharmaceutically acceptable carrier is a carbomer.

27. The immunogenic composition or combination vaccine or combination according to any one of clauses 4 to 26, wherein the immunogenic composition or combination vaccine or combination comprises 0.1 µg to 50 µg of the PPV VP2 antigen, preferably 0.5 µg to 10 µg of the PPV VP2 antigen, more preferably 1.0 µg to 10 µg of the PPV VP2 antigen, and/or 3.9 to 7.0 $\log_{10}TCID_{50}$ of the PRRS virus.

28. The immunogenic composition or combination according to any one of clauses 1 to 27, wherein the immunogenic composition or combination is a vaccine.

29. The immunogenic composition or combination vaccine or combination of according to any one of clauses 1 to 28, wherein the immunogenic composition or combination vaccine or combination protects against a homologous and/or a heterologous challenge with PPV and/or a homologous and/or a heterologous challenge with PRRS virus.

30. The immunogenic composition or combination vaccine or combination according to any one of clauses 1 to 29, wherein the immunogenic composition or combination vaccine or combination protects against a challenge with North American and/or European isolates of PPV and/or against a challenge with North American and/or European isolates of PRRS virus.

31. The immunogenic composition or combination vaccine or combination of according to any one of clauses 1 to 30, wherein the immunogenic composition or combination vaccine or combination is cross-protective against North American and/or European isolates of PPV and/or is cross-protective against North American and/or European isolates of PRRS virus.

32. The immunogenic composition or combination vaccine or combination according to any one of clauses 1 to 31, wherein the immunogenic composition or combination vaccine or combination is effective in the treatment and/or prophylaxis of clinical signs caused by a PPV infection and/or a PRRS virus infection in a subject of need.

33. The immunogenic composition or combination vaccine or combination according to any one of clauses 1 to 31, wherein the at least one porcine parvovirus (PPV) antigen and the at least one porcine reproductive and respiratory syndrome (PRRS) virus antigen are contained together in one single container or are spatially separated from each other, preferably are contained in two or more separate containers.

34. A kit comprising the immunogenic composition or combination vaccine or combination according to any one of clauses 1 to 33.

35. The kit according to clause 34, wherein the at least one porcine parvo virus (PPV) antigen and the at least one porcine reproductive and respiratory syndrome (PRRS) virus antigen are contained separately from each other in two or more separate containers, preferably both independently from each other either in lyophilized or in frozen form, and wherein the kit further comprises an instruction manual for mixing the spatially separated at least one PPV antigen and at least one PRRS virus antigen, wherein preferably such instruction manual contains directions to combine the contents of the container(s) containing the at least one PPV antigen with the contents of the container(s) containing the at least one PPRS virus antigen, wherein more preferably the liquid contents of the container(s) containing the at least one PPV antigen are used as a diluent for the lyophilized contents of the container(s) containing the at least one PPRS virus antigen.

36. The kit according to any one of clauses 34 to 35, wherein the kit further comprises directions for the treatment and/or prophylaxis of diseases in swine and/or further comprises directions for the treatment and/or prophylaxis of PPV infections and/or PRRS virus infections, preferably such kit further comprises directions for the associated use of the PPV component and the PRRSV component of the immunogenic composition or combination vaccine or combination according to any one of clauses 1 to 33.

37. Use of the immunogenic composition or combination vaccine or combination according to any one of clauses 1 to 33 or the kit according to any one of clauses 34 to 36 for the preparation of a medicament, preferably of a vaccine.

38. The use according to clause 37 for the preparation of a medicament for the treatment and/or prevention of an infection with PPV and/or PRRS virus, the reduction, prevention or treatment of clinical signs caused by an infection with PPV and/or PRRS virus, or for the treatment and/or prevention of a disease caused by an infection with PPV and/or PRRS virus.

39. A method of immunizing a subject comprising administering to such subject an immunogenic composition or combination vaccine or combination according to any one of clauses 1 to 33.

40. A method of treating and/or preventing clinical signs caused by a PPV infection and/or a PRRS virus infection, preferably Porcine Reproductive and Respiratory Syndrome, preferably in swine, in a subject of need, the method comprising administering to the subject a therapeutically effective amount of an immunogenic composition or combination vaccine or combination according to any one of clauses 1 to 33.

41. A method of reducing the reproductive failure in a subject in comparison to a subject of a non-immunized control group of the same species, the method comprising administering to the subject a therapeutically effective amount of an immunogenic composition or combination vaccine or combination according to any one of clauses 1 to 33.

42. A method of reducing embryonic and fetal death in a subject in comparison to a subject of a non-immunized control group of the same species, the method comprising administering to the subject a therapeutically effective amount of an immunogenic composition or combination vaccine or combination according to any one of clauses 1 to 33.

43. The method according to any one of clauses 39 to 42, wherein said subject is selected from the group consisting of swine, cattle, cat and dog, preferably swine, more preferably sow and/or gilt.

44. The method according to any one of clauses 39 to 43, wherein the immunogenic composition or combination vaccine or combination is administered once or at two or more doses.

45. The method according to any one of clauses 39 to 44, wherein the immunogenic composition or combination vaccine or combination is administered intramuscularly.

46. The method according to any one of clauses 39 to 45, wherein the immunogenic composition or combination vaccine or combination is administered to gilts and/or sows, preferably to sows being at least 3 weeks of age, more preferably to sows before pregnancy, even more preferably to sows during pregnancy and lactation.

47. The method according to any one of clauses 39 to 46, wherein the immunogenic composition or combination vaccine or combination is safe for gilts and/or sows during pregnancy and lactation.

48. The method according to any one of clauses 39 to 47, wherein the immunogenic composition or combination vaccine or combination is safe for sows and/or gilts from 30 days of gestation, preferably from 40 days of gestation.

49. The method according to any one of clauses 39 to 48, wherein the immunogenic composition or combination vaccine or combination comprises 0.1 µg to 50 µg of the PPV VP2 antigen, preferably 0.5 µg to 10 µg of the PPV VP2 antigen, more preferably 1.0 µg to 10 µg of the PPV VP2 antigen, and/or 3.9 to 7.0 $\log_{10}TCID_{50}$ of the PRRS virus.

50. The method according to any one of clauses 39 to 49, wherein the immunogenic composition or combination vaccine or combination protects against a homologous and/or a heterologous challenge with PPV and/or a homologous and/or a heterologous challenge with PRRS virus.

51. The method according to any one of clauses 39 to 50, wherein the immunogenic composition or combination vaccine or combination protects against a challenge with North American and/or European isolates of PPV and/or against a challenge with North American and/or European isolates of PRRS virus.

52. The method according to any one of clauses 39 to 51, wherein the immunogenic composition or combination vaccine or combination is cross-protective against North American and/or European isolates of PPV and/or is cross-protective against North American and/or European isolates of PRRS virus.

53. The method according to any one of clauses 39 to 52, wherein said method results in an improvement of at least one efficacy parameter selected from the group consisting of: reduced transient leukopenia and reproductive failure characterized by embryonic and/or fetal infection and death, or combinations thereof, in comparison to a subject of a non-immunized control group of the same species.

54. The method according to any one of clauses 39 to 53, wherein the at least one porcine parvovirus (PPV) antigen and the at least one porcine reproductive and respiratory syndrome (PRRS) virus antigen are administered to the subject simultaneously, preferably separately simultaneously at the same or different administration sites, sequentially (in any order), and/or in a chronologically staggered fashion.

55. The method according to any one of clauses 39 to 54 for active immunization of breeding pigs (sows and gilts) for protection of embryos and fetuses against porcine parvovirus infection comprising administering to such pigs (sows and gilts) an immunogenic composition or combination vaccine or combination according to any one of clauses 1 to 33.

56. The immunogenic composition or combination vaccine or combination according to any one of clauses 1 to 33 for use in a method of immunizing a subject comprising administering said immunogenic composition or combination vaccine or combination to such subject.

57. The immunogenic composition or combination vaccine or combination according to any one of clauses 1 to 33 for use in a method of treating and/or preventing clinical signs caused by a PPV infection and/or a PRRS virus infection, preferably Porcine Reproductive and Respiratory Syndrome, preferably in swine, in a subject of need, the method comprising administering to the subject a therapeutically effective amount of said immunogenic composition or combination vaccine or combination.

58. The immunogenic composition or combination vaccine or combination according to any one of clauses 1 to 33 for use in a method of reducing the reproductive failure in a subject in comparison to a subject of a non-immunized control group of the same species, the method comprising administering to the subject a therapeutically effective amount of said immunogenic composition or combination vaccine or combination.

59. The immunogenic composition or combination vaccine or combination according to any one of clauses 1 to 33 for use in a method of reducing embryonic and fetal death in a subject, in comparison to a subject of a non-immunized control group of the same species, the method comprising administering to the subject a therapeutically effective amount of said immunogenic composition or combination vaccine or combination.

60. The immunogenic composition or combination vaccine or combination according to of any one of clauses 1 to 33 for the use according to any one of clauses 56 to 59, wherein said subject is selected from the group consisting of swine, cattle, cat and dog, preferably swine, more preferably sow and/or gilt.

61. The immunogenic composition or combination vaccine or combination according to of any one of clauses 1 to 33 for the use according to any one of clauses 56 to 60, wherein the immunogenic composition or combination vaccine or combination is administered once or at two or more doses.

62. The immunogenic composition or combination vaccine or combination according to of any one of clauses 1 to 33 for the use according to any one of clauses 56 to 61, wherein the immunogenic composition or combination vaccine or combination is administered intramuscularly.

63. The immunogenic composition or combination vaccine or combination according to of any one of clauses 1 to 33 for the use according to any one of clauses 56 to 62, wherein the immunogenic composition or combination vaccine or combination is administered to gilts and/or sows, preferably to sows being at least 3 weeks of age, more preferably to sows before pregnancy, even more preferably to sows during pregnancy and lactation.

64. The immunogenic composition or combination vaccine or combination according to of any one of clauses 1 to 33 for the use according to any one of clauses 56 to 63, wherein the immunogenic composition or combination vaccine or combination is safe for gilts and/or sows during pregnancy and lactation.

65. The immunogenic composition or combination vaccine or combination according to of any one of clauses 1 to 33 for the use according to any one of clauses 56 to 64, wherein the immunogenic composition or combination vaccine or combination is safe for gilts and/or sows from 30 days of gestation, preferably from 40 days of gestation.

66. The immunogenic composition or combination vaccine or combination according to of any one of clauses 1 to 33 for the use according to any one of clauses 56 to 65, wherein the immunogenic composition or combination vaccine or combination comprises 0.1 µg to 50 µg of the PPV VP2 antigen, preferably 0.5 µg to 10 µg of the PPV VP2 antigen, more preferably 1.0 µg to 10 µg of the PPV VP2 antigen, and/or 3.9 to 7.0 $\log_{10}TCID_{50}$ of the PRRS virus.

67. The immunogenic composition or combination vaccine or combination according to of any one of clauses 1 to 33 for the use according to any one of clauses 56 to 66, wherein the immunogenic composition or combination vaccine or combination protects against a homologous and/or a heterologous challenge with PPV and/or protects against a homologous and/or a heterologous challenge with PRRS virus.

68. The immunogenic composition or combination vaccine or combination according to of any one of clauses 1 to 33 for the use according to any one of clauses 56 to 67, wherein the immunogenic composition or combination vaccine or combination protects against a challenge with North American and/or European isolates of PPV and/or protects against a challenge with North American and/or European isolates of PRRS virus.

69. The immunogenic composition or combination vaccine or combination according to of any one of clauses 1 to 33 for the use according to any one of clauses 56 to 68, wherein the immunogenic composition or combination vaccine or combination is cross-protective against North American and/or European isolates of PPV and/or is cross-protective against North American and/or European isolates of PRRS virus.

70. The immunogenic composition or combination vaccine or combination according to of any one of clauses 1 to 33 for the use according to any one of clauses 56 to 69, wherein said method results in an improvement of at least one efficacy parameter selected from the group consisting of: transient leukopenia and reproductive failure characterized by embryonic and/or fetal infection and death, or combinations thereof, in comparison to a subject of a non-immunized control group of the same species.

71. The immunogenic composition or combination vaccine or combination according to of any one of clauses 1 to 33 for the use according to any one of clauses 56 to 70, wherein the at least one porcine parvovirus (PPV) antigen and the at least one porcine reproductive and respiratory syndrome (PRRS) virus antigen are administered to the subject simultaneously, preferably separately simultaneously at the same or different administration sites, sequentially (in any order), and/or in a chronologically staggered fashion.

72. The immunogenic composition or combination vaccine or combination according to of any one of clauses 1 to 33 for use in a method for active immunization of breeding pigs (sows and gilts) for protection of embryos and fetuses against porcine parvovirus infection comprising administering said immunogenic composition or combination vaccine or combination to such pigs (sows and gilts).

Second Consideration of the Present Invention

In one aspect, the present invention concerns a method of producing an immunogenic composition comprising a recombinant protein, wherein the method comprises the steps in the following order:
(i) providing/obtaining a mixture comprising
  a first liquid,
  recombinant protein and/or quaternary structures composed of a plurality of said recombinant protein, and
  a vector comprising a nucleic acid sequence encoding said recombinant protein;
(ii) adding a second liquid to the mixture of step (i), wherein the second liquid is different from the first liquid;
(iii) washing, and optionally finally concentrating, the recombinant protein and/or quaternary structures composed of a plurality of said recombinant protein in the mixture by further adding additional second liquid to the mixture resulting from step (ii) and removing a portion of the first and/or second liquid from such combined mixture;
(iv) inactivating the vector by adding an inactivating agent to the mixture resulting from step (iii);
(v) neutralizing the inactivating agent by adding a neutralizing agent to the mixture resulting from step (iv).

For purposes of the present invention, a "first liquid" refers to liquid, aqueous, or fluid media typically used in combination with cells, antigens, immunogenic compositions, vaccines, and the like. Preferably, the first liquid comprises media from an antigenic composition; more preferably, the first liquid comprises or preferably consists of cell culture media used for the production of recombinant proteins in cultivated host cells. Said cultivated host cells can be bacteria, yeasts, insect cells, animal cells, and mammalian cells, with insect and mammalian cells being particularly preferred. Thus, the first liquid may comprise or consist of media for the cultivation of bacteria, yeast, insect cells, animal cells or mammalian cells. Preferably, the cell media is serum free cell media, and most preferably the culture media is Excell 420 serum free media, when insect cells are used.

A "second liquid", for purposes of the present invention, refers to any liquid normally used in combination with cells, antigen, immunogenic compositions, vaccines, and the like, which is different from the first liquid. Preferably, the second liquid is an aqueous solution, even more preferably a pharmaceutically acceptable solution, and even more preferably a buffer, such as a saline or phosphate buffer and the like. Most preferably, the second liquid is characterized by not being virucidal to any live virus or live bacteria, when the live virus or live bacteria is cultivated in or stored in such a liquid.

"Portion", for purposes of the present invention, refers to any amount which does not encompass the entire amount. For example, a portion of liquid would be anything less than 100% of the volume of the liquid, such as 90% of the liquid, 80% of the liquid, 70% of the liquid, and all amounts between more than 0% and less than 100%.

"Recombinant protein", for purposes of the present invention, refers to any recombinant protein, preferably to a PPV VP2 protein, more preferably comprising or consisting of a sequence having at least 70%, at least 75%, at least 80%, at least 85%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, at least 99.9%, or 100% sequence identity with the sequence of SEQ ID NO:1, SEQ ID NO:2 and/or SEQ ID NOS 5 to 16.

"Quaternary structures" as well as "quaternary structures composed of a plurality of said recombinant protein", for purposes of the present invention, refers to a three-dimensional arrangement of a plurality of said recombinant protein, such as virus-like particles and/or homotrimers.

"Vector" as well as "vector comprising a nucleic acid sequence encoding said recombinant protein", for purposes of the present invention, refers to suitable expression vector, preferably a baculovirus expression vector, which is in turn used to transfect, or in case of a baculovirus expression vector to infect, a host cell to produce the protein or polypeptide encoded by the DNA.

Vectors and methods for making and/or using vectors (or recombinants) for expression can be by or analogous to the methods disclosed in: U.S. Pat. Nos. 4,603,112, 4,769,330, 5,174,993, 5,505,941, 5,338,683, 5,494,807, 4,722,848, 5,942,235, 5,364,773, 5,762,938, 5,770,212, 5,942,235, 382.425, PCT publications WO 94/16716, WO 96/39491, WO 95/30018; Paoletti, "Applications of pox virus vectors to vaccination: An update, "PNAS USA 93: 11349-11353, October 1996; Moss, "Genetically engineered poxviruses for recombinant gene expression, vaccination, and safety," PNAS USA 93: 11341-11348, October 1996; Smith et al., U.S. Pat. No. 4,745,051 (recombinant baculovirus); Richardson, C. D. (Editor), Methods in Molecular Biology 39, "Baculovirus Expression Protocols" (1995 Humana Press Inc.); Smith et al., "Production of Human Beta Interferon in Insect Cells Infected with a Baculovirus Expression Vector", Molecular and Cellular Biology, December, 1983, Vol. 3, No. 12, p. 2156-2165; Pennock et al., "Strong and Regulated Expression of Escherichia coli B-Galactosidase in Infect Cells with a Baculovirus vector, "Molecular and Cellular Biology March 1984, Vol. 4, No. 3, p. 406; EPAO 370 573; U.S. application No. 920,197, filed Oct. 16, 1986; EP Patent publication No. 265785; U.S. Pat. No. 4,769,331 (recombinant herpesvirus); Roizman, "The function of herpes simplex virus genes: A primer for genetic engineering of novel vectors," PNAS USA 93:11307-11312, October 1996; Andreansky et al., "The application of genetically engineered herpes simplex viruses to the treatment of experimental brain tumors," PNAS USA 93: 11313-11318, October 1996; Robertson et al., "Epstein-Barr virus vectors for gene delivery to B lymphocytes", PNAS USA 93: 11334-11340, October 1996; Frolov et al., "Alphavirus-based expression vectors: Strategies and applications," PNAS USA 93: 11371-11377, October 1996; Kitson et al., J. Virol. 65, 3068-3075, 1991; U.S. Pat. Nos. 5,591,439, 5,552,143; WO 98/00166; allowed U.S. application Ser. Nos. 08/675, 556, and 08/675,566 both filed Jul. 3, 1996 (recombinant adenovirus); Grunhaus et al., 1992, "Adenovirus as cloning vectors," Seminars in Virology (Vol. 3) p. 237-52, 1993; Ballay et al. EMBO Journal, vol. 4, p. 3861-65, Graham, Tibtech 8, 85-87, April, 1990; Prevec et al., J. Gen Virol. 70, 42434; PCT WO 91/11525; Felgner et al. (1994), J. Biol. Chem. 269, 2550-2561, Science, 259: 1745-49, 1993; and McClements et al., "Immunization with DNA vaccines encoding glycoprotein D or glycoprotein B, alone or in combination, induces protective immunity in animal models of herpes simplex virus-2 disease", PNAS USA 93: 11414-11420, October 1996; and U.S. Pat. Nos. 5,591,639, 5,589, 466, and 5,580,859, as well as WO 90/11092, WO93/19183, WO94/21797, WO95/11307, WO95/20660; Tang et al., Nature, and Furth et al., Analytical Biochemistry, relating to DNA expression vectors, inter alia. See also WO 98/33510; Ju et al., Diabetologia, 41: 736-739, 1998 (lentiviral expression system); Sanford et al., U.S. Pat. No. 4,945,050; Fischbach et al. (Intracel); WO 90/01543; Robinson et al., Seminars in Immunology vol. 9, pp. 271-283 (1997), (DNA vector systems); Szoka et al., U.S. Pat. No. 4,394,448 (method of inserting DNA into living cells); McCormick et al., U.S. Pat. No. 5,677,178 (use of cytopathic viruses); and U.S. Pat. No. 5,928,913 (vectors for gene delivery); as well as other documents cited herein.

Preferred cells are those susceptible for infection with an appropriate recombinant viral vector, containing a recombinant protein DNA and expressing the recombinant protein. Preferably the cells are insect cells, and more preferably, they include the insect cells sold under the trademark SF+insect cells (Protein Sciences Corporation, Meriden, Conn.). Preferred cell cultures have a cell count between about $0.3$-$2.0\times10^6$ cells/mL, more preferably from about $0.35$-$1.9\times10^6$ cells/mL, still more preferably from about $0.4$-$1.8\times10^6$ cells/mL, even more preferably from about $0.45$-$1.7\times10^6$ cells/mL, and most preferably from about $0.5$-$1.5\times10^6$ cells/mL.

Preferred viral vectors include baculovirus such as BACULOGOLD® (BD Biosciences Pharmingen, San Diego, Calif.), in particular provided that the production cells are insect cells. Although the baculovirus expression system is preferred, it is understood by those of skill in the art that other expression systems, including those described above will work for purposes of the present invention, namely the expression of recombinant protein.

Appropriate growth media will also be determinable by those of skill in the art with a preferred growth media being serum-free insect cell media such as Excell 420 (JRH Biosciences, Inc., Lenexa, Kans.) and the like.

The recombinant viral vector containing the recombinant protein DNA sequences has a preferred multiplicity of infection (MOI) of between about 0.03-1.5, more preferably from about 0.05-1.3, still more preferably from about 0.09-1.1, and most preferably from about 0.1-1.0, when used for the infection of the susceptible cells. Preferably the MOIs mentioned above relates to one mL of cell culture fluid. Preferably, the method described herein comprises the infection of 0.35-1.9×10$^6$ cells/mL, still more preferably of about 0.4-1.8×10$^6$ cells/mL, even more preferably of about 0.45-1.7×10$^6$ cells/mL, and most preferably of about 0.5-1.5×10$^6$ cells/mL with a recombinant viral vector containing a recombinant protein DNA and expressing the recombinant protein having a MOI (multiplicity of infection) of between about 0.03-1.5, more preferably from about 0.05-1.3, still more preferably from about 0.09-1.1, and most preferably from 0.1-1.0.

The portion of the first liquid can be removed from the combined mixture of step (iii) comprising the recombinant protein by a filtration step utilizing a filter. However, any other method known to a person skilled in the art can be used to remove the portion of any liquid, including the first and, whenever applicable, a portion of the second liquid from the combined mixture of step (iii). Such method for instance includes but is not limited to centrifugation and/or chromatography. However, filtration is most preferred. A preferred filtration method to remove the said portion of the first liquid, or any other liquid, whenever applicable, comprises ultra- and/or diafiltration. Ultra- and diafiltration are standard methods known to a person skilled in the art, described for example in detail in *Protein Purification Methods—A Practical Approach*—editors: E. L. V. Harris and S. Angel, Oxford University Press 1995 (the contents and teachings of which are hereby incorporated by reference). In particular, in Chapter 3 of that textbook, several methods and types of equipment are described, all of which can be used by an ordinary person skilled in the art in an exemplary manner for the purpose of the present invention.

"Inactivating agent", for purposes of the present invention, refers to any agent that can be used in any conventional inactivation method. Inactivation can be performed by chemical and/or physical treatments which are known to the person skilled in the art. Preferred inactivating agents include cyclized binary ethylenimine (BEI) including a solution of 2-bromoethyleneamine hydrobromide (BEA), which has been cyclized to binary ethylenimine (BEI). Preferred further chemical inactivation agents comprise but are not limited to Triton X-100, Sodium deoxycholate, Cetyltrimethylammonium bromide, β-Propiolactone, Thimerosal, Phenol and Formaldehyde (Formalin).

"Neutralizing agent", for purposes of the present invention, refers to any agent capable of neutralizing the inactivating agents as herein described such that the inactivating agent is no longer capable of inactivating the vector. The agent that neutralizes the inactivating agent is preferably sodium thiosulfate, sodium bisulfite and the like.

In another aspect, the present invention concerns a method as herein described and claimed, wherein the mixture of step (i) is obtainable by a procedure comprising the steps of:

a) permitting infection of susceptible cells in culture with a vector comprising a nucleic acid sequence encoding said recombinant protein and/or quaternary structures composed of a plurality of said recombinant protein, wherein said recombinant protein and/or quaternary structures composed of a plurality of said recombinant protein is expressed by said vector, b) thereafter recovering the recombinant protein and/or quaternary structures composed of a plurality of said recombinant protein from the cell culture, wherein preferably cell debris is separated from the recombinant protein and/or quaternary structures composed of a plurality of said recombinant protein via a separation step, preferably including a micro filtration through at least one filter, more preferably two filters, wherein the at least one filter preferably has a pore size larger than the recombinant protein and/or quaternary structures composed of a plurality of said recombinant protein, in particular has a pore size of about 0.1 μm to about 4 μm.

In another aspect, the present invention concerns a method as herein described and claimed, wherein the cell culture in step (a) is maintained at 27±2° C., preferably while the recombinant protein and/or quaternary structures composed of a plurality of said recombinant protein is expressed by said vector, and/or wherein the recovering in step (b) occurs 6 to 8 days, preferably 8 days, after inoculation of the cells with the vector.

In another aspect, the present invention concerns a method as herein described and claimed, wherein the separation step includes or consists of:
  a micro filtration through at least one filter having a pore size of about 2 μm to about 4 μm, and/or
  a micro filtration through at least one filter having a pore size of about 0.1 μm to about 0.8 μm.

In another aspect, the present invention concerns a method as herein described and claimed, wherein said first liquid comprises a portion of cell culture medium or consists of cell culture medium, and wherein the cell culture medium preferably is insect cell culture medium.

In another aspect, the present invention concerns a method as herein described and claimed, wherein said recombinant protein is selected from the group consisting of:
  a PPV VP2 protein preferably comprising or consisting of a sequence having at least 70%, at least 75%, at least 80%, at least 85%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, at least 99.9%, or 100% sequence identity with the sequence of SEQ ID NO:1, SEQ ID NO:2 and/or SEQ ID NOS: 5 to 16.

In another aspect, the present invention concerns a method as herein described and claimed, wherein said quaternary structures composed of a plurality of said recombinant protein are virus-like particles or wherein said quaternary structures composed of a plurality of said recombinant protein are homotrimers.

In another aspect, the present invention concerns a method as herein described and claimed, wherein the vector is a recombinant virus, preferably baculovirus, and/or wherein the nucleic acid sequence is a DNA sequence.

In another aspect, the present invention concerns a method as herein described and claimed, wherein the vector comprising a nucleic acid encoding said recombinant protein and/or quaternary structures composed of a plurality of said recombinant protein is a recombinant baculovirus, wherein said baculovirus comprises a DNA sequence encoding said recombinant protein and/or quaternary structures composed of a plurality of said recombinant protein.

In another aspect, the present invention concerns a method as herein described and claimed, wherein in step (iii) said recombinant protein and/or said quaternary structures composed of a plurality of said recombinant protein is washed with at least 2×, preferably from 2× to 3×, of second liquid, and optionally finally concentrated, in comparison to the original volume of said recombinant protein and/or said quaternary structures composed of a plurality of said recombinant protein in the mixture of step (i). More preferably, in step (iii) such washing step(s), i.e. the process of diafiltration, is performed at a temperature of lower than 37° C., more preferably at a temperature of lower than 30° C., even more preferably at a temperature of lower than 20° C., even more preferably at a temperature of lower than 10° C., such as for instance at a temperature between 4° C. and 29° C., for instance 27° C. or 4° C. Thereby, the degree of precipitation (aggregation) is significantly reduced.

In another aspect, the present invention concerns a method as herein described and claimed, wherein in step (iii) the portion of the first and/or second liquid is removed from the mixture by filtration, wherein preferably a filter or a hollow filter is utilized comprising a semi-permeable membrane having an average pore size that is smaller than said recombinant protein and/or said quaternary structures composed of a plurality of said recombinant protein and/or prevents passage of the majority of, preferably substantially all, proteins of 20 kDa to 500 kDa, in size through the semi-permeable membrane.

The filter can be any conventional filter in the art. Preferably, said filter includes a semi-permeable membrane. In a further preferred form, the said semi-permeable membrane has an average pore size that is smaller than the recombinant protein to thereby prevent passage of at least 90% of said recombinant protein through said semi-permeable membrane pores and withhold the recombinant protein by means of the filter.

In a further aspect, the said filter has an average pore size which prevents passage of at least 90% of proteins of 20 kDa to 500 kDa in size, more preferably, the said filter has an average pore size which prevents passage of at least 90% of proteins of 50 kDa to 400 kDa in size, and most preferably, the said filter has an average pore size which prevents passage of at least 90% of proteins of 75 kDa to 300 kDa in size. This pore size is preferred, when the recombinant protein is produced as whole virus or as virus like particles. In a still further aspect, the said semi-permeable membrane includes a material selected from the group consisting of polysulfone, polyethersulfone, and regenerated cellulose. However, any other material that allows removing of a portion of the first liquid and in case of a multiple process step, removing of a mixture of the first and the second liquid from the recombinant protein can be used. Said filter can be selected from the group consisting of a hollow fiber membrane ultrafiltration cartridge, flat sheets, or a cassette, with a hollow fiber membrane ultrafiltration cartridge being particularly preferred.

A preferred second liquid to be used in any of the methods described is a buffer, preferably a physiologically acceptable buffer with saline being particularly preferred.

In another aspect, the present invention concerns a method as herein described and claimed, wherein the second liquid is a buffer solution, preferably wash phosphate buffered saline (WPBS).

The concentrating step and the liquid addition step of the method as described herein can be performed substantially simultaneously or alternatively, the concentrating step and the liquid addition step are performed sequentially.

When the concentrating step and liquid addition step are performed sequentially, the order of the steps does not matter. For example, in a further aspect, the liquid addition step occurs prior to said concentrating step and in an alternative aspect, the concentrating step occurs prior to said liquid addition step. The liquid addition step and the concentrating step, regardless of the order in which they are performed, can be performed multiple times. For example, each of these respective steps can be performed at least two, at least three, at least four, at least five, at least 10, up to as many times as desired. In one aspect, the concentrating step and the liquid addition step are each performed at least two times. In another aspect, the concentrating step and the liquid addition step are each performed at least three times.

The concentration step of the methods provided herein can be performed such that the recombinant protein is concentrated from 3× to 50× in comparison to the volume of said first liquid. More preferably, said concentrating step can be done such that the recombinant protein is concentrated 4× to 20× in comparison to the volume of said first liquid. Most preferably, said concentration step can be done such that the recombinant protein is concentrated from 7× to 10× in comparison to the volume of the first liquid.

In another aspect, the present invention concerns a method as herein described and claimed, wherein the volume of the second liquid added in step (ii) is about the volume of the first and/or second liquid removed in step (iii). In other words, no concentration step is performed and/or required.

In the event, viral vectors such as a recombinant poxvirus, adenovirus or baculovirus is used to produce the recombinant protein it is recommended to inactivate the viral nucleic acid by an appropriate inactivation treatment. Such inactivation may occur anytime during the purification of the recombinant protein. Thus, inactivation may occur immediately after the harvest of the cell culture fluid comprising the recombinant protein or after the micro-filtration of the recombinant protein, if micro-filtration is done, prior or after the purification step, for instance, prior to or after the gel filtration, and prior to or after the anion exchange chromatography, if this is done.

Any conventional inactivation method can be used for purposes of the present invention. Thus, inactivation can be performed by chemical and/or physical treatments. In preferred forms, the volume of harvest fluids is determined and the temperature is brought to between about 32° C.-42° C., more preferably between about 34° C.-40° C., and most preferably between about 35° C.-39° C. Preferred inactivation methods include the addition cyclized binary ethylenimine (BEI), preferably in a concentration of about 1 mM to about 20 mM, preferably of about 2 mM to about 10 mM, still more preferably of about 2 mM to about 8 mM, still more preferably of about 3 mM to about 7 mM, most preferably of about 5 mM. For example the inactivation includes the addition of a solution of 2-bromoethyleneamine hydrobromide (BEA), preferably of about 0.4 M, which has been cyclized to 0.2 M binary ethylenimine (BEI) in 0.3 N NaOH, to the fluids to give a final concentration of about 5 mM BEI. Preferably, the fluids are then stirred continuously for 2-96 hours and the inactivated harvest fluids can be stored frozen at −40° C. or below or between about 1° C.-7° C. After inactivation is completed a sodium thiosulfate solution, preferably at 1.0M is added to neutralize any residual BEI. Preferably, the sodium thiosulfate is added in equivalent amount as compared to the BEI added prior to for inactivation. For example, in the event BEI is added to a final concentration of 5 mM, a 1.0M sodium thiosulfate solution is added to give a final minimum concentration of 5 mM to neutralize any residual BEI.

In another aspect, the present invention concerns a method as herein described and claimed, wherein the inactivating agent is an aziridine compound, preferably binary ethylenimine (BEI), and/or wherein the inactivating agent is added in a molar excess in relation to the vector.

In another aspect, the present invention concerns a method as herein described and claimed, wherein the neutralizing agent is sodium thiosulfate and/or wherein the neutralizing agent is added in a molar excess in relation to the inactivating agent.

In another aspect, the present invention concerns a method as herein described and claimed, wherein said method further comprises the step of admixing the mixture remaining after step (v) with a further component selected from the group consisting of pharmaceutically acceptable carriers, adjuvants, diluents, excipients, and combinations thereof.

In another aspect, the present invention concerns a method as herein described and claimed, wherein the virucidal activity of the mixture resulting from said method is reduced by at least 10% as compared to the mixture that has not undergone said method, and/or wherein the immunogenic composition produced by said method causes a loss of less than 1 log $TCID_{50}$ per mL of a live virus, when the live virus is mixed with the immunogenic composition for two or more hours.

In another aspect, the present invention concerns a method as herein described and claimed, wherein the live virus is Porcine Reproductive and Respiratory Syndrome (PRRS) virus.

In another aspect, the present invention concerns a method as herein described and claimed, wherein the method further comprises the step (vi) of harvesting the recombinant protein and/or the quaternary structures composed of a plurality of said recombinant protein remaining after step (v), and in particular further comprising the step of purifying the harvest comprising the recombinant protein and/or the quaternary structures composed of a plurality of said recombinant protein, by chromatographic procedure, preferably size exclusion chromatography.

In another aspect, the present invention concerns a method as herein described and claimed, wherein the method further comprises the step of combining the (purified) harvested recombinant protein and/or the quaternary structures composed of a plurality of said recombinant protein with at least one additional antigen.

In another aspect, the present invention concerns a method as herein described and claimed, wherein the at least one additional antigen is Porcine Reproductive and Respiratory Syndrome (PRRS) virus.

In a further aspect, the method further comprises the step of harvesting the recombinant protein obtained after at least a portion of said first liquid is removed from said recombinant protein.

As used herein, "harvesting" or "harvest" refers to collecting or recovering the recombinant protein. Any conventional method known in the art can be used to recover the recombinant protein either when a recombinant protein is being produced for use with the methods and compositions of the present invention, or when the recombinant protein is undergoing the methods described herein. In a particularly preferred manner of harvesting, the portion of said first liquid is removed from said recombinant protein via a filtration step and the recombinant protein is recovered or harvested from the filter retard. In a more preferred form, the recombinant protein is harvested or collected, or recovered from the retard of a semi-permeable membrane having the pore size described herein.

The recombinant protein remaining after having undergone the methods provided herein, preferably after having been harvested from the filter retard, is admixed with a further component selected from the group consisting of pharmaceutically acceptable carriers, adjuvants, diluents, excipients, and combinations thereof. Preferably, said further component is an adjuvant, even more preferably said adjuvant is a polymer of acrylic or methacrylic acid, and still more preferably said adjuvant is a carbomer.

In a further aspect of the present application, the method described above further comprises the steps admixing the recombinant protein obtained after the inactivating and neutralizing steps with a further component selected from the group consisting of pharmaceutically acceptable carriers, adjuvants, diluents, excipients, and combinations thereof. Prior to the mixing of the purified recombinant protein with an adjuvant, it is also recommended to dialyze the purified recombinant protein against phosphate buffered saline, pH 7.4 or any other physiological buffer.

As used herein, "a pharmaceutical-acceptable carrier" and a "veterinary acceptable carrier" includes any and all solvents, dispersion media, coatings, stabilizing agents, diluents, preservatives, antibacterial and antifungal agents, isotonic agents, adsorption delaying agents, and the like.

"Adjuvants" as used herein, can include aluminum hydroxide and aluminum phosphate, saponins e.g., QUIL-A®, QS-21 (Cambridge Biotech Inc., Cambridge Mass.), GPI-0100 (Galenica Pharmaceuticals, Inc., Birmingham, Ala.), water-in-oil emulsion, oil-in-water emulsion, water-in-oil-in-water emulsion. The emulsion can be based in particular on light liquid paraffin oil (European Pharmacopea type); isoprenoid oil such as squalane or squalene; oil resulting from the oligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the PLURONIC® products (BASF Corporation), especially L121. See Hunter et al., The Theory and Practical Application of Adjuvants (Ed.Stewart-Tull, D. E. S.). JohnWiley and Sons, NY, pp 51-94 (1995) and Todd et al., Vaccine 15:564-570 (1997). For example, it is possible to use the SPT emulsion described on page 147 of "Vaccine Design, The Subunit and Adjuvant Approach" edited by M. Powell and M. Newman, Plenum Press, 1995, and the emulsion MF59 described on page 183 of this same book. Further suitable adjuvants include, but are not limited to, the RIBI adjuvant system (Ribi Inc.), Block co-polymer (CytRx, Atlanta Ga.), SAF-M (Chiron, Emeryville Calif.), monophosphoryl lipid A, Avridine lipid-amine adjuvant, heat-labile enterotoxin from *E. coli* (recombinant or otherwise), cholera toxin, IMS 1314 or muramyl dipeptide among many others. Among the copolymers of maleic anhydride and alkenyl derivative, the copolymers EMA (Monsanto), which are copolymers of maleic anhydride and ethylene, are included. The dissolution of these polymers in water leads to an acid solution that will be neutralized, preferably to physiological pH, in order to give the adjuvant solution into which the immunogenic, immunological or vaccine composition itself will be incorporated.

A further instance of an adjuvant is a compound chosen from the polymers of acrylic or methacrylic acid and the copolymers of maleic anhydride and alkenyl derivative. Advantageous adjuvant compounds are the polymers of acrylic or methacrylic acid which are cross-linked, especially with polyalkenyl ethers of sugars or polyalcohols. These compounds are known by the term carbomer (Phameuropa Vol. 8, No. 2, June 1996). Persons skilled in the art can also refer to U.S. Pat. No. 2,909,462 which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. The products sold under the name Carbopol; (BF Goodrich, Ohio, USA) are particularly appropriate. They are cross-linked with an allyl sucrose or with allyl pentaerythritol. Among then, there may be mentioned Carbopol 974P, 934P and 971P. Most preferred is the use of Carbopol 971P.

"Diluents" can include water, saline, dextrose, ethanol, glycerol, and the like. Isotonic agents can include sodium chloride, dextrose, mannitol, sorbitol, and lactose, among others. Stabilizers include albumin and alkali salts of ethylendiamintetracetic acid, among others.

A "preservative" as used herein refers to an anti-microbiological active agent, such as for example Gentamycin, Merthiolate, and the like. In particular adding of a preservative is most preferred for the preparation of a multi-dose composition. Those anti-microbiological active agents are added in concentrations effective to prevent the composition of interest for any microbiological contamination or for inhibition of any microbiological growth within the composition of interest.

Further purification of the recombinant protein can be achieved with chromatography procedures, preferably a two-step chromatography procedure. If the recombinant protein is assembled to virus like particles (VLP), one step, preferably the first step, is preferably a size exclusion (gel filtration) chromatography, which can be done, for instance, by using a Sephacryl S300 matrix. In 1ab scale use of HiPrep 26/60 Sephacryl S300HR columns are most preferred. However, any other size exclusion chromatography matrices known to a person skilled in the art can be used, which allow the separation of the recombinant protein VLPs from the culture filtrate or supernatant. Suitable matrices are described, for instance, in E. L. V. Harris and S. Angel (eds.), Protein purification methods—a practical approach, IRL Press Oxford 1995). The gel filtration chromatography can be conducted, for instance, by loading the column with the crude preparation comprising the recombinant protein with a flow-rate of 1.0 ml/min and eluting the column with 1.5 column volume of a buffer comprising 20 mM Tris, pH 6.5, 5 mM DTT. However, the recombinant protein can also be purified by using affinity chromatography, for instance, via selective binding to an immobilized recombinant protein specific antibody, or any other method known to a person skilled in the art.

In order to obtain a higher purity grade a second chromatography step can be done, which however is different from the first one. For instance if the first purification step/chromatography step is size exclusion (gel filtration) the second should different from that e.g. an affinity chromatography, ion exchange chromatography, etc. Preferably, if the first step to purify recombinant protein is a size exclusion (gel filtration) chromatography, the second step can be ion-exchange chromatography, preferably anion-exchange chromatography (AIEX). A preferred anion-exchange chromatography matrix for the purification of recombinant protein is Q Sepharose. In a small scale of about 50 ml, use of 5 ml HITRAP® Q Sepharose HP (GE Healthcare Bioprocess R&D AB) columns are most preferred.

The present application does not only provide methods of producing recombinant protein containing immunogenic composition, it also relates to a recombinant protein containing immunogenic composition.

In another aspect, the present invention concerns an immunogenic composition obtainable by a method as herein described and claimed.

In a further aspect, the virucidal activity of the recombinant protein containing immunogenic composition produced by the methods herein is reduced by at least 10% as compared to a recombinant protein containing immunogenic composition that has not undergone said production method. More preferably, the virucidal activity of the recombinant protein containing immunogenic composition is reduced by at least 50% as compared to a recombinant protein containing immunogenic composition that has not undergone said production method. Still more preferably, the virucidal activity of the recombinant protein containing immunogenic composition is reduced by at least 70% as compared to a recombinant protein containing immunogenic composition that has not undergone said production method. Even still more preferably, the virucidal activity of the recombinant protein containing immunogenic composition is reduced by at least 90% as compared to a recombinant protein containing immunogenic composition that has not undergone said production method.

For the purpose of the current invention the term "virucidal activity" means, that a liquid, fluid, solution, composition or the like inactivates or kills live viruses or live bacteria to a certain extent, when said liquid, fluid, solution, composition or the like is mixed with such live viruses or live bacteria. Thus, a reduction of the virucidal activity of a liquid, fluid, solution, composition or the like by at least 10% means, that the survival rate of live viruses or live bacteria is 90% higher in a liquid, fluid, solution, composition or the like that has undergone any of the production methods described herein, as compared to a liquid, fluid, solution, composition or the like, that has not undergone any of such production methods.

The recombinant protein immunogenic composition produced by the method described herein causes a loss of less than 1 log $TCID_{50}$ of a live virus or less than 1 log CFU per ml of a live bacterium, when the live virus or live bacterium is mixed with the recombinant protein immunogenic composition and incubated for 2 or more hours, preferably for more than 4 hours, even more preferably for more than 12 hours, even more preferably for more than 24 hours, even more preferably for more than 2 days, even more preferably for more than 4 days, even more preferably for more than 7 days, even more preferably for more than 2 weeks, even more preferably for more than 4 weeks, even more preferably for more than 2 months, even more preferably for more than 3 months, even more preferably for more than 4 months, even more preferably for more than 6 months, even more preferably for more than 9 months, even more preferably for more than 12 months, even more preferably for more than 18 months, most preferably for more than 2 years. More preferably, recombinant protein immunogenic composition produced by the method described herein causes a loss of less than 0.9 log $TCID_{50}$ per ml of a live virus or less than 0.9 log CFU per ml of a live bacterium, when the live virus or live bacterium is mixed and incubated with the recombinant protein immunogenic composition for 2 or more hours, preferably for more than 4 hours, even more preferably for more than 12 hours, even more preferably for more than 24 hours, even more preferably for more than 2 days, even more preferably for more than 4 days, even more preferably for more than 7 days, even more preferably for more than 2 weeks, even more preferably for more than 4 weeks, even more preferably for more than 2 months, even more preferably for more than 3 months, even more preferably for more than 4 months, even more preferably for more than 6 months, even more preferably for more than 9 months, even more preferably for more than 12 months, even more preferably for more than 18 months, most preferably for more than 2 years. Even more preferably, the recombinant protein immunogenic composition produced by the method described herein causes a loss of less than 0.7 log $TCID_{50}$ per ml of a live virus or less than 0.7 log CFU per ml of a live bacterium, when the live virus or live bacterium is mixed and incubated with the recombinant protein immunogenic composition for 2 or more hours, preferably for more than 4 hours, even more preferably for more than 12 hours, even more preferably for more than 24 hours, even more preferably for more than 2 days, even more preferably for more than 4 days, even more preferably for more than 7 days, even more preferably for more than 2 weeks, even more preferably for more than 4 weeks, even more preferably for more than 2 months, even more preferably for more than 3 months, even more preferably for more than 4 months, even more preferably for more than 6 months, even more preferably for more than 9 months, even more preferably for more than 12 months, even more preferably for more than 18 months, most preferably for more than 2 years. Still more preferably, the recombinant protein immunogenic composition produced by steps by the method described herein causes a loss of less than 0.5 log $TCID_{50}$ per ml of a live virus or less than 0.5 log CFU per ml of a live bacterium, when the live virus or live bacterium is mixed and incubated with the recombinant protein immunogenic composition for 2 or more hours, preferably for more than 4 hours, even more preferably for more than 12 hours, even more preferably for more than 24 hours, even more preferably for more than 2 days, even more preferably for more than 4 days, even more preferably for more than 7 days, even more preferably for more than 2 weeks, even more preferably for more than 4 weeks, even more preferably for more than 2 months, even more preferably for more than 3 months, even more preferably for more than 4 months, even more preferably for more than 6 months, even more preferably for more than 9 months, even more preferably for more than 12 months, even more preferably for more than 18 months, most preferably for more than 2 years. Even more preferably, the recombinant protein immunogenic composition produced by the method described herein causes a loss of less than 0.3 log $TCID_{50}$ per ml of a live virus or less than 0.3 log CFU per ml of a live bacterium, when the live virus or live bacterium is mixed and incubated with the recombinant protein immunogenic composition for 2 or more hours, preferably for more than 4 hours, even more preferably for more than 12 hours, even more preferably for more than 24 hours, even more preferably for more than 2 days, even more preferably for more than 4 days, even more preferably for more than 7 days, even more preferably for more than 2 weeks, even more preferably for more than 4 weeks, even more preferably for more than 2 months, even more preferably for more than 3 months, even more preferably for more than 4 months, even more preferably for more than 6 months, even more preferably for more than 9 months, even more preferably for more than 12 months, even more preferably for more than 18 months, most preferably for more than 2 years. The $TCID_{50}$ per ml can be estimated by a standard in vitro titration assay which allows the estimation of the amount of a live virus. The CFU per ml can be determined also by a standard in vitro titration assay which allows the estimation of the amount of a live bacterium. The term "per ml" preferably refers to 1 ml of a fluid. Such purified recombinant protein does not only show reduced virucidal activity, as defined herein, it also shows an increased immunogenicity as compared to a non-purified recombinant protein as defined herein, preferably such recombinant protein increases the cellular and/or antibody mediated immune response by at least 10%, preferably by at least 20%, more preferably by at least 30%, even more preferably by at least 40%, even more preferably by at least 50%, even more preferably by at least 75%, most preferably by at least 100% as compared to the cellular and/or antibody mediated immune response elicited by a reference immunogenic composition comprising a non-purified recombinant protein.

The immunogenic compositions comprising the purified recombinant protein, preferably those obtainable by the methods described herein are characterized by an increased immunogenicity as compared to an immunogenic composition not comprising such a purified recombinant protein.

In addition, the terms "increased immunogenicity or improved immunogenicity" as used herein, mean that the immune response caused by an immunogenic composition comprising an antigen of interest is increased as compared to a reference immunogenic composition comprising a different antigen or different purity grade of the antigen, whether this immune response is a cellular mediated and/or antibody mediated immune response. According to a preferred embodiment, the term increased immunogenicity or improved immunogenicity means, that the antibody mediated immune response elicited by an immunogenic composition comprising the antigen of interest is increased as compared to a reference immunogenic composition comprising a different antigen or a different purity grade of the antigen. In this regard antibody mediated immune response means, that the production of antibodies, which are specific to the antigen of interest is increased as compared to the antibody production elicited by a reference immunogenic composition comprising a different antigen or a different purity grade of the antigen.

The term "increased" means, that the cellular and/or antibody mediated immune response is increased by at least 10%, preferably by at least 20%, more preferably by at least 30%, even more preferably by at least 40%, even more preferably by at least 50%, even more preferably by at least 75%, most preferably by at least 100% as compared to the cellular and/or antibody mediated immune response elicited by a reference immunogenic composition comprising a recombinant protein or a different purity grade of the recombinant protein.

It is in the general knowledge of a person skilled in the art how to measure the cellular and/or antibody mediated immune response. In particular, it is clear to such person skilled in the art either to compare the cellular mediated immune response of the immunogenic composition of interest with cellular mediated immune response of the reference, or the antibody mediated immune response of the immunogenic composition of interest with that of the reference composition, but neither the cellular mediated immune response of a immunogenic composition of interest with the antibody mediated immune response of the reference or vice versa. Moreover, the cellular mediated immune response can be measured, for instance, by measuring the activation of cytotoxic T-cells by an immunogenic composition/antigen of interest. The antibody mediated immune response can be measured, for instance, by measuring the amount of antigen specific antibodies, generated in cause of the administration of the immunogenic composition comprising such antigen to an animal. The cellular and/or antibody mediated immune response can be measured, for instance, by using a mouse model. According to the current invention, the mouse model is used as the reference method.

The term "immunogenic composition" means, but is not limited to, a composition of matter that comprises at least one antigen which elicits a cellular and/or antibody-mediated immune response in a host against the antigen of interest. Usually, an "immune response" includes but is not limited to one or more of the following effects: the production or activation of antibodies, B cells, helper T cells, suppressor T cells, and/or cytotoxic T cells and/or gamma-delta T cells, directed specifically to an antigen or antigens included in the composition or vaccine of interest. Preferably, the host will display either a therapeutic or protective immune response such that resistance to new infection will be enhanced and/or the clinical severity of the disease reduced. In such a case the immunogenic composition is a "vaccine". Such protection will be demonstrated by either a reduction or lack of symptoms normally displayed by an infected host, a quicker recovery time and/or a lowered viral titer in the infected host.

In another aspect, the present invention concerns an immunogenic composition as herein described and claimed, wherein the immunogenic composition further comprises an attenuated live virus, preferably an attenuated Porcine Reproductive and Respiratory Syndrome (PRRS) virus, or an attenuated live bacterium.

"Live" virus or bacterium, for purposes of the present invention, refers to a virus or bacterium that is capable of replicating in a host. A preferred live virus and a preferred live bacterium of the present invention are the PRRS virus and the *Mycoplasma hyopneumonia* bacterium, respectively. However, the term live virus or live bacterium is not limited to PRRS and *Mycoplasma hypneumoniae*, respectively.

In another aspect, the present invention concerns an immunogenic composition as herein described and claimed, wherein the attenuated live virus is Porcine Reproductive and Respiratory Syndrome (PRRS) virus.

In another aspect, the present invention concerns an immunogenic composition as herein described and claimed, wherein the immunogenic composition induces a protective immune response against a pathogen, preferably a pathogen comprising a recombinant protein as herein described and claimed, after the administration of one dose of the immunogenic composition.

In another aspect, the present invention concerns an immunogenic composition as herein described and claimed, wherein the immunogenic composition induces a protective immune response against PRRS virus after the administration of one dose of the immunogenic composition.

The recombinant protein immunogenic composition obtained according to the method described above, or the recombinant protein used in step i) of the method described above, can be combined with at least one additional antigen, preferably a viral or bacterial antigen, and even more preferably, a viral or bacterial antigen from at least one other disease-causing organism in swine. The additional antigen can be any one of those disclosed in the international patent application WO2007/094893 (the contents and teachings of which are hereby incorporated by reference). Briefly, the additional antigens can be antigens of any other disease-causing organisms of swine. Preferably the "another disease-causing organisms" of swine are selected from the group consisting of: *Actinobacillus* pleuropneumonia (1); Adenovirus (2); Alphavirus such as Eastern equine encephalomyelitis viruses (3); *Bordetella bronchiseptica* (4); *Brachyspira* spp. (5), preferably *B. hyodyentheriae* (6); *B. piosicoli* (7), *Brucella suis*, preferably biovars 1, 2, and 3 (8); Classical swine fever virus (9); *Clostridium* spp. (10), preferably *Cl. difficile* (11), *Cl. perfringens* types A, B, and C (12), *Cl. novyi* (13), *Cl. septicum* (14), *Cl. tetani* (15); Coronavirus (16), preferably Porcine Respiratory Corona virus (17); Eperythrozoonosis suis (18); *Erysipelothrix rhsiopathiae* (19) *Escherichia coli* (20); *Haemophilus parasuis*, preferably subtypes 1, 7 and 14 (21) Hemagglutinating encephalomyelitis virus (22); Japanese Encephalitis Virus (23); *Lawsonia intracellularis* (24) *Leptospira* spp. (25), preferably *Leptospira australis* (26); *Leptospira canicola* (27); *Leptospira grippotyphosa* (28); *Leptospira icterohaemorrhagicae* (29); and *Leptospira interrogans* (30); *Leptospira pomona* (31); *Leptospira tarassovi* (32); *Mycobacterium* spp. (33) preferably *M. avium* (34), *M. intracellular* (35) and *M. bovis* (36); *Mycoplasma hyopneumoniae* (37); *Pasteurella multocida* (38); Porcine cytomegalovirus (39); Porcine Parvovirus (40); Porcine Reproductive and Respiratory Syndrome Virus (41); Pseudorabies virus (42); Rotavirus (43); *Salmonella* spp. (44), preferably *S. thyhimurium* (45) and *S. choleraesuis* (46); *Staph. hyicus* (47); *Staphylococcus* spp. (48) preferably *Streptococcus* spp. (49), preferably *Strep. suis* (50); Swine herpes virus (51); Swine Influenza Virus (52); Swine pox virus (53); Swine pox virus (54); Vesicular stomatitis virus (55); Virus of vesicular exanthema of swine (56); *Leptospira* Hardjo (57); and/or *Mycoplasma hyosynoviae* (58).

In another aspect, the present invention concerns a kit comprising a container containing the immunogenic composition as herein described and claimed.

In another aspect, the present invention concerns a kit as herein described and claimed further comprising at least one additional container containing at least one additional antigen selected from the group consisting of attenuated live virus, preferably attenuated PRRS virus, and attenuated live bacterium.

In another aspect, the present invention concerns an immunogenic composition as herein described and claimed for use as a medicament, preferably as a vaccine.

In another aspect, the present invention concerns an immunogenic composition as herein described and claimed and/or the kit as herein described and claimed, for use in a method of reducing one or more clinical symptoms of a pathogen infection in an animal as compared to an animal not receiving said immunogenic composition.

The term "reduction in the incidence of or severity of clinical signs" shall mean that any of such signs are reduced in incidence or severity in animals receiving an administration of the vaccine in comparison with a "control group" of animals when both have been infected with or challenged by the pathogen from which the immunological active component(s) in the vaccine are derived and wherein the control group has not received an administration of the vaccine or immunogenic composition. In this context, the term "decrease" or "reduction" means a reduction of at least 10%, preferably 25%, even more preferably 50%, most preferably of more than 100% in the vaccinated group as compared to the control group not vaccinated.

As used herein, "clinical symptoms" or "clinical signs" shall refer to signs of infection from pathogens that are directly observable from a live animal such as symptoms. Representative examples will depend on the pathogen selected but can include things such as nasal discharge, lethargy, coughing, elevated fever, weight gain or loss, dehydration, diarrhea, swelling, lameness, and the like.

As used herein, a "protective immune response" refers to a reduced incidence of or reduced severity of clinical, pathological, or histopathological signs or symptoms of infection from a pathogen of interest up to and including the complete prevention of such signs or symptoms.

The term "pathological signs" shall refer to signs of infection that are observable at the microscopic or molecular level, through biochemical testing, or with the naked eye upon necropsy.

The term "histopathological signs" signs shall refer to signs of tissue changes resulting from infection.

The terms, "clinical symptoms" or "clinical signs" are defined above.

The following clauses are described herein:

1. A method of producing an immunogenic composition comprising a recombinant protein, wherein the method comprises the steps in the following order:
   (i) providing/obtaining a mixture comprising:
      a first liquid,
      recombinant protein and/or quaternary structures composed of a plurality of said recombinant protein, and
      a vector comprising a nucleic acid sequence encoding said recombinant protein;
   (ii) adding a second liquid to the mixture of step (i), wherein the second liquid is different from the first liquid;
   (iii) washing, and optionally finally concentrating, the recombinant protein and/or quaternary structures composed of a plurality of said recombinant protein in the mixture by further adding additional second liquid to the mixture resulting from step (ii) and removing a portion of the first and/or second liquid from such combined mixture;
   (iv) inactivating the vector by adding an inactivating agent to the mixture resulting from step (iii);
   (v) neutralizing the inactivating agent by adding a neutralizing agent to the mixture resulting from step (iv).

2. The method of clause 1, wherein the mixture of step (i) is obtainable by a procedure comprising the steps of
   a) permitting infection of susceptible cells in culture with a vector comprising a nucleic acid sequence encoding said recombinant protein and/or quaternary structures composed of a plurality of said recombinant protein, wherein said recombinant protein and/or quaternary structures composed of a plurality of said recombinant protein is expressed by said vector,
   b) thereafter recovering the recombinant protein and/or quaternary structures composed of a plurality of said recombinant protein from the cell culture, wherein preferably cell debris is separated from the recombinant protein and/or quaternary structures composed of a plurality of said recombinant protein via a separation step, preferably including a micro filtration through at least one filter, preferably two filters, wherein the at least one filter preferably has a pore size larger than the recombinant protein and/or quaternary structures composed of a plurality of said recombinant protein, in particular has a pore size of about 0.1 µm to about 4 µm.

3. The method of clause 2, wherein the cell culture in step (a) is maintained at 27±2° C., preferably while the recombinant protein and/or quaternary structures composed of a plurality of said recombinant protein is expressed by said vector, and/or wherein the recovering in step (b) occurs 6 to 8 days, preferably 8 days, after inoculation of the cells with the vector.

4. The method of clauses 2 or 3, wherein the separation step includes or consists of:
   a micro filtration through at least one filter having a pore size of about 2 µm to about 4 µm, and/or
   a micro filtration through at least one filter having a pore size of about 0.1 µm to about 0.8 µm.

5. The method of any one of clauses 1 to 4, wherein said first liquid comprises a portion of cell culture medium or consists of cell culture medium, and wherein the cell culture medium preferably is insect cell culture medium.

6. The method of any one of clauses 1 to 5, wherein said recombinant protein is selected from the group consisting of:
   a PPV VP2 protein preferably comprising or consisting of a sequence having at least 70%, at least 75%, at least 80%, at least 85%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, at least 99.9%, or 100% sequence identity with the sequence of SEQ ID NO:1, SEQ ID NO:2 and/or SEQ ID NOS 5 to 16.

7. The method of any one of clauses 1 to 6, wherein said quaternary structures composed of a plurality of said recombinant protein are virus-like particles or wherein said quaternary structures composed of a plurality of said recombinant protein are homotrimers.

8. The method of any one of clauses 1 to 7, wherein the vector is a recombinant virus, preferably baculovirus, and/or wherein the nucleic acid sequence is a DNA sequence.

9. The method of any one of clauses 1 to 8, wherein the vector comprising a nucleic acid encoding said recombinant protein and/or quaternary structures composed of a plurality of said recombinant protein is a recombinant baculovirus, wherein said baculovirus comprises a DNA sequence encoding said recombinant protein and/or quaternary structures composed of a plurality of said recombinant protein.

10. The method of any one of clauses 1 to 9, wherein in step (iii) said recombinant protein and/or said quaternary structures composed of a plurality of said recombinant protein is washed with at least 2×, preferably from 2× to 3×, of second liquid, and optionally finally concentrated, in comparison to the original volume of said recombinant protein and/or said quaternary structures composed of a plurality of said recombinant protein in the mixture of step (i).

11. The method of any one of clauses 1 to 10, wherein in step (iii) such washing step(s), i.e. the process of diafiltration, is performed at a temperature of lower than 37° C., more preferably at a temperature of lower than 30° C., even more preferably at a temperature of lower than 20° C., even more preferably at a temperature of lower than 10° C., such as for instance at a temperature between 4° C. and 29° C., for instance 27° C. or 4° C.

12. The method of any one of clauses 1 to 11, wherein in step (iii) the portion of the first and/or second liquid is removed from the mixture by filtration, wherein preferably a filter or a hollow filter is utilized comprising a semi-permeable membrane having an average pore size that is smaller than said recombinant protein and/or said quaternary structures composed of a plurality of said recombinant protein and/or prevents passage of the majority of, preferably substantially all, proteins of 20 kDa to 500 kDa, in size through the semi-permeable membrane.

13. The method of any one of clauses 1 to 12, wherein the second liquid is a buffer solution, preferably wash phosphate buffered saline (WPBS).

14. The method of any one of clauses 1 to 13, wherein the volume of the second liquid added in step (ii) is about the volume of the first and/or second liquid removed in step (iii), i.e. no concentration step is performed and/or required.

15. The method of any one of clauses 1 to 14, wherein the inactivating agent is an aziridine compound, preferably binary ethylenimine (BEI), and/or wherein the inactivating agent is added in a molar excess in relation to the vector.

16. The method of any one of clauses 1 to 15, wherein the neutralizing agent is sodium thiosulfate and/or wherein the neutralizing agent is added in a molar excess in relation to the inactivating agent.

17. The method of any one of clauses 1 to 16, wherein said method further comprises the step of admixing the mixture remaining after step (v) with a further component selected from the group consisting of pharmaceutically acceptable carriers, adjuvants, diluents, excipients, and combinations thereof.

18. The method according to any one of clauses 1 to 17, wherein the virucidal activity of the mixture resulting from said method is reduced by at least 10% as compared to the mixture that has not undergone said method, and/or wherein the immunogenic composition produced by said method causes a loss of less than 1 log $TCID_5O$ per mL of a live virus, when the live virus is mixed with the immunogenic composition for two or more hours.

19. The method according to clause 18, wherein the live virus is Porcine Reproductive and Respiratory Syndrome (PRRS) virus.

20. The method according to any one of clauses 1 to 19, wherein the method further comprises the step (vi) of harvesting the recombinant protein and/or the quaternary structures composed of a plurality of said recombinant protein remaining after step (v), and in particular further comprising the step of purifying the harvest comprising the recombinant protein and/or the quaternary structures composed of a plurality of said recombinant protein, by chromatographic procedure, preferably size exclusion chromatography.

21. The method according to any one of clauses 1 to 20, wherein the method further comprises the step of combining the (purified) harvested recombinant protein and/or the quaternary structures composed of a plurality of said recombinant protein with at least one additional antigen.

22. The method according to clause 21, wherein the at least one additional antigen is Porcine Reproductive and Respiratory Syndrome (PRRS) virus.

23. An immunogenic composition obtainable by a method according to any one of clauses 1 to 22.

24. The immunogenic composition according to clause 23, wherein the immunogenic composition further comprises an attenuated live virus, preferably an attenuated Porcine Reproductive and Respiratory Syndrome (PRRS) virus, or an attenuated live bacterium.

25. The immunogenic composition according to clause 23 or 24, wherein the attenuated live virus is Porcine Reproductive and Respiratory Syndrome (PRRS) virus.

26. The immunogenic composition according to any one of clauses 23 to 25, wherein the immunogenic composition induces a protective immune response against a pathogen, preferably a pathogen comprising a recombinant protein according to clause 6, after the administration of one dose of the immunogenic composition.

27. The immunogenic composition according to any one of clauses 23 to 26, wherein the immunogenic composition induces a protective immune response against PRRS virus after the administration of one dose of the immunogenic composition.

28. Kit comprising a container containing the immunogenic composition according to any one of clauses 23 to 27.

29. The kit according to clause 28 further comprising at least one additional container containing at least one additional antigen selected from the group consisting of attenuated live virus, preferably attenuated PRRS virus, and attenuated live bacterium.

30. The immunogenic composition according to any one of clauses 23 to 29 for use as a medicament, preferably as a vaccine.

31. The immunogenic composition according to any one of clauses 23 to 29 and/or the kit according to any one of clauses 28 or 29, for use in a method of reducing one or more clinical symptoms of a pathogen infection in an animal as compared to an animal not receiving said immunogenic composition.

EXAMPLES

The following examples are set forth below to illustrate specific embodiments of the present invention. These examples are merely illustrative and are understood not to limit the scope or the underlying principles of the present invention.

Example 1

Production of Porcine Parvovirus (PPV) 27a VP2—Upstream Processing

The PPV 27a VP2 was produced in baculovirus-infected SF+ cells, and is BEI-inactivated in a process somewhat similar to that of PCV2 ORF2 (WO 2006/072065; Examples 1 to 3). However, the PPV 27a VP2 uses a different baculovirus backbone designated as "DiamondBac" (Sigma Aldrich, D6192) (instead of the older BACULOGOLD® backbone used for PCV2 ORF2).

Porcine parvovirus (PPV) 27a VP2 nucleotide sequence was obtained from Genbank Accession AY684871.1. The PPV 27a VP2 coding region was reverse-translated and codon-optimized for *Drosophila* using the SCITOOLS® Web Tools software provided by Integrated DNA Technologies. The codon-optimized PPV 27a VP2 gene was further modified to insert two ClaI restriction enzyme sites into the VP2 coding region, along with the addition of BamHI and NotI restriction enzyme sites to the 5'- and 3'-ends, respectively. The ClaI sites are inserted in a manner so as to not disrupt the VP2 coding region. The insertion of the ClaI sites introduces three minor amino acid changes in the predicted 27a VP2 amino acid sequence. The amino acid changes resulting from the ClaI insertions are at position 25 (Glycine⇒Isoleucine), 36 (Alanine⇒Serine), and 37 (Glycine⇒Isoleucine). The codon-optimized PPV 27a-ClaI VP2 gene was chemically synthesized and subsequently cloned into the standard cloning plasmid, pUC57, at Integrated DNA Technologies (PPV27a-ClaI 38320377). The PPV 27a-ClaI gene was then excised from the Integrated DNA Technologies-provided pUC57 plasmid by digestion with BamHI and NotI restriction enzymes, and the PPV 27a-ClaI gene was subcloned into the respective enzyme sites of the baculovirus transfer vector pVL1393 (BD Pharmingen, 21486P). The pVL1393 plasmid containing the PPV 27a-ClaI gene was amplified in DH5a *E. coli* (INVITROGEN® MAX EFFICIENCY® (Life Technologies, Inc.)) and subsequently extracted and purified using a commercial plasmid purification kit (QIAprep Spin Miniprep kit, Qiagen). The purified pVL1393 plasmid containing the PPV 27a-ClaI gene and the linearized baculovirus DiamondBac backbone were co-transfected into Sf9 insect cells using Escort™ Transfection Reagent (Sigma Aldrich, E9770) to generate recombinant baculovirus. Limiting dilution was performed to obtain a purified recombinant baculovirus stock containing the PPV 27a-ClaI VP2 gene under control of the polyhedrin promoter. The baculovirus expression vector system (BEVS) is utilized to allow suspension insect cell culture (SF+) to produce recombinant antigen comprised of PPV 27a VP2 protein. For this product, the infected SF+ cell culture is run in batch mode for approximately seven days and is then processed to remove cell debris and media components.

Example 2

Production of Porcine Parvovirus (PPV) 27a VP2—Downstream Processing

Two consecutive steps are followed to comprise the downstream processing. The removal of cell debris occurs in the process known as "clarification", while the removal of media components is achieved through two volumes of wash phosphate buffered saline (WPBS), called "diafiltration".

PPV 27a VP2 Baculovirus-vector is produced in bioreactors. The medium is added pre sterilized or sterile-filtered into the bioreactor. The medium is added with SF+ cells originating from expansion cultures. The cells are simultaneously inoculated (concurrent infection) upon planting with PPV 27a VP2 Baculovirus seed. Throughout the virus propagation temperature is maintained at 27±2° C. and pH is monitored. Dissolved Oxygen (DO) is controlled by sparging cleaned-compressed air, and oxygen ($O_2$). The harvest window occurs between 6 to 8 days after virus infection and the harvest criterion of ≤20% Cell Viability is achieved. At harvest, PPV 27a VP2 antigen fluids are clarified using two sets of filters, a pre-filter of 2.0-4.0 μm pore size and a final filter of 0.1-0.8 μm pore size. The filtered harvest fluids are collected in a tank.

Clarified PPV 27a VP2 antigen fluids are then "diafiltered" with ≥two volumes (2×-2.5×) WPBS [using a 300,000-500,000 kilo Dalton (kDa) nominal molecular weight cut-off (NMWC) hollow fiber filter] at a temperature between 4° C. and 29° C. After diafiltration, the PPV 27a VP2 antigen temperature is increased to 37±2° C. for inactivation by addition of binary ethylenimine (BEI) to a final concentration of 5 mM. The antigen is incubated at 37±2° C. and mixed for 72-96 hours. Residual BEI is neutralized with sodium molar excess of thiosulfate solution for at least 30 minutes. The PPV 27a VP2 antigen fluids are transferred to bags for storage at 4±3° C. until vaccine blending.

The data below in Tables 1A and 1B show that PPV 27a VP2 vaccine is non-virucidal to REPROCYC® PRRS EU vaccine and INGELVAC® PRRS MLV vaccine, respectively, when mixed together for up to 8 hours (one working day).

TABLE 1A

Two (2) serials of REPROCYC ® PRRS EU ®, batch numbers 3910003A (10 dose) and 3910004A (50 dose), were stored at 5° C. ± 3° C. in the packaging materials until being used for the study. Two (2) serials of PPV 27a VP2, batch numbers 7600016A (10dose) and 7600018B (50dose), were used as diluent for the INGELVAC ® REPROCYC ® PRRS EU batches 3910003A (10 dose) and 3910004A (50 dose), respectively. These two batches were stored at 5° C. ± 3° C. in the packaging materials until being used for the study. REPROCYC ® PRRS EU ® vaccine, after reconstitution (either in the CARBOPOL ®-containing diluent in group 1 or the liquid vaccine PPV 27a VP2 in group 2), was stored at room temperature (15-25° C.) for a maximum period of 8 hours and tested for titer at zero, two, four and 8 hours. Group 1 results of the virus titration (Log10 TCID50/2 mL dose) in Table 1A below at T0, T2, T4 and T8 demonstrated the stability of the virus up to 8 h. Group 2 results of the virus titration (Log10 TCID50/2 mL dose) on the associated product at T0, T2, T4 and T8 demonstrated that PPV 27a VP2 vaccine does not have virucidal activity against REPROCYC ® PPRS EU ® up to 8 h.

| Group | Active substance | Serial number | Objective | Testing (Hrs) Log10 TCID50/2 mL dose | | | |
|---|---|---|---|---|---|---|---|
| | | | | 0 | 2 | 4 | 8 |
| 1 | REPROCYC ® PRRS EU ® + Carbopol diluent | 3910003A + 8080019A | Control REPROCYC ® PRRS EU | 5.8 | 5.9 | 5.9 | 5.9 |
| | | 3910004A + 8080019A | | 6.0 | 6.0 | 5.9 | 6.0 |
| 2 | PPV 27a VP2 + REPROCYC ® PRRS EU ® | 3910003A + 7600016A | Determination of in-use stability for the associated use claim | 5.8 | 5.9 | 5.8 | 5.8 |
| | | 3910004A + 7600018B | | 6.0 | 6.1 | 6.0 | 5.9 |

TABLE 1B

Two (2) serials of INGELVAC ® PRRS MLV, batch numbers 2451189A (10 dose) and 2451188A (50 dose), were stored at 5° C. ± 3° C. in the packaging materials until being used for the study. Two (2) serials of PPV 27a VP2, batch numbers 7600016A (10dose) and 7600018B (50dose), were used as diluent for the INGELVAC ® PRRS MLV batches 2451189A (10 dose) and 2451188A (50 dose), respectively. These two batches were stored at 5° C. ± 3° C. in the packaging materials until being used for the study. INGELVAC ® PRRS MLV vaccine, after reconstitution (either in the CARBOPOL ®-containing diluent in group 1 or the liquid vaccine PPV 27a VP2 in group 2), was stored at room temperature (15-25° C.) for a maximum period of 8 hours and tested for titer (TCID50 per 2 mL dose) at zero, two, four and 8 hours. Group 1 results of the virus titration (Log10 TCID50/2 mL dose) in Table 1B below at T0, T2, T4 and T8 demonstrated the stability of the virus up to 8 h. Group 2 results of the virus titration (Log10 TCID50/2 mL dose) on the associated product at T0, T2, T4 and T8 demonstrated that PPV 27a VP2 vaccine does not have virucidal activity against INGELVAC ® PRRS MLV up to 8 h.

| Group | Active substance | Serial number | Objective | Testing (Hrs) Log10 TCID50/2 mL dose | | | |
|---|---|---|---|---|---|---|---|
| | | | | 0 | 2 | 4 | 8 |
| 1 | INGEL VAC ® PRRS MLV + Carbopol diluent | 2451189A + 8080019A | Control INGELVAC ® PRRS MLV | 6.0 | 6.1 | 6.2 | 6.3 |
| | | 2451188A + 8080019A | | 6.3 | 6.3 | 6.3 | 6.4 |
| 2 | PPV 27a VP2 + INGEL VAC ® PRRS MLV | 2451189A + 7600016A | Determination of in-use stability for the associated use claim | 6.0 | 6.0 | 6.1 | 6.0 |
| | | 2451188A + 7600018B | | 6.4 | 6.3 | 6.5 | 6.5 |

Example 3

PRRSV-EU Vaccine Effectiveness when PRRSV-EU Vaccine is Mixed with PPV VP2 Vaccine Thirty six (36) non-pregnant, breeding-age gilts were randomized to three treatment groups, each group comprising twelve gilts. Group T01 received control product of WPBS (wash phosphate buffered saline) (control) on days 0 and 21 (DO, D21). Group T02 received REPROCYC® PRRS EU® (PRRS Strain 94881), 3.9 log 10 TCID$_{50}$ per dose, and Porcine Parvovirus vaccine, PPV-27a VP2, 10 μg per dose (mixed) on DO and PPV-27a VP2, 10 μg per dose, only on D21. The REPROCYC® PRRS EU® as a lyophilized cake was reconstituted with the liquid PPV-27a VP2. Group T03 received REPROCYC® PRRS EU® (alone) on DO. Treatments were formulated so that gilts received REPROCYC® PRRS EU® at the minimum immunizing dose and PPV-27a VP2 at the maximum relative potency. Gilts were challenged with 5.5 log$_{10}$TCID$_{50}$/6 mL total dose (2 mL intramuscularly and 2 mL per nostril) heterologous PRRSV EU isolate 190136 four weeks after initial vaccination (D28), and serum samples were collected on the following days: D31, D35, D38, D42 and D49. PRRSV viremia was tested by quantitative PCR (qPCR) [Sandra Revilla-Fernández et al., Journal of Virological Methods 126 (2005) 21-30]. The challenge virus European PRRS virus isolate 190136 was originally obtained from lung tissue of a newborn piglet from a farm showing typical reproductive signs of PRRSV (abortions in sows and weakness in new born piglets) during an outbreak in Lower Saxony, Germany, in April 2004. The attending veterinarians submitted the lung samples to BioScreen (sample arrived on 21 April, 2004) for diagnostic testing. The challenge virus was propagated in AK-MA104 cells and passed twice prior to the challenge.

Post-challenge, both groups (mixed and alone) were shown to be efficacious against virulent PRRSV with quantitative viral load areas under the curve (AUC) for D28 to D49 of 24.36 GE/mL (GE=genomic equivalents) for mixed (p=0.0002) and 32.54 GE/mL for alone (p=0.0045) compared to 50.85 GE/mL in the control. This represents an approximate 50% reduction in systemically circulating virus in the pigs over time for the mixed group and an approximate 40% reduction for the REPROCYC® PRRS EU® alone group (FIG. 1) demonstrating the substantial protective effect of the mixed and alone groups. Additionally, quantitative mean PRRSV qPCR analysis demonstrated significant reductions in PRRSV viral load in for mixed on D35 (p<0.0001) and on D38 (p=0.0052) and in alone for D35 (p<0.0001) compared to the control demonstrating the substantial protective effect of the mixed and alone groups. qPCR analysis showed significant reductions in proportion of positive gilts on D35 for mixed (p=0.0013) and alone (p=0.0046) and on D38 for mixed (p=0.0137) compared to the control. While not statistically significant, a numerical trend toward reduction in mean viral load and proportion PRRSV qPCR positive was observed for mixed on D42 and D49. Similar trends were seen for alone with numerical reduction in mean viral load on D49 and proportion qPCR positive on D42 and D49.

Figure 2:
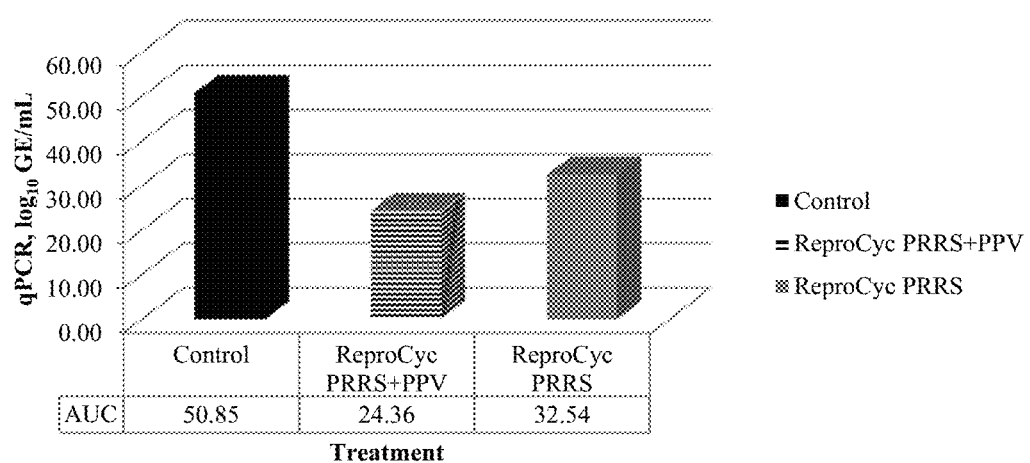
FIG. 2 shows Area Under the Curve (AUC) of PRRSV Viremia (qPCR, $\log_{10}$ GE/mL) by Group.

The use of REPROCYC® PRRS EU® vaccine alone or when mixed with PPV-27a VP2 vaccine was proven efficacious against a virulent PRRSV-EU challenge strain demonstrating a four-week onset of immunity. From the data in FIG. 1 and FIG. 2, it is apparent that mixing REPROCYC® PRRS EU® vaccine with PPV-27a VP2 improved efficacy. The results show a lack of interference between PRRSV component and PPV component in the mixed group demonstrating the advantageous possibility of associated use through mixing.

Example 4

PPV VP2 Vaccine Effectiveness when PRRSV-EU Vaccine is Mixed with PPV VP2 Vaccine Assessment of effectiveness of the combined vaccines: The efficacy of the associated use of both vaccines [REPROCYC® PRRS EU® (PRRS Strain 94881) and PPV-27a VP2] is evaluated against PPV experimental infections.

Efficacy against an experimental challenge with PPV wild strain: The efficacy of the combined vaccines against PPV is evaluated based on the PPV infection in fetus. The vaccine is considered efficacious if ≥80% of fetuses in each treated group are seronegative for PPV.

Animal Care: Animals are in good health and nutritional status before a study is initiated. Prior to the inclusion and the randomization procedure a health examination is conducted. Non-medicated feed is used throughout the duration of the study. Feed rations are appropriate for the age, condition, and species of test animal according to facility standard operations procedure. Water is provided ad libitum throughout the study.

Assessment of the efficacy of the associated use of PPV and PRRSV vaccines after challenge with and heterologous PPV strain: On D0, conventional non-pregnant gilts of 5-6 months of age are randomized equitably to three treatment groups. Group T01 receives 2 mL IM of control product (PBS-CARBOPOL® diluent (IMPRAN FLEX©) on days 0 and 21 (D0, D21). Group T02 receives 2 mL IM of REPROCYC® PRRS EU® (PRRS Strain 94881) and Porcine Parvovirus vaccine, PPV-27a VP2, on D0 and PPV-27a VP2 only on D21. As for Group T02, the REPROCYC® PRRS EU® as a lyophilized cake was reconstituted with the PPV-27a VP2 vaccine solution. Group T03 receives 2 mL IM Porcine Parvovirus vaccine, PPV-27a VP2, (1 µg/dose) on D0 and on D21. The gilts are observed daily for general health. The animals are challenged between day 39 and 42 of gestation with heterologous PPV strain 401/09 (198669) obtained from BioScreen (Minster, Germany) from the tissue of a mummified piglet on 15th June 2004 and sent to Leipzig University, Germany (challenge virus is thawed and diluted in DMEM (1×, Gibco, Ref #11966-025, Lot #1632505) to a target dosage of 6.0 log 10 $TCID_{50}$/6-mL dose). Fetuses are harvested (standard procedure) at around day 90 of gestation and evaluated for the presence of PPV by PCR (Molitor T W et al., Journal of Virological Methods 1991, 32: 201-211) from their organ or tissue fluid samples as well as for their condition, size and weight. Treatments are formulated so that gilts receive REPROCYC® PRRS EU® (PRRS Strain 94881) and Porcine Parvovirus vaccine, PPV-27a VP2, at the maximum REPROCYC® PRRS EU® immunizing dose ($10^{7.0}$ $TCID_{50}$/2-mL dose; geometric mean) and Porcine Parvovirus vaccine, PPV-27a VP2, at the minimum relative potency (1 µg/dose).

The study was valid according to Ph.Eur. Monograph 8.0 04/2013:0965 as the vaccine provided a protection of 95.7% (T03 group) and 94.3% (T02 group), while the T01 group (control) had 91.4% positive fetuses (see Table 2).

It is concluded that vaccination with the PPV vaccine alone or mixed with REPROCYC® PRRS EU® is safe and efficacious when vaccination is completed three weeks before mating.

TABLE 2

Percentage of positive fetuses per group

| Group | N gilts | N fetuses | N pos fetuses | % PPV positives fetus per treatment[1] |
|---|---|---|---|---|
| T01 | 19 | 269 | 246 | 91.4 |
| T02 | 14 | 176 | 10 | 5.7 |
| T03 | 19 | 231 | 10 | 4.3 |

[1]Number of positive PPV fetus/Number of fetus per group.

Example 5

Preparation of Subunit PPV Vaccine

The PPV VP2 antigen is selected to be expressed in baculovirus-infected insect cells based on the German PPV 27a isolate. Porcine parvovirus (PPV) 27a VP2 nucleotide sequence is obtained from Genbank Accession AY684871.1. The PPV 27a VP2 coding region is reverse-translated and codon-optimized for Drosophila (SEQ ID NO:4 and SEQ ID NO:3). The codon-optimized PPV 27a VP2 gene is chemically synthesized at Integrated DNA Technologies. The PPV 27a gene is then subcloned into the baculovirus transfer vector pVL1393, and co-transfected with the linearized baculovirus DiamondBac backbone into Sf9 insect cells to generate recombinant baculovirus containing the PPV 27a VP2 gene under control of the polyhedrin promoter.

When expressed in Sf9 insect cells the PPV VP2 self-assembled into a non-enveloped VLP (data not shown).

The PPV VP2 antigen is adjuvanted with a carbomer (e.g., CARBOPOL®).

Example 6

Proof of Concept Study of the PPV Vaccine

In all animal studies the animals are in good health and nutritional status before the study is initiated. Prior to the randomization procedure a health examination is conducted. Non-medicated feed is used through the duration of the study. Feed rations are appropriate for the age, condition, and species of test animal according to facility standard operating procedure. Water is provided ad libitum throughout the study.

The objective of this vaccination-challenge study is to establish proof of concept dose determination efficacy for a pre-breeding subunit Porcine Parvovirus (PPV) vaccine (see Example 5). Gilts are vaccinated and bred prior to challenge with a live virulent PPV isolate (PPV 002346-5; a North American Strain) at approximately 40 days of gestation (dG). Fetuses are evaluated for PPV infection at approximately 90 dG.

The study design is described in Table 3.

TABLE 3

Study Design

| Treatment | | Vaccination | Insemination | Pregnancy Evaluation | Challenge | Necropsy |
|---|---|---|---|---|---|---|
| T1 | Negative Control | 2 mL on D 0 right neck IM & | D 34-D 42 | D 71 | 6 mL on D 80 (~40 dG) | D 129/130 (~90 dG) |
| T2 | PPV 10 µg | 2 mL on D 21 left neck IM | | | PPV 002346-5 right neck IM and IN | |
| T3 | Positive Control (whole cell inactivated PPV) | | | | | |
| NTX | None | Not applicable | | | Not applicable | D 79 (39 dG) |

NTX = Non-Treated/Non-Challenged Control; IN = intranasal; IM = intramuscular; dG = days of gestation.

Sixty-seven gilts originated from a herd that previously tested negative for PPV with no prior history of reproductive disease or vaccination against PPV were used. Gilts were randomized into 6 treatment groups (T) of n=9 commingled into 3 pens receiving vaccination on D0 and boostered on D21: T1 NC (negative control of water for injection), T2 PPV 10 µg, T3 PC (positive control; whole, inactivated porcine parvovirus (PPV), *Erysipelothrix rhusiopathiae*, *Leptospira canicola*, *L. grippotyphosa*, *L. hardjo*, *L. icterohaemorrhagiae*, and *L. Pomona*; commercially available; used according to manufacturer's manual). Three non-treated control (NTX) gilts were included, one per pen. Post-vaccination, the gilts are synchronized (via administration of MATRIX®; altrenogest, Intervet Schering-Plough Animal Health; per label for 14 consecutive days, D18 to D31) and then bred between D35 and D42. Fifty-four of the 67 gilts become pregnant. On D80 (approximately 40dG), NTX gilts were necropsied, and the remaining gilts were inoculated with 6 mL of PPV strain PPV002346-5 (a North American Strain) at 4.25 $\log_{10}TCID_{50}$ per dose (2 mL intramuscularly and 2 mL per nostril intranasally). Gilts were bled weekly except during synchronization and breeding (D35-D70). Serology is performed on sera from D0, D7, D14, D21, D28 and D73; serology and polymerase chain reaction (PCR) (as described in Jozwik et al. 2009; Journal of General Virology, 90, 2437-2441) for viremia was performed on sera from D80, D87, D94, D101, D108, D115, D122, and D128. Gilts were necropsied on D129 or D130 (approximately 90dG). At necropsy, each reproductive tract was removed, and the position of the fetus in the uterus, the fetal condition, size and weight were recorded. Samples of thoracic wash and lung from each fetus were collected. Thoracic wash samples were collected aseptically from each fetus. Briefly, 3 ml of sterile PBS were injected into the thoracic cavity with a sterile needle and syringe. Fluid was aspirated back into the syringe and injected into an appropriate, sterile SST (serum separator tube) of suitable size. Thoracic washes were tested for the presence of PPV by PCR and for the presence of PPV antibody by hemagglutination inhibition (HI). Lung tissue was stored frozen.

Gilt Viremia (PPV)

All gilts were negative for PPV viremia prior to challenge on D0, D73 (data not shown) and D80 (Table 4). All negative controls are viremic on D87, and 4/7 were viremic on D94.

Post-vaccination T3 gilts seroconvert following booster vaccination. T2 had a serological response to initial vaccination and stayed seropositive after the booster vaccination. T1 control gilts remained serologically negative for PPV until challenge. Post-challenge, all negative control gilts were viremic on D87 (seven days after challenge). One T3 gilt was viremic on D87. All other gilts were not viremic at these time points (see Table 4).

NTX gilts remained seronegative and their fetuses were all PPV negative by PCR on thoracic wash samples.

TABLE 4

Frequency distribution of PPV-positive (PCR) gilts when challenged with PPV at 40 days of gestation (dG) on D 80.

| | | Day of Study (dG = days of gestation) | | | | | | | |
|---|---|---|---|---|---|---|---|---|---|
| | Treatment/Description | D 80 dG 40 | D 87 dG 47 | D 94 dG 54 | D 101 dG 61 | D 108 dG 68 | D 115 dG 75 | D 122 dG 82 | D 128 dG 89 |
| T1 | Negative Control | 0/7 | 7/7 | 4/7 | 0/7 | 0/7 | 0/7 | 0/7 | 0/7 |
| T2 | 10 µg PPV | 0/8 | 0/8 | 0/8 | 0/8 | 0/8 | 0/8 | 0/8 | 0/8 |
| T3 | Positive Control (whole cell inactivated PPV) | 0/9 | 1/9 | 0/9 | 0/9 | 0/9 | 0/8 | 0/8 | 0/8 |
| NTX | None | 0/3 | NA | NA | NA | NA | NA | NA | NA |

NA = not applicable.

Fetus Results

All of the NTX fetuses were considered normal on D80 necropsy (Table 5). At final necropsy on D129 and D130, 22.5% of T1 (Negative Control) fetuses were normal while 98.39% of fetuses in T3 and 97.62% of fetuses in T2 were normal. The average size and weight of T1 (Negative Control) fetuses was 11.5 cm and 168.8 g, respectively, while the average size and weight of fetuses in T2 was 17.5 cm and 590.1 g, respectively.

All T4 (NTX) fetuses were PPV negative determined by PCR on thoracic wash samples (see Table 3). PPV infection was confirmed in 67/80 T1 Negative Control fetuses (83.75%). Sixty-two of the 67 Negative Control fetuses confirmed to be PPV infected were mummies. In contrast, PPV infection was confirmed only in 0.79% in T2 fetuses.

Based on the conclusion parameter for establishing efficacy as stated in the European Pharmacopoeia (monograph 01/2008:0965), all vaccines (including the Positive Control (whole cell inactivated PPV)) meet criteria for protection from infection (>80% fetuses negative for PPV).

TABLE 5

Litter details: number, size, weight and condition of fetuses and laboratory confirmation of PPV infection (PCR on thoracic wash samples).

| Treatment | T1 | T2 | T3 | T4 |
|---|---|---|---|---|
| Description | NC | PPV 10 µg | Positive Control (whole cell inactivated PPV) | NTX * |
| # of gilts | 5 | 8 | 9 | 3 |
| Total # fetuses | 80 | 126 | 124 | 44 |
| Avg. litter size | 16.0 | 15.8 | 13.8 | 14.7 |
| Fetal Condition: | | | | |
| Mummies | 62 | 3 | 2 | 0 |
| Normal | 18 | 123 | 122 | 44 |
| % Normal | 22.50 | 97.62 | 98.39 | 100.0 |
| Average size (cm) | 11.5 | 17.5 | 17.8 | 6.0 |
| Average weight (g) | 168.8 | 590.1 | 580.3 | 11.9 |
| Laboratory Confirmation of PPV Infection: | | | | |
| # PPV+ fetuses | 67 | 1 | 3 | 0 |
| % positive | 83.75 | 0.79 | 2.42 | 0.0 |
| % protected | 16.25 | 99.21 | 97.58 | |

* NTX fetuses necropsied at 50 days of gestation
NC = Negative Control

Conclusion: The PPV vaccine of the present invention showed protection of fetuses after virulent heterologous PPV challenge. The study results show that the vaccine is safe when administered pre-breeding and efficacious in significantly reducing viremia, and transplacental infection in fetuses. Further, it has been shown that the vaccine protect against a heterologous North American PPV challenge strain. Furthermore, it has been shown that the subunit PPV VP2 protein is as efficacious as the whole killed virus.

Example 7

Establishing the Minimum Immunizing Dose of the PPV Vaccine—Protection Against Heterologous Us PPV Strain The objective of this vaccination-challenge study is to establish the minimum immunizing dose (MID) for the Porcine Parvovirus (PPV) vaccine. Gilts were challenged with a live virulent PPV serotype 1 isolate (PPV 002346-5) at approximately 40 days of gestation (dG). A vaccine is considered efficacious if ≥80% of fetuses in the vaccinated group are negative for PPV after challenge. Supportive parameters include fetus size, weight and condition, gilt viremia status post-challenge and gilt serological status.

Gilts (with no prior history of reproductive disease or vaccination against PPV) were randomized into treatment groups: T01 negative control (Product matched placebo (PMP)) and T02=1.0 μg PPV/2 mL dose). Non-treated/non-challenged (NTX) gilts were randomly assigned to pens as controls for general health status.

Gilts were given 2 mL of the appropriate treatment intramuscularly on DO and D21. Post-vaccination, gilts were bred between D37 and D50, and then evaluated for pregnancy status on D74. On D81, gestating gilts were challenged with 6.77 $\log_{10}TCID_{50}$/6 mL of PPV serotype 1 intramuscularly and intranasally. Gilts were bled weekly except during estrus synchronization and breeding (D36-D73). Hemagglutination Inhibition (HI) assays were performed on sera from D7, D14, D21, D28 and D35; HI and polymerase chain reaction (PCR) (see Example 6) for viremia were performed on sera from D-3, D74, D80, D88, D95, D102 and D127. Gilts were necropsied on D128 and D129 (approximately 90 dG). At necropsy, the reproductive tract of each sow was removed, and the position of each fetus in the uterus, the fetal condition, size and weight was recorded. Thoracic wash samples (see Example 6) were collected from each fetus and tested for the presence of PPV by PCR.

Gilt Viremia (PPV)

The vaccines are considered safe since animals show no abnormal body temperature 24 hours or 48 hours post-vaccination, no abnormal local reactions attributable to the vaccine and no clinical signs related to vaccination (data not shown).

All gilts were negative for PPV viremia prior to vaccination, prior to challenge on D74, and on D80. Thus, post-vaccination, no clinical signs related to vaccine administration were observed. On D88, all ten T01 gilts were viremic, and all vaccinated gilts were negative. All other blood samples on D95, D102 and D127 were negative for PPV viremia for all treatment groups (Table 6).

TABLE 6

Frequency distribution of PPV-positive (PCR) gilts when challenged with PPV at ~40 days of gestation (dG) on D 81.

| | | Day of Study/Days of Gestation (dG) | | | | | |
|---|---|---|---|---|---|---|---|
| Treatment/Description | | D 74 dG 32 | D 80 dG 38 | D 88 dG 46 | D 95 dG 53 | D 102 dG 60 | D 127 dG 85 |
| T01 | Negative Control | 0/12 | 0/12 | 10/10* | 0/10 | 0/10 | 0/10 |
| T02 | PPV (1.0 μg/dose) | 0/12 | 0/12 | 0/12 | 0/12 | 0/12 | 0/12 |

*2 gilts have been diagnosed as not pregnant and, therefore, removed from the group Fetus Results At final necropsy on D128 and D129, 38% of T01 (Negative Control) fetuses were normal condition while 95% of fetuses in the vaccine group were normal condition. The average size and weight of T01 (Negative Control) fetuses was 14.4 cm and 245.9 g, respectively, while the average size and weight of fetuses from the vaccinated dams was 19.3 cm and 550 g, respectively (Table 7). Thus, the vaccine group meets the criteria for protection from infection with PPV as the conclusion parameter for PPV efficacy established by the Ph. Eur. 01/2008:0965 is >80% fetuses in a treatment group must be negative for PPV.

PPV infection was confirmed in 113/146 of Negative Control (T01) fetuses (77%). However, PPV infection in the vaccinated group (T02) was only 10%.

TABLE 7

Litter details: number, size, weight and condition of fetuses and laboratory confirmation of PPV infection (PCR on thoracic wash samples).

| Treatment | T01 | T02 |
|---|---|---|
| Description | Negative Control | PPV 1 µg |
| # of gilts | 10 | 11 |
| Total # fetuses | 146 | 148 |
| Avg. litter size | 14.6 | 13.5 |
| Fetal Condition: | | |
| # Necrotic (%) | 9 (6%) | 0 (0%) |
| # Mummies (%) | 82 (56%) | 8 (5%) |
| # Normal (%) | 55 (38%) | 140 (95%) |
| Average size (cm) | 14.4 | 19.3 |
| Average weight (g) | 245.9 | 550.0 |
| Laboratory Confirmation of PPV Infection: | | |
| # Thoracic wash positive fetuses (%) | 113 (77%) | 15 (10%) |
| % protected | | 90% |

# = number,
% = percent

Conclusion: The PPV VP2 subunit vaccine of the present invention shows protection of fetuses after challenge with a virulent heterologous PPV. This study results reveal that the vaccine is safe and efficacious in preventing viremia in gilts and PPV infection in fetuses when using only 1 µg of PPV VP2 subunit vaccine. Further, it is shown that the vaccine protects against a heterologous North American challenge strain.

Example 8

Establishing the Minimum Immunizing Dose of the PPV Vaccine—Protection Against Heterologous EU PPV Strain The objective of this study is to evaluate the onset of immunity of the Porcine Parvovirus Vaccine (PPV VP2, called PPV vaccine from here on). In addition, safety and efficacy was evaluated using a randomized, blinded, negative controlled vaccination—challenge study design.

Gilts were randomly assigned to three groups. In groups 1 and 2 gilts were vaccinated twice, with a three week interval (on D0 and D21). The second dose was given three weeks before mating. All treatments were administered by the intramuscular (IM) route in a 2 mL volume. Group 2 received the PPV vaccine, whereas group 1 was the placebo group which received a sterile diluent as control product and group 3 served as strict control, without any treatment.

The gilts were estrus synchronized and three weeks after the second vaccination they were artificially inseminated. Animals that got pregnant were challenged on D84 between the 39th and 42nd day of gestation with a virulent, heterologous PPV strain.

On D132-135, at about the 90th day of gestation, the gilts were euthanized, necropsied and the fetuses were evaluated.

TABLE 8

Study Design

| Group | 1st Treatment D 0 (2 mL right side of neck IM) | 2nd Treatment D 21 (2 mL left side of neck IM) | Challenge D 84 6.0 Log$_{10}$TCID$_{50}$/ 6 mL) dose (~40 dG) 2 mL right neck IM and 2 mL per nostril intranasal | Necropsy |
|---|---|---|---|---|
| 1 (Negative Control) | Control Product | Control Product | PPV EU Strain 401/09 (198669) | D 132 to D 135 |
| 2 | PPV (1 µg/dose) | PPV (1 µg/dose) | PPV EU Strain 401/09 (198669) | D 132 to D 135 |
| 3 (Strict Control) | — | — | No Challenge | D 83 |

Evaluation of PPV viremia in gilts pre- and post-challenge by PCR:

All animals were negative for PPV by PCR at D-6 and D-1 before vaccination fulfilling the inclusion criteria. Post vaccination all animals in the strict control and control product group were negative for PPV antigen until challenge, therefore, a PPV infection before challenge can be excluded.

Viremia was investigated at 7 (D90), 14 (D97) and 21 (D104) days post challenge and at the day of necropsy. After challenge no viremia was detected in the vaccinated animals, viremia occurred only in the non-vaccinated control animals.

On D90, (7 days post challenge) already 95% of the non-vaccinated control animals were positive for PPV. On D97 still 60% of these animals had a positive result while on D104 all animals were tested negative for PPV. In contrast, in the vaccinated group all animals tested on day D90, D97 or D104 were negative for PPV.

TABLE 9

Number of animals with viremia after challenge

| | 7 days post challenge (D 90) | 14 days post challenge (D 97) | 21 days post challenge (D 104) |
|---|---|---|---|
| Control | 19/20 (95%) | 12/20 (60%) | 0/20 |
| PPV | 0/20 | 0/20 | 0/20 |

Fetus Results

The percentage of PPV infected fetus was of 91.4% in the Control group, but only 4.3% in the PPV group (see Table 10).

TABLE 10

Percentage of positive fetuses per group and litter size

| Group | N gilts | N fetuses | N positive fetuses | % PPV positive (PCR) fetuses per treatment[1] | N Average litter size | Min % positive fetuses per litter | Max % positive fetuses per litter |
|---|---|---|---|---|---|---|---|
| Control | 19 | 269 | 246 | 91.4 | 14.2 | 57 | 100 |
| PPV | 19 | 231 | 10 | 4.3 | 12.2 | 0 | 20 |

[1]Number of positive PPV fetuses/Number of fetuses per group.
N Total number

Evaluation of Condition of Fetuses

All fetuses were evaluated for their condition and allocated to three categories: normal, mummified and autolyzed.

The majority of mummified and autolyzed fetuses were found in the control group. Only 39.8% of fetuses in this group were of normal condition while in the vaccinated groups 97.4% (PPV group) of fetuses had a normal condition (see Table 11).

TABLE 11

Fetal condition

| | Fetal condition | | | |
|---|---|---|---|---|
| Group | [% normal] | [% autolyzed] | [% mummified] | [N (total)] |
| Control | 39.8% | 12.3% | 48.0% | 269 |
| PPV | 97.4% | 0.9% | 1.7% | 231 |

Conclusion: The PPV vaccine of the present invention shows protection of fetuses after virulent heterologous PPV challenge indicating that the vaccine is safe and efficacious in preventing viremia and PPV infection in fetuses when using only 1 µg of vaccine. Further, it has been shown that the vaccine also protects against a heterologous European challenge strain of PPV. Thus, the vaccine has a broad protection spectrum as the vaccine protects against heterologous North American as well as heterologous European challenge strains.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the following claims.

Example 9

Porcine Parvovirus (PPV) Proof of Concept/Vaccine Dose Determination of PPV Subunit Combination Vaccine with *Erysipelothrix rhusiopathiae* and/or Porcine Reproductive and Respiratory Syndrome Virus in Breeding Age Gilts The objective of this vaccination-challenge study is to provide data on the associated use of INGELVAC® PRRSV MLV with an experimental subunit Porcine Parvovirus (PPV) combination vaccine with *Erysipelothrix rhusiopathiae* (Ery) bacterin and was to establish proof of concept dose determination of efficacy for a PPV combination vaccine with Ery bacterin in 5- to 6-month-old gilts.

Sixty-seven gilts originated from a herd previously tested negative for PPV with no prior PPV history of disease or vaccination. Gilts were randomized into 6 treatment groups of n=9 commingled into 3 pens receiving vaccination on D0 and boostered on D21: T1 Negative Control, T2 PPV 10 µg, T3 PPV 0.1 µg+Ery 10 logs, T4 PPV 1.0 µg+Ery 10 logs, T5 PPV 10 µg+Ery 10 logs, T6 Positive Control (FARROWSURE® GOLD (Zoetis Services LLC). Three non-treated control (NTX) gilts were included, one per pen. In addition, ten gilts were housed in a separate building receiving T7 PPV 10 µg+Ery 10 logs used to rehydrate INGELVAC® PRRSV MLV to assess PPV efficacy when combined with the commercially available Porcine Reproductive and Respiratory Syndrome (PRRS) vaccine. T7 is the group of interest for this Example 9.

Gilts were vaccinated and mated; 54 of the 67 gilts became pregnant. At approximately 40 days of gestation (dG), NTX gilts were necropsied, and the remaining gilts were inoculated with 6 mL of PPV strain PPV002346-5 at 4.25 $\log_{10}\text{TCID}_{50}$ per dose (2 mL intramuscularly and 2 mL per nostril intranasally. Gilts were bled weekly except during synchronization and breeding (D35-D70), and sera was tested as described in Table 12.

TABLE 12

Samples and Laboratory Testing, Gilts

| Sample | Day of Sample Collection | Test Type | Test |
|---|---|---|---|
| Serum | Pre-screen | SIV Serology | HI |
| Serum | All: D 0, D 73. T7 only: D 21, D 80, D 128 | PRRSV erology | ELISA |
| Serum | D 0, D 80, D 87, D 94, D 101, D 108, D 115, D 122, D 128 | PPV Gilt Serology | HI |
| Serum | D 0, D 7, D 14, D 21, D 28, D 73, D 80, D 94, D 101, D 108, D 115, D 122, D 128 | PPV Gilt Viremia | PCR |

Gilts were necropsied on D129 or D130 (~90dG). At necropsy, each reproductive tract was removed, and the position of the fetus in the uterus, the fetal condition, size and weight were recorded. Samples of thoracic wash and lung from each fetus were collected. Thoracic washes were tested for the presence of PPV by PCR and for the presence of PPV antibody by hemagglutination inhibition (HI). Lung tissue was stored frozen.

T7 gilts had a serological response to vaccination and were not viremic post-challenge. At necropsy, 97.37% (111/114) of T7 fetuses were normal condition, and only one fetus tested positive for PPV. In contrast, all T1 gilts were seronegative during the vaccination phase and seroconverted and became viremic post-challenge. At necropsy, only 22.50% (18/80) of T1 fetuses were normal condition, and 83.75% (67/80) tested positive for PPV infection by PCR of thoracic wash fluid. In conclusion, the combination vaccine (PPV 10 µg+Ery) with INGELVAC® PRRS MLV was efficacious in preventing viremia and PPV infection of fetuses at 40dG.

Study Design:

each necropsy, the reproductive tract was removed, and fetuses were delivered aseptically via caesarean. Fetuses were identified by a fetus ID composed of the gilt ID then a letter (R for "right horn" or L for left horn) and then the number as the fetus is encountered from the uterine bifurcation. The fetal condition (normal or mummy), size and weight were recorded.

Fetal Sample Collection: To prevent cross-contamination of samples, all appropriate techniques were used to sterilize

TABLE 13

Study Design

| Treatment | # | Vaccination | Insemination | Pregnancy Evaluation | Challenge | Necropsy |
|---|---|---|---|---|---|---|
| T1 | Negative Control | 9 | 2 mL on D 0 right neck IM & | D 34-D 42 | D 71 | 6 mL on D 80 | D 129/130 (~90 dG) |
| T2 | PPV 10 µg | 9 | 2 mL on D 21 | | | (~40 dG) | |
| T3 | PPV 0.1 µg + Ery | 9 | (no PRRSV) left neck IM | | | PPV 002346-5 | |
| T4 | PPV 1.0 µg + Ery | 9 | | | | right neck IM and IN | |
| T5 | PPV 10 µg + Ery | 9 | | | | | |
| T6 | FARROW®SURE GOLD | 9 | | | | | |
| T7 | PPV 10 µg + Ery + Ingelvac PRRS MLV | 10 | | | | | |
| NTX | None | 3 | Not applicable | | | Not applicable | D 79 (39 dG) |

# = number;
NTX = Non-Treated/Non-Challenged Control; IN = intranasal; IM = intramuscular; dG = days of gestation Materials:

Control Product: The control product administered to the Negative Control (T1) animals was sterile diluent (lot #240) prepared using water for injection (WFI) from purified water at BIVI, St. Joseph Mo., USA. The control product was supplied as a 100-mL fill volume presentation in plastic bottles. A 2-mL dose was applied in the right neck muscle on D0 with a 2-mL booster applied in the left neck muscle on D21.

Vaccine: The combination vaccine of interest for T7 was an experimental subunit PPV combination vaccine with Ery bacterin used as a diluent to rehydrate INGELVAC® PRRS MLV. Serial #311-171 was targeted at a 10 µg/dose for PPV in combination with a 10 logs/dose of killed Ery bacterin provided in plastic bottles containing 20 mL (10 doses). A single bottle of Serial #311-171 was used to rehydrate a single bottle of a commercial serial of INGELVAC® PRRS MLV, Serial #245-B53. A 2-mL dose was applied in the right neck muscle on D0 with a 2-mL booster applied in the left neck muscle on D21.

Challenge Material: The challenge material was prepared prior to the challenge event. PPV strain 002346-5 was targeted at 5 $\log_{10}TCID_{50}$ per dose, 6 mL dose (assigned lot #354-021) and kept on ice during the challenge event. The challenge titers were determined by $TCID_{50}$ assay on retained post-challenge material held at 4° C. The final titer of the challenge material was 3.47 logs/mL or 4.25 logs/6 mL dose. On D80, all gilts were inoculated with 2 mL of challenge material per each nostril in addition to 2 mL intramuscularly in the right neck.

Methods:

Necropsy and Fetal Evaluation: On D79, all NTX gilts were euthanized by intravenous barbiturate injection, and on D129 and D130, all remaining gilts were euthanized. For or clean work areas and utensils between handling each fetus and each sample both at necropsy and in the laboratory. Samples were labeled with the fetus ID, sample type, study day and the collection date. At the earliest possible time on the day of collection, samples were transported on ice and processed using proper techniques to prevent cross-contamination while aliquoting each sample into appropriately-sized and appropriately-labeled tubes. One aliquot was submitted to ISU-VDL. The presence of virus was measured on each sample by PCR. Remaining aliquots were stored at −70° C.

Thoracic Wash Collection: As aseptically as possible, a thoracic wash was collected from each fetus. Briefly, 3 mL of sterile PBS was injected into the thoracic cavity with a sterile needle and syringe. As much of the fluid as possible was aspirated back into the syringe and was then injected into an appropriate-sized SST.

Statistical Methods:

EXPERIMENTAL UNIT: The gilt was the experimental unit for T1-T6. In the case where comparisons were made with T7, the room was the experimental unit with the understanding that the housing of T7 was separate from the other treatment groups.

Justification for number of animals: The European Pharmacopoeia required at least seven vaccinated gilts and five control gilts to be challenged (EPh 01/2008:0965). Nine or ten gilts were sourced for each treatment to account for gilts failing to conceive.

Randomization: Prior to the start of the study, the Statistician was supplied with gilt ID numbers and randomized gilts to pen and treatment completely at random. Three gilts were randomized to the NTX group, ten gilts were randomized to the T7 group and the remaining gilts were randomized equally to T1, T2, T3, T4, T5 and T6 groups. T1-6 gilts and NTX gilts were equally divided between three pens in Barn 1. T7 gilts were individually housed in pens in Barn 2.

Blinding Criteria: Throughout the study, any personnel involved in collecting data or performing laboratory assays was masked to the allocation of gilts to treatment groups T1, T2, T3, T4, T5 and T6. Since T7 and NTX gilts were housed separately and serum was tested for PRRSV antibody, personnel could not be blinded to these two groups. Treatments were administered by an individual not involved with data collection.

Data Management: All data was imported into SAS version 9.2 (Cary, USA/North Carolina, SAS Institute Inc.) for management and analyses.

Results:

Only comparisons for the Negative Control (T1) compared to the PPV 10 µg+Ery 10 logs used to rehydrate INGELVAC® PRRSV MLV group (T7) are presented in this study summary, and data for T1, T7 and NTX groups are presented.

Gilt Results: On D0, all gilts were serologically negative for PRRSV by ELISA. On D21, D80 and D128, all T7 gilts were seropositive for PRRSV. On D73, all T7 gilts were seropositive, and gilts in all other treatment groups were seronegative.

Geometric mean PPV HI titers for T7 became and stayed seropositive after the booster vaccination on D21 whereas geometric mean PPV HI titers for T1 and NTX treatments remained seronegative (<100) during the vaccination phase. After D80 when T1 and T7 gilts were challenged with PPV, both groups were seropositive.

All gilts were negative for PPV viremia prior to challenge on D0, D73 (data not shown) and D80 ([0432]). All negative controls were viremic on D87, and 4/7 were viremic on D94.

TABLE 15

Litter details: number, size, weight and condition of fetuses and laboratory confirmation of PPV infection (PCR on thoracic wash samples).

| Treatment | T1 | T7 | NTX* |
|---|---|---|---|
| Description | Negative Control | PPV/Ery/PRRS | NTX* |
| Number of gilts | 5 | 8 | 3 |
| Total number fetuses | 80 | 114 | 44 |
| Average litter size | 16.0 | 14.3 | 14.7 |
| Fetal Condition: | | | |
| Mummies | 62 (77.50%) | 3 (0.63%) | 0 (0.0%) |
| Normal | 18 (22.50%) | 111 (97.37%) | 44 (100%) |
| Average size | 11.5 cm | 17.8 cm | 6.0 cm |
| Average weight | 168.8 g | 576.3 g | 11.9 g |
| Laboratory Confirmation of PPV infection (PCR results) | | | |
| PCR positive fetuses | 67 (83.75%) | 1 (0.88%) | 0 (0.0%) |
| % protected | 13 (16.25%) | 113 (99.12%) | |

*NTX fetuses necropsied at 50 days of gestation
PPV/Ery/PRRS = 10 µg PPV +10 log *Erysipelothrix rhusiopathiae* bacterin used to rehydrate Ingelvac ® PRRS MLV

DISCUSSION/CONCLUSION

NTX gilts remained seronegative, and their fetuses were all PPV negative by PCR on thoracic wash samples.

Gilts administered T7 (10 µg PPV+Ery+PRRSV) had a serological response to initial vaccination and stayed sero-

TABLE 14

Frequency distribution of PPV-positive (PCR) gilts when challenged with PPV at 40 days of gestation (dG) on D 80.

| | | Day of Study (dG = days of gestation) | | | | | | | |
|---|---|---|---|---|---|---|---|---|---|
| Treatment/Description | | D 80 dG 40 | D 87 dG 47 | D 94 dG 54 | D 101 dG 61 | D 108 dG 68 | D 115 dG 75 | D 122 dG 82 | D 128 dG 89 |
| T1 | Negative Control | 0/7 | 7/7 | 4/7 | 0/7 | 0/7 | 0/7 | 0/7 | 0/7 |
| T7 | 10 µg PPV/Ery/PRRS | 0/9 | 0/9 | 0/9 | 0/9 | 0/9 | 0/9 | 0/9 | 0/9 |
| NTX | None | 0/3 | NA | NA | NA | NA | NA | NA | NA |

NA = not applicable; Ery = 10 log *Erysipelothrix rhusiopathiae* bacterin; PRRS = Ingelvac ® PRRS MLV Fetus Results: All of the NTX fetuses were considered normal on D80 necropsy ([0437]). At final necropsy on D129 and D130, 22.5% of T1 (Negative Control) fetuses were normal while 99.12% of fetuses in T7 were normal. The average size and weight of T1 (Negative Control) fetuses was 11.5 cm and 168.8 g, respectively, while the average size and weight of fetuses in T7 was 17.8 cm and 576.3 g, respectively.

All NTX fetuses were PPV negative determined by PCR on thoracic wash samples. PPV infection was confirmed in 67/80 T1 Negative Control fetuses (83.75%). Sixty-two of the 67 Negative Control fetuses confirmed to be PPV infected were mummies. The 18 normal-appearing fetuses were all from the same litter, and only five of these 18 fetuses were confirmed to be PPV positive. For T7, only one pig was infected for <1% infection rate.

positive after the booster vaccination. No T7 gilts were viremic on the weekly sampling points post-challenge. At necropsy, 97.37% (111/114) of T7 fetuses were normal condition, and only one fetus tested positive for PPV infection by PCR of thoracic wash fluid. In contrast, gilts administered T1 (Negative Control) were seronegative during the vaccination phase, and post-challenge, all gilts seroconverted and became viremic. The average size and average weight of T1 fetuses were substantially less than T7 averages. At necropsy, only 22.50% (18/80) of T1 fetuses were normal condition, and 83.75% (67/80) tested positive for PPV infection by PCR of thoracic wash fluid.

In conclusion, the combination vaccine (PPV 10 µg+Ery) with PRRS MLV was efficacious in preventing viremia and PPV infection of fetuses at 40dG.

SEQUENCE LISTING

SEQ ID NO:4 is a codon-optimized PPV 27a VP2 nucleotide sequence which was further modified to have two ClaI restriction enzyme sites (amino acid position 25 is an isoleucine residue, amino acid position 36 is a serine residue, amino acid position 37 is an isoleucine residue) so as to flank the VP2 coding region comprised of Glycine repeats. However, the ClaI sites were introduced in a manner so as to not disrupt the VP2 coding region. SEQ ID NO:2 is the protein sequence corresponding to SEQ ID NO:4. SEQ ID NO:3 is a codon-optimized PPV 27a VP2 nucleotide sequence (without ClaI restriction enzyme sites). SEQ ID NO:1 is the protein sequence corresponding to SEQ ID NO:3. SEQ ID NO: 5 to 16 disclose further PPV VP2 protein sequences with (SEQ ID NO: 5 to 10) or without (SEQ ID NO: 11 to 16) ClaI sites. SEQ ID NO:17 corresponds to PRRSV Lelystad wild-type sequence and SEQ ID NO:18 corresponds to PRRSV VR2332 wild-type sequence.

What is claimed is:

1. A method of producing an immunogenic composition comprising a recombinant protein, wherein the method comprises the steps in the following order:
   (i) providing/obtaining a mixture comprising
      a first liquid,
      recombinant protein and/or quaternary structures composed of a plurality of said recombinant protein, and
      a vector comprising a nucleic acid sequence encoding said recombinant protein;
   (ii) adding a second liquid to the mixture of step (i), wherein the second liquid is different from the first liquid;
   (iii) washing the recombinant protein and/or quaternary structures composed of a plurality of said recombinant protein in the mixture by further adding additional second liquid to the mixture resulting from step (ii) and removing a portion of the first and/or second liquid from such combined mixture;
   (iv) inactivating the vector by adding an inactivating agent to the mixture resulting from step (iii);

(v) neutralizing the inactivating agent by adding a neutralizing agent to the mixture resulting from step (iv); and
(vi) wherein said recombinant protein is a porcine parvovirus virus (PPV) VP2 protein comprising or consisting of a sequence having at least 99.5% sequence identity with the sequence of SEQ ID NO:2.

2. The method of claim 1, wherein the mixture of step (i) is obtainable by a procedure comprising the steps of:
(a) permitting infection of susceptible cells in culture with a vector comprising a nucleic acid sequence encoding said recombinant protein and/or quaternary structures composed of a plurality of said recombinant protein, wherein said recombinant protein and/or quaternary structures composed of a plurality of said recombinant protein is expressed by said vector, and then
(b) recovering the recombinant protein and/or quaternary structures composed of a plurality of said recombinant protein from the cell culture, wherein cell debris is separated from the recombinant protein and/or quaternary structures composed of a plurality of said recombinant protein via a separation step.

3. The method according to claim 2, wherein cell debris separation step (b) further comprises including a micro filtration through at least one filter, wherein the at least one filter has a pore size larger than the recombinant protein and/or quaternary structures composed of a plurality of said recombinant protein.

4. The method of claim 3, wherein the separation step (b) comprises:
a micro filtration through at least one filter having a pore size of about 2 μm to about 4 μm, and/or
a micro filtration through at least one filter having a pore size of about 0.1 μm to about 0.8 μm.

5. The method of claim 2, wherein the cell culture in step (a) is maintained at 27±2° C., while the recombinant protein and/or quaternary structures composed of a plurality of said recombinant protein is expressed by said vector.

6. The method of claim 5, wherein the recovering in step (b) occurs 6 to 8 days after inoculation of the cells with the vector.

7. The method of claim 1, wherein said first liquid comprises a portion of cell culture medium, and wherein the cell culture medium is insect cell culture medium.

8. The method of claim 1, wherein said recombinant protein further comprising a PPV VP2 protein comprising or consisting of a sequence having at least 70% sequence identity with the sequence of SEQ ID NO:1 and/or SEQ ID NOS 5 to 16.

9. The method of claim 1, wherein said quaternary structures composed of a plurality of said recombinant protein are virus-like particles or wherein said quaternary structures composed of a plurality of said recombinant protein are homotrimers.

10. The method of claim 1, wherein the vector is a recombinant virus, and/or wherein the nucleic acid sequence is a DNA sequence.

11. The method of claim 1, wherein the vector comprising a nucleic acid encoding said recombinant protein and/or quaternary structures composed of a plurality of said recombinant protein is a recombinant baculovirus, wherein said baculovirus comprises a DNA sequence encoding said recombinant protein and/or quaternary structures composed of a plurality of said recombinant protein.

12. The method of claim 11, wherein the mixture of step (i) is obtainable by a procedure comprising the steps of:

(a) permitting infection of susceptible cells in culture with a vector comprising a nucleic acid sequence encoding said recombinant protein and/or quaternary structures composed of a plurality of said recombinant protein, wherein said recombinant protein and/or quaternary structures composed of a plurality of said recombinant protein is expressed by said vector, and (b) recovering the recombinant protein and/or quaternary structures composed of a plurality of said recombinant protein from the cell culture, wherein cell debris is separated from the recombinant protein and/or quaternary structures composed of a plurality of said recombinant protein via a separation step.

13. The method of claim 1, wherein in step (iii) said recombinant protein and/or said quaternary structures composed of a plurality of said recombinant protein is washed with at least 2×, of second liquid, in comparison to the original volume of said recombinant protein and/or said quaternary structures composed of a plurality of said recombinant protein in the mixture of step (i).

14. The method of claim 1, wherein in step (iii) such washing step(s) is performed at a temperature of lower than 37° C.

15. The method of claim 1, wherein in step (iii) the portion of the first and/or second liquid is removed from the mixture by filtration, wherein a filter is utilized comprising a semi-permeable membrane having an average pore size that is smaller than said recombinant protein and/or said quaternary structures composed of a plurality of said recombinant protein and/or prevents passage of the majority of proteins of 20 kDa to 500 kDa, in size through the semi-permeable membrane.

16. The method of claim 1, wherein the second liquid is a buffer solution of wash phosphate buffered saline (WPBS).

17. The method of claim 1, wherein the volume of the second liquid added in step (ii) is about the volume of the first and/or second liquid removed in step (iii) and no concentration step is performed.

18. The method of claim 1, wherein the inactivating agent is an aziridine compound and the inactivating agent is added in a molar excess in relation to the vector.

19. The method of claim 1, wherein the neutralizing agent is sodium thiosulfate and the neutralizing agent is added in a molar excess in relation to the inactivating agent.

20. The method of claim 1, wherein said method further comprises the step of admixing the mixture remaining after step (v) with a further component selected from the group consisting of pharmaceutically acceptable carriers, adjuvants, diluents, excipients, and combinations thereof.

21. The method according to claim 1, wherein the virucidal activity of the mixture resulting from said method is reduced by at least 10% as compared to the mixture that has not undergone said method, and/or wherein a live virus is mixed with the immunogenic composition for two or more hours, wherein the immunogenic composition produced by said method causes a loss of less than 1 log TCID50 per mL of the live virus.

22. The method according to claim 21, wherein the live virus is Porcine Reproductive and Respiratory Syndrome (PRRS) virus.

23. The method according to claim 1, wherein the method further comprises the step (vi) of harvesting the recombinant protein and/or the quaternary structures composed of a plurality of said recombinant protein remaining after step (v), and in particular further comprising the step of purifying the harvest comprising the recombinant protein and/or the quaternary structures composed of a plurality of said recombinant protein, by chromatographic procedure.

24. The method according to claim 23, further comprising the step of purifying the harvest comprising the recombinant protein and/or the quaternary structures composed of a plurality of said recombinant protein, by chromatographic procedure.

25. The method according to claim 24, wherein the method further comprises the step of combining the purified harvested recombinant protein and/or the quaternary structures composed of a plurality of said recombinant protein with at least one additional antigen.

26. The method according to claim 25, wherein the at least one additional antigen is Porcine Reproductive and Respiratory Syndrome (PRRS) virus.

27. The method according to claim 23, wherein the chromatographic procedure is size exclusion chromatography.

* * * * *

```
                        SEQUENCE LISTING

<160> NUMBER OF SEQ ID NOS: 18

<210> SEQ ID NO 1
<211> LENGTH: 579
<212> TYPE: PRT
<213> ORGANISM: Porcine parvovirus

<400> SEQUENCE: 1

Met Ser Glu Asn Val Glu Gln His Asn Pro Ile Asn Ala Gly Thr Glu
1               5                   10                  15

Leu Ser Ala Thr Gly Asn Glu Ser Gly Gly Gly Gly Gly Gly Gly Gly
            20                  25                  30

Gly Arg Gly Ala Gly Gly Val Gly Val Ser Thr Gly Ser Phe Asn Asn
        35                  40                  45

Gln Thr Glu Phe Gln Tyr Leu Gly Glu Gly Leu Val Arg Ile Thr Ala
    50                  55                  60

His Ala Ser Arg Leu Ile His Leu Asn Met Pro Glu His Glu Thr Tyr
65                  70                  75                  80

Lys Arg Ile His Val Leu Asn Ser Glu Ser Gly Val Ala Gly Gln Met
                85                  90                  95

Val Gln Asp Asp Ala His Thr Gln Met Val Thr Pro Trp Ser Leu Ile
            100                 105                 110

Asp Ala Asn Ala Trp Gly Val Trp Phe Asn Pro Ala Asp Trp Gln Leu
        115                 120                 125

Ile Ser Asn Asn Met Thr Glu Ile Asn Leu Val Ser Phe Glu Gln Glu
    130                 135                 140

Ile Phe Asn Val Val Leu Lys Thr Ile Thr Glu Ser Ala Thr Ser Pro
145                 150                 155                 160

Pro Thr Lys Ile Tyr Asn Asn Asp Leu Thr Ala Ser Leu Met Val Ala
                165                 170                 175

Leu Asp Thr Asn Asn Thr Leu Pro Tyr Thr Pro Ala Ala Pro Arg Ser
            180                 185                 190

Glu Thr Leu Gly Phe Tyr Pro Trp Leu Pro Thr Lys Pro Thr Gln Tyr
        195                 200                 205

Arg Tyr Tyr Leu Ser Cys Thr Arg Asn Leu Asn Pro Pro Thr Tyr Thr
    210                 215                 220

Gly Gln Ser Glu Gln Ile Thr Asp Ser Ile Gln Thr Gly Leu His Ser
225                 230                 235                 240

Asp Ile Met Phe Tyr Thr Ile Glu Asn Ala Val Pro Ile His Leu Leu
                245                 250                 255

Arg Thr Gly Asp Glu Phe Ser Thr Gly Ile Tyr His Phe Asp Thr Lys
            260                 265                 270

Pro Leu Lys Leu Thr His Ser Trp Gln Thr Asn Arg Ser Leu Gly Leu
        275                 280                 285

Pro Pro Lys Leu Leu Thr Glu Pro Thr Thr Glu Gly Asp Gln His Pro
    290                 295                 300
```

-continued

Gly Thr Leu Pro Ala Ala Asn Thr Arg Lys Gly Tyr His Gln Thr Ile
305                 310                 315                 320

Asn Asn Ser Tyr Thr Glu Ala Thr Ala Ile Arg Pro Ala Gln Val Gly
            325                 330                 335

Tyr Asn Thr Pro Tyr Met Asn Phe Glu Tyr Ser Asn Gly Gly Pro Phe
        340                 345                 350

Leu Thr Pro Ile Val Pro Thr Ala Asp Thr Gln Tyr Asn Asp Asp Glu
    355                 360                 365

Pro Asn Gly Ala Ile Arg Phe Thr Met Gly Tyr Gln His Gly Gln Leu
370                 375                 380

Thr Thr Ser Ser Gln Glu Leu Glu Arg Tyr Thr Phe Asn Pro Gln Ser
385                 390                 395                 400

Lys Cys Gly Arg Ala Pro Lys Gln Gln Phe Asn Gln Gln Ser Pro Leu
            405                 410                 415

Asn Leu Gln Asn Thr Asn Asn Gly Thr Leu Leu Pro Ser Asp Pro Ile
        420                 425                 430

Gly Gly Lys Thr Asn Met His Phe Met Asn Thr Leu Asn Thr Tyr Gly
    435                 440                 445

Pro Leu Thr Ala Leu Asn Asn Thr Ala Pro Val Phe Pro Asn Gly Gln
450                 455                 460

Ile Trp Asp Lys Glu Leu Asp Thr Asp Leu Lys Pro Arg Leu His Val
465                 470                 475                 480

Thr Ala Pro Phe Val Cys Lys Asn Asn Pro Pro Gly Gln Leu Phe Val
            485                 490                 495

Lys Ile Ala Pro Asn Leu Thr Asp Asp Phe Asn Ala Asp Ser Pro Gln
        500                 505                 510

Gln Pro Arg Ile Ile Thr Tyr Ser Asn Phe Trp Trp Lys Gly Thr Leu
    515                 520                 525

Thr Phe Thr Ala Lys Met Arg Ser Ser Asn Met Trp Asn Pro Ile Gln
530                 535                 540

Gln His Thr Thr Thr Ala Glu Asn Ile Gly Asn Tyr Ile Pro Thr Asn
545                 550                 555                 560

Ile Gly Gly Ile Lys Met Phe Pro Glu Tyr Ser Gln Leu Ile Pro Arg
            565                 570                 575

Lys Leu Tyr

<210> SEQ ID NO 2
<211> LENGTH: 579
<212> TYPE: PRT
<213> ORGANISM: Porcine parvovirus

<400> SEQUENCE: 2

Met Ser Glu Asn Val Glu Gln His Asn Pro Ile Asn Ala Gly Thr Glu
1               5                   10                  15

Leu Ser Ala Thr Gly Asn Glu Ser Ile Gly Gly Gly Gly Gly Gly Gly
            20                  25                  30

Gly Arg Gly Ser Ile Gly Val Gly Val Ser Thr Gly Ser Phe Asn Asn
        35                  40                  45

Gln Thr Glu Phe Gln Tyr Leu Gly Glu Gly Leu Val Arg Ile Thr Ala
    50                  55                  60

His Ala Ser Arg Leu Ile His Leu Asn Met Pro Glu His Glu Thr Tyr
65                  70                  75                  80

Lys Arg Ile His Val Leu Asn Ser Glu Ser Gly Val Ala Gly Gln Met
            85                  90                  95

-continued

```
Val Gln Asp Asp Ala His Thr Gln Met Val Thr Pro Trp Ser Leu Ile
            100                 105                 110
Asp Ala Asn Ala Trp Gly Val Trp Phe Asn Pro Ala Asp Trp Gln Leu
            115                 120                 125
Ile Ser Asn Asn Met Thr Glu Ile Asn Leu Val Ser Phe Glu Gln Glu
            130                 135                 140
Ile Phe Asn Val Val Leu Lys Thr Ile Thr Glu Ser Ala Thr Ser Pro
145                 150                 155                 160
Pro Thr Lys Ile Tyr Asn Asn Asp Leu Thr Ala Ser Leu Met Val Ala
                165                 170                 175
Leu Asp Thr Asn Asn Thr Leu Pro Tyr Thr Pro Ala Ala Pro Arg Ser
            180                 185                 190
Glu Thr Leu Gly Phe Tyr Pro Trp Leu Pro Thr Lys Pro Thr Gln Tyr
            195                 200                 205
Arg Tyr Tyr Leu Ser Cys Thr Arg Asn Leu Asn Pro Pro Thr Tyr Thr
            210                 215                 220
Gly Gln Ser Glu Gln Ile Thr Asp Ser Ile Gln Thr Gly Leu His Ser
225                 230                 235                 240
Asp Ile Met Phe Tyr Thr Ile Glu Asn Ala Val Pro Ile His Leu Leu
                245                 250                 255
Arg Thr Gly Asp Glu Phe Ser Thr Gly Ile Tyr His Phe Asp Thr Lys
            260                 265                 270
Pro Leu Lys Leu Thr His Ser Trp Gln Thr Asn Arg Ser Leu Gly Leu
            275                 280                 285
Pro Pro Lys Leu Leu Thr Glu Pro Thr Thr Glu Gly Asp Gln His Pro
290                 295                 300
Gly Thr Leu Pro Ala Ala Asn Thr Arg Lys Gly Tyr His Gln Thr Ile
305                 310                 315                 320
Asn Asn Ser Tyr Thr Glu Ala Thr Ala Ile Arg Pro Ala Gln Val Gly
                325                 330                 335
Tyr Asn Thr Pro Tyr Met Asn Phe Glu Tyr Ser Asn Gly Gly Pro Phe
            340                 345                 350
Leu Thr Pro Ile Val Pro Thr Ala Asp Thr Gln Tyr Asn Asp Asp Glu
            355                 360                 365
Pro Asn Gly Ala Ile Arg Phe Thr Met Gly Tyr Gln His Gly Gln Leu
            370                 375                 380
Thr Thr Ser Ser Gln Glu Leu Glu Arg Tyr Thr Phe Asn Pro Gln Ser
385                 390                 395                 400
Lys Cys Gly Arg Ala Pro Lys Gln Gln Phe Asn Gln Ser Pro Leu
                405                 410                 415
Asn Leu Gln Asn Thr Asn Asn Gly Thr Leu Leu Pro Ser Asp Pro Ile
            420                 425                 430
Gly Gly Lys Thr Asn Met His Phe Met Asn Thr Leu Asn Thr Tyr Gly
            435                 440                 445
Pro Leu Thr Ala Leu Asn Asn Thr Ala Pro Val Phe Pro Asn Gly Gln
            450                 455                 460
Ile Trp Asp Lys Glu Leu Asp Thr Asp Leu Lys Pro Arg Leu His Val
465                 470                 475                 480
Thr Ala Pro Phe Val Cys Lys Asn Asn Pro Pro Gly Gln Leu Phe Val
                485                 490                 495
Lys Ile Ala Pro Asn Leu Thr Asp Asp Phe Asn Ala Asp Ser Pro Gln
            500                 505                 510
```

```
Gln Pro Arg Ile Ile Thr Tyr Ser Asn Phe Trp Lys Gly Thr Leu
        515                 520                 525

Thr Phe Thr Ala Lys Met Arg Ser Ser Asn Met Trp Asn Pro Ile Gln
    530                 535                 540

Gln His Thr Thr Thr Ala Glu Asn Ile Gly Asn Tyr Ile Pro Thr Asn
545                 550                 555                 560

Ile Gly Gly Ile Lys Met Phe Pro Glu Tyr Ser Gln Leu Ile Pro Arg
                565                 570                 575

Lys Leu Tyr

<210> SEQ ID NO 3
<211> LENGTH: 1760
<212> TYPE: DNA
<213> ORGANISM: Porcine parvovirus

<400> SEQUENCE: 3
```

| | | | | | |
|---|---|---|---|---|---|
| ggatccgcca | ccatgtccga | gaacgtggag | cagcacaacc | cgataaacgc | aggcacagag | 60 |
| ctgtcggcga | ctggcaatga | gagcggaggc | ggaggcggcg | gaggaggtgg | acgcggcgca | 120 |
| ggcggagtgg | gcgtttcgac | cggaagcttc | aataatcaaa | ccgagtttca | gtacctgggc | 180 |
| gagggtttgg | tgcggattac | ggctcacgcg | tcccgactga | tacatctcaa | tatgccggag | 240 |
| catgagacct | acaagcgtat | ccatgtcctg | aactcggaat | cgggcgtcgc | cggtcagatg | 300 |
| gtccaagatg | atgctcatac | tcagatggtg | acacctgga | gcttgataga | tgccaacgca | 360 |
| tggggcgtgt | ggttcaaccc | tgcggattgg | cagctgataa | gcaataacat | gacagaaatc | 420 |
| aatttggtta | gtttcgagca | agagatattt | aatgtcgtgc | tgaaaaccat | cacagagagc | 480 |
| gccacgagcc | ccccgacgaa | gatttacaat | aacgacctga | cggcgtcctt | gatggtcgcc | 540 |
| ttggacacaa | taacaccct | cccgtacacc | cccgcggccc | cccgcagcga | gaccctgggc | 600 |
| ttttatccct | ggctgcccac | caagccaacg | cagtatcgct | actacctgag | ttgtacacga | 660 |
| aatttgaatc | cgccgacata | cactggtcag | tcggagcaga | tcacggacag | cattcaaacg | 720 |
| ggcctgcact | ccgatatcat | gttttacacg | atagagaacg | cagtacccat | ccacctgctg | 780 |
| cgtacgggag | atgagttctc | gaccggtatc | tatcattttg | cacaaaaacc | cttgaaattg | 840 |
| acgcacagtt | ggcaaaccaa | tcgctcgctg | ggcttgcccc | caaagttgtt | gacggaaccc | 900 |
| accaccgagg | tgaccaaca | cccaggcact | ctccccgcag | caaataccg | caagggctat | 960 |
| catcaaacga | tcaacaatag | ctataccgag | gctaccgcca | ttcggccagc | acaggtggga | 1020 |
| tacaacacac | cttacatgaa | ctttgaatac | tccaacggcg | gccgttcct | gaccccgata | 1080 |
| gttccgaccg | ccgacactca | gtacaacgat | gacgagccga | acggcgccat | caggtttacc | 1140 |
| atgggctatc | agcacggtca | attgacaact | cgtcgcaag | aactggaacg | ctatacattc | 1200 |
| aaccctcaga | gtaagtgtgg | ccgggcaccc | aaacaacagt | tcaaccagca | atccccactg | 1260 |
| aacctgcaga | ataccaacaa | tggcacgctg | ctgccatccg | atcccattgg | aggaaagacc | 1320 |
| aacatgcatt | tcatgaacac | gctgaataca | tacgaccac | tgaccgccct | gaacaatacc | 1380 |
| gcacccgtct | tccctaatgg | ccagatctgg | gataaagagc | tggatacgga | cctgaagccc | 1440 |
| cgactccacg | tgactgcgcc | ctttgtgtgc | aaaaataacc | caccgggaca | gttgttcgtc | 1500 |
| aaaatagccc | ccaacttgac | cgacgacttc | aatgcagaca | gccctcagca | gccgcgaatc | 1560 |
| atcacctatt | cgaacttctg | gtggaagggc | acgctgactt | tcacggctaa | gatgcgctcg | 1620 |
| agcaatatgt | ggaaccccaat | ccagcaacat | accacaaccg | ctgaaaatat | tggcaattac | 1680 |
| atccctacga | atataggcgg | aataaagatg | tttccggagt | attcccagct | cattccacgc | 1740 |

<210> SEQ ID NO 4
<211> LENGTH: 1760
<212> TYPE: DNA
<213> ORGANISM: Porcine parvovirus

<400> SEQUENCE: 4

```
ggatccgcca ccatgtccga gaacgtggag cagcacaacc cgataaacgc aggcacagag     60
ctgtcggcga ctggcaatga atcgatcggc ggaggcggcg gaggaggtgg acgcggatcg    120
atcggagtgg gcgtttcgac cggaagcttc aataatcaaa ccgagtttca gtacctgggc    180
gagggtttgg tgcggattac ggctcacgcg tcccgactga tacatctcaa tatgccggag    240
catgagacct acaagcgtat ccatgtcctg aactcggaat cgggcgtcgc cggtcagatg    300
gtccaagatg atgctcatac tcagatggtg acaccctgga gcttgataga tgccaacgca    360
tggggcgtgt ggttcaaccc tgcggattgg cagctgataa gcaataacat gacagaaatc    420
aatttggtta gtttcgagca agagatattt aatgtcgtgc tgaaaaccat cacagagagc    480
gccacgagcc ccccgacgaa gatttacaat aacgacctga cggcgtcctt gatggtcgcc    540
ttggacacaa ataacaccct cccgtacacc cccgcggccc ccgcagcga ccctgggc       600
tttatccct ggctgcccac caagccaacg cagtatcgct actacctgag ttgtacacga    660
aatttgaatc cgccgacata cactggtcag tcggagcaga tcacggacag cattcaaacg    720
ggcctgcact ccgatatcat gttttacacg atagagaacg cagtacccat ccacctgctg    780
cgtacgggag atgagttctc gaccggtatc tatcattttg acacaaaacc cttgaaattg    840
acgcacagtt ggcaaaccaa tcgctcgctg ggcttgcccc caaagttgtt gacggaaccc    900
accaccgagg gtgaccaaca cccaggcact ctccccgcag caaatacccg caagggctat    960
catcaaacga tcaacaatag ctataccgag gctaccgcca ttcggccagc acaggtggga   1020
tacaacacac cttacatgaa cttttgaatac tccaacggcg gcccgttcct gaccccgata   1080
gttccgaccg ccgacactca gtacaacgat gacgagccga acggcgccat caggtttacc   1140
atgggctatc agcacggtca attgacaact tcgtcgcaag aactggaacg ctatacattc   1200
aaccctcaga gtaagtgtgg ccgggcaccc aaacaacagt tcaaccagca atccccactg   1260
aacctgcaga ataccaacaa tggcacgctg ctgccatccg atcccattgg aggaaagacc   1320
aacatgcatt tcatgaacac gctgaataca tacggaccac tgaccgccct gaacaatacc   1380
gcaccgtct tccctaatgg ccagatctgg gataaagagc tggatacgga cctgaagccc   1440
cgactccacg tgactgcgcc ctttgtgtgc aaaaataacc caccgggaca gttgttcgtc   1500
aaaatagccc ccaacttgac cgacgacttc aatgcagaca gccctcagca gccgcgaatc   1560
atcacctatt cgaacttctg gtggaagggc acgctgactt tcacggctaa gatgcgctcg   1620
agcaatatgt ggaacccaat ccagcaacat accacaaccg ctgaaaatat tggcaattac   1680
atccctacga atataggcgg aataaagatg tttccggagt attcccagct cattccacgc   1740
aagctgtatt aagcggccgc                                                1760
```

<210> SEQ ID NO 5
<211> LENGTH: 579
<212> TYPE: PRT
<213> ORGANISM: Porcine parvovirus

<400> SEQUENCE: 5

```
Met Ser Glu Asn Val Glu Gln His Asn Pro Ile Asn Ala Gly Thr Glu
1               5                   10                  15

Leu Ser Ala Thr Gly Asn Glu Ser Ile Gly Gly Gly Gly Gly Gly Gly
                20                  25                  30

Gly Arg Gly Ser Ile Gly Val Gly Val Ser Thr Gly Ser Phe Asn Asn
            35                  40                  45

Gln Thr Glu Phe Gln Tyr Leu Gly Glu Gly Leu Val Arg Ile Thr Ala
        50                  55                  60

His Ala Ser Arg Leu Ile His Leu Asn Met Pro Glu His Glu Thr Tyr
65                  70                  75                  80

Lys Arg Ile His Val Leu Asn Ser Glu Ser Gly Val Ala Gly Gln Met
                85                  90                  95

Val Gln Asp Asp Ala His Thr Gln Met Val Thr Pro Trp Ser Leu Ile
            100                 105                 110

Asp Ala Asn Ala Trp Gly Val Trp Phe Asn Pro Ala Asp Trp Gln Leu
        115                 120                 125

Ile Ser Asn Asn Met Thr Glu Ile Asn Leu Val Ser Phe Glu Gln Ala
        130                 135                 140

Ile Phe Asn Val Val Leu Lys Thr Ile Thr Glu Ser Ala Thr Ser Pro
145                 150                 155                 160

Pro Thr Lys Ile Tyr Asn Asn Asp Leu Thr Ala Ser Leu Met Val Ala
                165                 170                 175

Leu Asp Thr Asn Asn Thr Leu Pro Tyr Thr Pro Ala Ala Pro Arg Ser
            180                 185                 190

Glu Thr Leu Gly Phe Tyr Pro Trp Leu Pro Thr Lys Pro Thr Gln Tyr
        195                 200                 205

Arg Tyr Tyr Leu Ser Cys Ile Arg Asn Leu Asn Pro Pro Thr Tyr Thr
210                 215                 220

Gly Gln Ser Glu Gln Ile Thr Asp Ser Ile Gln Thr Gly Leu His Ser
225                 230                 235                 240

Asp Ile Met Phe Tyr Thr Ile Glu Asn Ala Val Pro Ile His Leu Leu
                245                 250                 255

Arg Thr Gly Asp Glu Phe Ser Thr Gly Ile Tyr His Phe Asp Thr Lys
            260                 265                 270

Pro Leu Lys Leu Thr His Ser Trp Gln Thr Asn Arg Ser Leu Gly Leu
        275                 280                 285

Pro Pro Lys Leu Leu Thr Glu Pro Thr Thr Glu Gly Asp Gln His Pro
        290                 295                 300

Gly Thr Leu Pro Ala Ala Asn Thr Arg Lys Gly Tyr His Gln Thr Thr
305                 310                 315                 320

Asn Asn Ser Tyr Thr Glu Ala Thr Ala Ile Arg Pro Ala Gln Val Gly
                325                 330                 335

Tyr Asn Thr Pro Tyr Met Asn Phe Glu Tyr Ser Asn Gly Gly Pro Phe
            340                 345                 350

Leu Thr Pro Ile Val Pro Thr Ala Asp Thr Gln Tyr Asn Asp Asp Glu
        355                 360                 365

Pro Asn Gly Ala Ile Arg Phe Thr Met Asp Tyr Gln His Gly Gln Leu
        370                 375                 380

Thr Thr Ser Ser Gln Glu Leu Glu Arg Tyr Thr Phe Asn Pro Gln Ser
385                 390                 395                 400

Lys Cys Gly Arg Ala Pro Lys Gln Gln Phe Asn Gln Gln Ser Pro Leu
                405                 410                 415

Asn Leu Gln Asn Thr Asn Asn Gly Thr Leu Leu Pro Ser Asp Pro Ile
```

```
                420              425              430
Gly Gly Lys Thr Asn Met His Phe Met Asn Thr Leu Asn Thr Tyr Gly
            435              440              445

Pro Leu Thr Ala Leu Asn Asn Thr Ala Pro Val Phe Pro Asn Gly Gln
450              455              460

Ile Trp Asp Lys Glu Leu Asp Thr Asp Leu Lys Pro Arg Leu His Val
465              470              475              480

Thr Ala Pro Phe Val Cys Lys Asn Asn Pro Pro Gly Gln Leu Phe Val
            485              490              495

Lys Ile Ala Pro Asn Leu Thr Asp Asp Phe Asn Ala Asp Ser Pro Gln
            500              505              510

Gln Pro Arg Ile Ile Thr Tyr Ser Asn Phe Trp Trp Lys Gly Thr Leu
            515              520              525

Thr Phe Thr Ala Lys Met Arg Ser Ser Asn Met Trp Asn Pro Ile Gln
            530              535              540

Gln His Thr Thr Thr Ala Glu Asn Ile Gly Asn Tyr Ile Pro Thr Asn
545              550              555              560

Ile Gly Gly Ile Arg Met Phe Pro Glu Tyr Ser Gln Leu Ile Pro Arg
            565              570              575

Lys Leu Tyr

<210> SEQ ID NO 6
<211> LENGTH: 579
<212> TYPE: PRT
<213> ORGANISM: Porcine parvovirus

<400> SEQUENCE: 6

Met Ser Glu Asn Val Glu Gln His Asn Pro Ile Asn Ala Gly Thr Glu
1               5               10              15

Leu Ser Ala Thr Gly Asn Glu Ser Ile Gly Gly Gly Gly Gly Gly Gly
            20              25              30

Gly Arg Gly Ser Ile Gly Val Gly Val Ser Thr Gly Ser Phe Asn Asn
            35              40              45

Gln Thr Glu Phe Gln Tyr Leu Gly Glu Gly Leu Val Arg Ile Thr Ala
50              55              60

His Ala Ser Arg Leu Ile His Leu Asn Met Pro Glu His Glu Thr Tyr
65              70              75              80

Lys Arg Ile His Val Leu Asn Ser Glu Ser Gly Val Ala Gly Gln Met
            85              90              95

Val Gln Asp Asp Ala His Thr Gln Met Val Thr Pro Trp Ser Leu Ile
            100             105             110

Asp Ala Asn Ala Trp Gly Val Trp Phe Asn Pro Ala Asp Trp Gln Leu
            115             120             125

Ile Ser Asn Asn Met Thr Glu Ile Asn Leu Val Ser Phe Glu Gln Glu
130             135             140

Ile Phe Asn Val Val Leu Lys Thr Ile Thr Glu Ser Ala Thr Ser Pro
145             150             155             160

Pro Thr Lys Ile Tyr Asn Asn Asp Leu Thr Ala Ser Leu Met Val Ala
            165             170             175

Leu Asp Thr Asn Asn Thr Leu Pro Tyr Thr Pro Ala Ala Pro Arg Ser
            180             185             190

Glu Thr Leu Gly Phe Tyr Pro Trp Leu Pro Thr Lys Pro Thr Gln Tyr
            195             200             205

Arg Tyr Tyr Leu Ser Cys Thr Arg Asn Leu Asn Pro Pro Thr Tyr Thr
```

```
            210                 215                 220
Gly Gln Ser Glu Gln Ile Thr Asp Ser Ile Gln Thr Gly Leu His Ser
225                 230                 235                 240

Asp Ile Met Phe Tyr Thr Ile Glu Asn Ala Val Pro Ile His Leu Leu
                245                 250                 255

Arg Thr Gly Asp Glu Phe Ser Thr Gly Ile Tyr His Phe Asp Thr Lys
                260                 265                 270

Pro Leu Lys Leu Thr His Ser Trp Gln Thr Asn Arg Ser Leu Gly Leu
            275                 280                 285

Pro Pro Lys Leu Leu Thr Glu Pro Thr Thr Glu Gly Asp Gln His Pro
290                 295                 300

Gly Thr Leu Pro Ala Ala Asn Thr Arg Lys Gly Tyr His Gln Thr Ile
305                 310                 315                 320

Asn Asn Ser Tyr Thr Glu Ala Thr Ala Ile Arg Pro Ala Gln Val Gly
                325                 330                 335

Tyr Asn Thr Pro Tyr Met Asn Phe Glu Tyr Ser Asn Gly Gly Pro Phe
                340                 345                 350

Leu Thr Pro Ile Val Pro Thr Ala Asp Thr Gln Tyr Asn Asp Asp Glu
            355                 360                 365

Pro Asn Gly Ala Ile Arg Phe Thr Met Gly Tyr Gln His Gly Gln Leu
            370                 375                 380

Thr Thr Ser Ser Gln Glu Leu Glu Arg Tyr Thr Phe Asn Pro Gln Ser
385                 390                 395                 400

Lys Cys Gly Arg Ala Pro Lys Gln Gln Phe Asn Gln Gln Ser Pro Leu
                405                 410                 415

Asn Leu Gln Asn Thr Asn Asn Gly Thr Leu Leu Pro Ser Asp Pro Ile
            420                 425                 430

Gly Gly Lys Thr Asn Met His Phe Met Asn Thr Leu Asn Thr Tyr Gly
            435                 440                 445

Pro Leu Thr Ala Leu Asn Asn Thr Ala Pro Val Phe Pro Asn Gly Gln
            450                 455                 460

Ile Trp Asp Lys Glu Leu Asp Thr Asp Leu Lys Pro Arg Leu His Val
465                 470                 475                 480

Thr Ala Pro Phe Val Cys Lys Asn Asn Pro Pro Gly Gln Leu Phe Val
                485                 490                 495

Lys Ile Ala Pro Asn Leu Thr Asp Asp Phe Asn Ala Asp Ser Pro Gln
                500                 505                 510

Gln Pro Arg Ile Ile Thr Tyr Ser Asn Phe Trp Trp Lys Gly Thr Leu
            515                 520                 525

Thr Phe Thr Ala Lys Met Arg Ser Ser Asn Met Trp Asn Pro Ile Gln
            530                 535                 540

Gln His Thr Thr Ala Glu Asn Ile Gly Asn Tyr Ile Pro Thr Asn
545                 550                 555                 560

Ile Gly Gly Ile Lys Met Phe Pro Glu Tyr Ser Gln Leu Ile Pro Arg
                565                 570                 575

Lys Leu Tyr

<210> SEQ ID NO 7
<211> LENGTH: 579
<212> TYPE: PRT
<213> ORGANISM: Porcine parvovirus

<400> SEQUENCE: 7

Met Ser Glu Asn Val Glu Gln His Asn Pro Ile Asn Ala Gly Thr Glu
```

```
1               5                   10                  15
Leu Ser Ala Thr Gly Asn Glu Ser Ile Gly Gly Gly Gly Gly Gly
                20                  25                  30
Gly Arg Gly Ser Ile Gly Val Gly Val Ser Thr Gly Ser Phe Asn Asn
                35                  40                  45
Gln Thr Glu Phe Gln Tyr Leu Gly Glu Gly Leu Val Arg Ile Thr Ala
        50                  55                  60
His Ala Ser Arg Leu Ile His Leu Asn Met Pro Glu His Glu Thr Tyr
65                  70                  75                  80
Lys Arg Ile His Val Leu Asn Ser Glu Ser Gly Val Ala Gly Gln Met
                85                  90                  95
Val Gln Asp Asp Ala His Thr Gln Met Val Thr Pro Trp Ser Leu Ile
                100                 105                 110
Asp Ala Asn Ala Trp Gly Val Trp Phe Asn Pro Ala Asp Trp Gln Leu
                115                 120                 125
Ile Ser Asn Asn Met Thr Glu Ile Asn Leu Val Ser Phe Glu Gln Glu
                130                 135                 140
Ile Phe Asn Val Val Leu Lys Thr Ile Thr Glu Ser Ala Thr Ser Pro
145                 150                 155                 160
Pro Thr Lys Ile Tyr Asn Asn Asp Leu Thr Ala Ser Leu Met Val Ala
                165                 170                 175
Leu Asp Thr Asn Asn Thr Leu Pro Tyr Thr Pro Ala Ala Pro Arg Ser
                180                 185                 190
Glu Thr Leu Gly Phe Tyr Pro Trp Leu Pro Thr Lys Pro Thr Gln Tyr
                195                 200                 205
Arg Tyr Tyr Leu Ser Cys Thr Arg Asn Leu Asn Pro Pro Thr Tyr Thr
210                 215                 220
Gly Gln Ser Glu Gln Ile Thr Asp Ser Ile Gln Thr Gly Leu His Ser
225                 230                 235                 240
Asp Ile Met Phe Tyr Thr Ile Glu Asn Ala Val Pro Ile His Leu Leu
                245                 250                 255
Arg Thr Gly Asp Glu Phe Ser Thr Gly Ile Tyr His Phe Asp Thr Lys
                260                 265                 270
Pro Leu Lys Leu Thr His Ser Trp Gln Thr Asn Arg Ser Leu Gly Leu
                275                 280                 285
Pro Pro Lys Leu Leu Thr Glu Pro Thr Glu Gly Asp Gln His Pro
                290                 295                 300
Gly Thr Leu Pro Ala Ala Asn Thr Arg Lys Gly Tyr His Gln Thr Ile
305                 310                 315                 320
Asn Asn Ser Tyr Thr Glu Ala Thr Ala Ile Arg Pro Ala Gln Val Gly
                325                 330                 335
Tyr Asn Thr Pro Tyr Met Asn Phe Glu Tyr Ser Asn Gly Gly Pro Phe
                340                 345                 350
Phe Ile Pro Ile Val Pro Thr Ala Asp Thr Gln Tyr Asn Asp Asp Glu
                355                 360                 365
Pro Asn Gly Gly Ile Arg Phe Thr Met Gly Tyr Gln His Gly Gln Leu
                370                 375                 380
Ile Thr Ser Ser Gln Glu Val Glu Arg Tyr Thr Phe Asn Pro Gln Arg
385                 390                 395                 400
Lys Cys Gly Arg Gly Ala Lys Gln Gln Phe Asn Gln Ser Pro Leu
                405                 410                 415
Asn Ile Gln Asn Thr Asn Asn Gly Thr Ile Leu Pro Ser Asp Pro Ile
                420                 425                 430
```

```
Gly Gly Lys Thr Asn Met His Phe Met Asn Thr Pro Asn Thr Tyr Gly
            435                 440                 445

Pro Leu Thr Ala Val Asn Asn Thr Ala Pro Val Phe Pro Asn Gly Gln
        450                 455                 460

Ile Trp Asp Lys Glu Leu Asp Thr Asp Leu Lys Pro Arg Leu His Val
465                 470                 475                 480

Thr Ala Pro Phe Val Cys Lys Asn Asn Pro Pro Gly Gln Leu Phe Val
                485                 490                 495

Lys Ile Ala Pro Asn Leu Thr Asp Asp Phe Asn Ala Asp Ser Pro Gln
                500                 505                 510

Gln Pro Arg Ile Ile Thr Tyr Ser Asn Phe Trp Trp Lys Gly Thr Leu
            515                 520                 525

Thr Phe Thr Ala Lys Met Arg Ser Ser Asn Met Trp Asn Pro Ile Gln
        530                 535                 540

Gln His Thr Thr Thr Ala Glu Asn Ile Gly Asn Tyr Ile Pro Thr Asn
545                 550                 555                 560

Ile Gly Gly Ile Lys Met Phe Pro Glu Tyr Ser Gln Leu Ile Pro Arg
                565                 570                 575

Lys Leu Tyr

<210> SEQ ID NO 8
<211> LENGTH: 579
<212> TYPE: PRT
<213> ORGANISM: Porcine parvovirus

<400> SEQUENCE: 8

Met Ser Glu Asn Val Glu Gln His Asn Pro Ile Asn Ala Gly Thr Glu
1               5                   10                  15

Leu Ser Ala Thr Gly Asn Glu Ser Ile Gly Gly Gly Gly Gly Gly Gly
            20                  25                  30

Gly Arg Gly Ser Ile Gly Val Gly Val Ser Thr Gly Ser Phe Asn Asn
        35                  40                  45

Gln Thr Glu Phe Gln Tyr Leu Gly Glu Gly Leu Val Arg Ile Thr Ala
    50                  55                  60

His Ala Ser Arg Leu Ile His Leu Asn Met Pro Glu His Glu Thr Tyr
65                  70                  75                  80

Lys Arg Ile His Val Leu Asn Ser Glu Ser Gly Val Ala Gly Gln Met
                85                  90                  95

Val Gln Asp Asp Ala His Thr Gln Met Val Thr Pro Trp Ser Leu Ile
            100                 105                 110

Asp Ala Asn Ala Trp Gly Val Trp Phe Asn Pro Ala Asp Trp Gln Leu
        115                 120                 125

Ile Ser Asn Asn Met Thr Glu Ile Asn Leu Val Ser Phe Glu Gln Ala
    130                 135                 140

Ile Phe Asn Val Val Leu Lys Thr Ile Thr Glu Ser Ala Thr Ser Pro
145                 150                 155                 160

Pro Thr Lys Ile Tyr Asn Asn Asp Leu Thr Ala Ser Leu Met Val Ala
                165                 170                 175

Leu His Thr Asn Asn Thr Leu Pro Tyr Thr Pro Ala Ala Pro Arg Ser
            180                 185                 190

Glu Thr Leu Gly Phe Tyr Pro Trp Leu Pro Thr Lys Pro Thr Gln Tyr
        195                 200                 205

Arg Tyr Tyr Leu Ser Cys Ile Arg Asn Leu Asn Pro Pro Thr Tyr Thr
    210                 215                 220
```

```
Gly Gln Ser Glu Gln Ile Thr Asp Ser Ile Gln Thr Gly Leu His Ser
225                 230                 235                 240

Asp Ile Met Phe Tyr Thr Ile Glu Asn Ala Val Pro Ile His Leu Leu
            245                 250                 255

Arg Thr Gly Asp Glu Phe Ser Thr Gly Ile Tyr His Phe Asp Thr Lys
        260                 265                 270

Pro Leu Lys Leu Thr His Ser Trp Gln Thr Asn Arg Ser Leu Gly Leu
    275                 280                 285

Pro Pro Lys Leu Leu Thr Glu Pro Thr Thr Glu Gly Asp Gln His Pro
290                 295                 300

Gly Thr Leu Pro Ala Ala Asn Thr Arg Lys Gly Tyr His Gln Thr Ile
305                 310                 315                 320

Asn Asn Ser Tyr Thr Glu Ala Thr Ala Ile Arg Pro Ala Gln Val Gly
                325                 330                 335

Tyr Asn Thr Pro Tyr Met Asn Phe Glu Tyr Ser Asn Gly Gly Pro Phe
            340                 345                 350

Leu Thr Pro Ile Val Pro Thr Ala Asp Thr Gln Tyr Asn Asp Asp Glu
        355                 360                 365

Pro Asn Gly Ala Ile Arg Phe Thr Met Asp Tyr Gln His Gly His Leu
    370                 375                 380

Thr Thr Ser Ser Gln Glu Leu Glu Arg Tyr Thr Phe Asn Pro Gln Ser
385                 390                 395                 400

Lys Cys Gly Arg Thr Pro Lys Gln Gln Phe Asn Gln Ser Pro Leu
                405                 410                 415

Asn Leu Gln Asn Thr Asn Asn Gly Thr Leu Leu Pro Ser Asp Pro Ile
            420                 425                 430

Gly Gly Lys Thr Asn Met His Phe Met Asn Thr Leu Asn Thr Tyr Gly
        435                 440                 445

Pro Leu Thr Ala Leu Asn Asn Thr Ala Pro Val Phe Pro Asn Gly Gln
    450                 455                 460

Ile Trp Asp Lys Glu Leu Asp Thr Asp Leu Lys Pro Arg Leu His Val
465                 470                 475                 480

Thr Ala Pro Phe Val Cys Lys Asn Asn Pro Pro Gly Gln Leu Phe Val
                485                 490                 495

Lys Ile Ala Pro Asn Leu Thr Asp Asp Phe Asn Ala Asp Ser Pro Gln
            500                 505                 510

Gln Pro Arg Ile Ile Thr Tyr Ser Asn Phe Trp Trp Lys Gly Thr Leu
        515                 520                 525

Thr Phe Thr Ala Lys Met Arg Ser Ser Asn Met Trp Asn Pro Ile Gln
    530                 535                 540

Gln His Thr Thr Thr Ala Glu Asn Ile Gly Lys Tyr Ile Pro Thr Asn
545                 550                 555                 560

Ile Gly Gly Ile Lys Met Phe Pro Glu Tyr Ser Gln Leu Ile Pro Arg
                565                 570                 575

Lys Leu Tyr

<210> SEQ ID NO 9
<211> LENGTH: 579
<212> TYPE: PRT
<213> ORGANISM: Porcine parvovirus

<400> SEQUENCE: 9

Met Ser Glu Asn Val Glu Gln His Asn Pro Ile Asn Ala Gly Thr Glu
1               5                   10                  15
```

```
Leu Ser Ala Thr Gly Asn Glu Ser Ile Gly Gly Gly Gly Gly
            20                  25                  30

Gly Arg Gly Ser Ile Gly Val Gly Val Ser Thr Gly Ser Phe Asn Asn
        35                  40                  45

Gln Thr Glu Phe Gln Tyr Leu Gly Glu Gly Leu Val Arg Ile Thr Ala
50                      55                  60

His Ala Ser Arg Leu Ile His Leu Asn Met Pro Glu His Glu Thr Tyr
65                      70                  75                  80

Lys Arg Ile His Val Leu Asn Ser Glu Ser Gly Val Ala Gly Gln Met
                    85                  90                  95

Val Gln Asp Asp Ala His Thr Gln Met Val Thr Pro Trp Ser Leu Ile
                100                 105                 110

Asp Ala Asn Ala Trp Gly Val Trp Phe Asn Pro Ala Asp Trp Gln Leu
            115                 120                 125

Ile Ser Asn Asn Met Thr Glu Ile Asn Leu Val Ser Phe Glu Gln Glu
130                 135                 140

Ile Phe Asn Val Val Leu Lys Thr Ile Thr Glu Ser Ala Thr Ser Pro
145                 150                 155                 160

Pro Thr Lys Ile Tyr Asn Asn Asp Leu Thr Ala Ser Leu Met Val Ala
                165                 170                 175

Leu Asp Thr Asn Asn Thr Leu Pro Tyr Thr Pro Ala Ala Pro Arg Ser
            180                 185                 190

Glu Thr Leu Gly Phe Tyr Pro Trp Leu Pro Thr Lys Pro Thr Gln Tyr
        195                 200                 205

Arg Tyr Tyr Leu Ser Cys Thr Arg Asn Leu Asn Pro Pro Thr Tyr Thr
210                 215                 220

Gly Gln Ser Glu Gln Ile Thr Asp Ser Ile Gln Thr Gly Leu His Ser
225                 230                 235                 240

Asp Ile Met Phe Tyr Thr Ile Glu Asn Ala Val Pro Ile His Leu Leu
                245                 250                 255

Arg Thr Gly Asp Glu Phe Ser Thr Gly Ile Tyr His Phe Asp Thr Lys
            260                 265                 270

Pro Leu Lys Leu Thr His Ser Trp Gln Thr Asn Arg Ser Leu Gly Leu
        275                 280                 285

Pro Pro Lys Leu Leu Thr Glu Pro Thr Thr Glu Gly Asp Gln His Pro
290                 295                 300

Gly Thr Leu Pro Ala Ala Asn Thr Arg Lys Gly Tyr His Gln Thr Ile
305                 310                 315                 320

Asn Asn Ser Tyr Thr Glu Ala Thr Ala Ile Arg Pro Ala Gln Val Gly
                325                 330                 335

Tyr Asn Thr Pro Tyr Met Asn Phe Glu Tyr Ser Asn Gly Gly Pro Phe
            340                 345                 350

Leu Thr Pro Ile Val Pro Thr Ala Asp Thr Gln Tyr Asn Asp Asp Glu
        355                 360                 365

Pro Asn Gly Ala Ile Arg Phe Thr Met Gly Tyr Gln His Gly Gln Leu
370                 375                 380

Thr Thr Ser Ser Gln Glu Leu Glu Arg Tyr Thr Phe Asn Pro Gln Ser
385                 390                 395                 400

Lys Cys Gly Arg Ala Pro Lys Gln Gln Phe Asn Gln Ser Pro Leu
                405                 410                 415

Asn Leu Gln Asn Thr Asn Asn Gly Thr Leu Leu Pro Ser Asp Pro Ile
            420                 425                 430
```

```
Gly Gly Lys Thr Asn Met His Phe Met Ser Thr Leu Asn Thr Tyr Gly
            435                 440                 445

Pro Leu Thr Ala Leu Asn Asn Thr Ala Pro Val Phe Pro Asn Gly Gln
        450                 455                 460

Ile Trp Asp Lys Glu Leu Asp Thr Asp Leu Lys Pro Arg Leu His Val
465                 470                 475                 480

Thr Ala Pro Phe Val Cys Lys Asn Asn Pro Pro Gly Gln Leu Phe Val
                485                 490                 495

Lys Ile Ala Pro Asn Leu Thr Asp Phe Asn Ala Asp Ser Pro Gln
                500                 505                 510

Gln Pro Arg Ile Ile Thr Tyr Ser Asn Phe Trp Trp Lys Gly Thr Leu
            515                 520                 525

Thr Phe Thr Ala Lys Met Arg Ser Ser Asn Met Trp Asn Pro Ile Gln
        530                 535                 540

Gln His Thr Thr Thr Ala Glu Asn Ile Gly Asn Tyr Ile Pro Thr Asn
545                 550                 555                 560

Ile Gly Gly Ile Lys Met Phe Pro Glu Tyr Ser Gln Leu Ile Pro Arg
                565                 570                 575

Lys Leu Tyr

<210> SEQ ID NO 10
<211> LENGTH: 579
<212> TYPE: PRT
<213> ORGANISM: Porcine parvovirus

<400> SEQUENCE: 10

Met Ser Glu Asn Val Glu Gln His Asn Pro Ile Asn Ala Gly Thr Glu
1               5                   10                  15

Leu Ser Ala Thr Gly Asn Glu Ser Ile Gly Gly Gly Gly Gly Gly Gly
            20                  25                  30

Gly Arg Gly Ser Ile Gly Val Gly Val Ser Thr Gly Ser Phe Asn Asn
        35                  40                  45

Gln Thr Glu Phe Gln Tyr Leu Gly Glu Gly Leu Val Arg Ile Thr Ala
    50                  55                  60

His Ala Ser Arg Leu Ile His Leu Asn Met Pro Glu His Glu Thr Tyr
65                  70                  75                  80

Lys Arg Ile His Val Leu Asn Ser Glu Ser Gly Val Ala Gly Gln Met
                85                  90                  95

Val Gln Asp Asp Ala His Thr Gln Met Val Thr Pro Trp Ser Leu Ile
            100                 105                 110

Asp Ala Asn Ala Trp Gly Val Trp Phe Asn Pro Ala Asp Trp Gln Leu
        115                 120                 125

Ile Ser Asn Asn Met Thr Glu Ile Asn Leu Val Ser Phe Glu Gln Glu
    130                 135                 140

Ile Phe Asn Val Val Leu Lys Thr Ile Thr Glu Ser Ala Thr Ser Pro
145                 150                 155                 160

Pro Thr Lys Ile Tyr Asn Asn Asp Leu Thr Ala Ser Leu Met Val Ala
                165                 170                 175

Leu Asp Thr Asn Asn Thr Leu Pro Tyr Thr Pro Ala Ala Pro Arg Ser
            180                 185                 190

Glu Thr Leu Gly Phe Tyr Pro Trp Leu Pro Thr Lys Pro Thr Gln Tyr
        195                 200                 205

Arg Tyr Tyr Leu Ser Cys Thr Arg Asn Leu Asn Pro Pro Thr Tyr Thr
    210                 215                 220
```

```
Gly Gln Ser Glu Gln Ile Thr Asp Ser Ile Gln Thr Gly Leu His Ser
225                 230                 235                 240

Asp Ile Met Phe Tyr Thr Ile Glu Asn Ala Val Pro Ile His Leu Leu
                245                 250                 255

Arg Thr Gly Asp Glu Phe Ser Thr Gly Ile Tyr His Phe Asp Thr Lys
            260                 265                 270

Pro Leu Lys Leu Thr His Ser Trp Gln Thr Asn Arg Ser Leu Gly Leu
        275                 280                 285

Pro Pro Lys Leu Leu Thr Glu Pro Thr Thr Glu Gly Asp Gln His Pro
    290                 295                 300

Gly Thr Leu Pro Ala Ala Asn Thr Arg Lys Gly Tyr His Gln Thr Thr
305                 310                 315                 320

Asn Asn Ser Tyr Thr Glu Ala Thr Ala Ile Arg Pro Ala Gln Val Gly
                325                 330                 335

Tyr Asn Thr Pro Tyr Met Asn Phe Glu Tyr Ser Asn Gly Gly Pro Phe
            340                 345                 350

Leu Thr Pro Ile Val Pro Thr Ala Asp Thr Gln Tyr Asn Asp Asp Glu
        355                 360                 365

Pro Asn Gly Ala Ile Arg Phe Thr Met Gly Tyr Gln His Gly Gln Leu
    370                 375                 380

Thr Thr Ser Ser Gln Glu Leu Glu Arg Tyr Thr Phe Asn Pro Gln Ser
385                 390                 395                 400

Lys Cys Gly Arg Ala Pro Lys Gln Gln Phe Asn Gln Ser Pro Leu
                405                 410                 415

Asn Leu Gln Asn Thr Asn Asn Gly Thr Leu Leu Pro Ser Asp Pro Ile
            420                 425                 430

Gly Gly Lys Thr Asn Met His Phe Met Asn Thr Leu Asn Thr Tyr Gly
        435                 440                 445

Pro Leu Thr Ala Leu Asn Asn Thr Ala Pro Val Phe Pro Asn Gly Gln
    450                 455                 460

Ile Trp Asp Lys Glu Leu Asp Thr Asp Leu Lys Pro Arg Leu His Val
465                 470                 475                 480

Thr Ala Pro Phe Val Cys Lys Asn Asn Pro Pro Gly Gln Leu Phe Val
                485                 490                 495

Lys Ile Ala Pro Asn Leu Thr Asp Asp Phe Asn Ala Asp Ser Pro Gln
            500                 505                 510

Gln Pro Arg Ile Ile Thr Tyr Ser Asn Phe Trp Trp Lys Gly Thr Leu
        515                 520                 525

Thr Phe Thr Ala Lys Met Arg Ser Ser Asn Met Trp Asn Pro Ile Gln
    530                 535                 540

Gln His Thr Thr Thr Ala Glu Asn Ile Gly Asn Tyr Ile Pro Thr Asn
545                 550                 555                 560

Ile Gly Gly Ile Lys Met Phe Pro Glu Tyr Ser Gln Leu Ile Pro Arg
                565                 570                 575

Lys Leu Tyr

<210> SEQ ID NO 11
<211> LENGTH: 579
<212> TYPE: PRT
<213> ORGANISM: Porcine parvovirus

<400> SEQUENCE: 11

Met Ser Glu Asn Val Glu Gln His Asn Pro Ile Asn Ala Gly Thr Glu
1               5                   10                  15
```

```
Leu Ser Ala Thr Gly Asn Glu Ser Gly Gly Gly Gly Gly
        20                  25                  30

Gly Arg Gly Ala Gly Gly Val Gly Val Ser Thr Gly Ser Phe Asn Asn
        35                  40                  45

Gln Thr Glu Phe Gln Tyr Leu Gly Glu Gly Leu Val Arg Ile Thr Ala
50                          55                  60

His Ala Ser Arg Leu Ile His Leu Asn Met Pro Glu His Glu Thr Tyr
65                  70                  75                  80

Lys Arg Ile His Val Leu Asn Ser Glu Ser Gly Val Ala Gly Gln Met
                85                  90                  95

Val Gln Asp Asp Ala His Thr Gln Met Val Thr Pro Trp Ser Leu Ile
            100                 105                 110

Asp Ala Asn Ala Trp Gly Val Trp Phe Asn Pro Ala Asp Trp Gln Leu
        115                 120                 125

Ile Ser Asn Asn Met Thr Glu Ile Asn Leu Val Ser Phe Glu Gln Ala
130                 135                 140

Ile Phe Asn Val Val Leu Lys Thr Ile Thr Glu Ser Ala Thr Ser Pro
145                 150                 155                 160

Pro Thr Lys Ile Tyr Asn Asn Asp Leu Thr Ala Ser Leu Met Val Ala
                165                 170                 175

Leu Asp Thr Asn Asn Thr Leu Pro Tyr Thr Pro Ala Ala Pro Arg Ser
            180                 185                 190

Glu Thr Leu Gly Phe Tyr Pro Trp Leu Pro Thr Lys Pro Thr Gln Tyr
        195                 200                 205

Arg Tyr Tyr Leu Ser Cys Ile Arg Asn Leu Asn Pro Pro Thr Tyr Thr
210                 215                 220

Gly Gln Ser Glu Gln Ile Thr Asp Ser Ile Gln Thr Gly Leu His Ser
225                 230                 235                 240

Asp Ile Met Phe Tyr Thr Ile Glu Asn Ala Val Pro Ile His Leu Leu
                245                 250                 255

Arg Thr Gly Asp Glu Phe Ser Thr Gly Ile Tyr His Phe Asp Thr Lys
            260                 265                 270

Pro Leu Lys Leu Thr His Ser Trp Gln Thr Asn Arg Ser Leu Gly Leu
        275                 280                 285

Pro Pro Lys Leu Leu Thr Glu Pro Thr Thr Glu Gly Asp Gln His Pro
290                 295                 300

Gly Thr Leu Pro Ala Ala Asn Thr Arg Lys Gly Tyr His Gln Thr Thr
305                 310                 315                 320

Asn Asn Ser Tyr Thr Glu Ala Thr Ala Ile Arg Pro Ala Gln Val Gly
                325                 330                 335

Tyr Asn Thr Pro Tyr Met Asn Phe Glu Tyr Ser Asn Gly Gly Pro Phe
            340                 345                 350

Leu Thr Pro Ile Val Pro Thr Ala Asp Thr Gln Tyr Asn Asp Asp Glu
        355                 360                 365

Pro Asn Gly Ala Ile Arg Phe Thr Met Asp Tyr Gln His Gly Gln Leu
370                 375                 380

Thr Thr Ser Ser Gln Glu Leu Glu Arg Tyr Thr Phe Asn Pro Gln Ser
385                 390                 395                 400

Lys Cys Gly Arg Ala Pro Lys Gln Gln Phe Asn Gln Ser Pro Leu
                405                 410                 415

Asn Leu Gln Asn Thr Asn Asn Gly Thr Leu Leu Pro Ser Asp Pro Ile
            420                 425                 430

Gly Gly Lys Thr Asn Met His Phe Met Asn Thr Leu Asn Thr Tyr Gly
```

```
                435                 440                 445
Pro Leu Thr Ala Leu Asn Asn Thr Ala Pro Val Phe Pro Asn Gly Gln
    450                 455                 460

Ile Trp Asp Lys Glu Leu Asp Thr Asp Leu Lys Pro Arg Leu His Val
465                 470                 475                 480

Thr Ala Pro Phe Val Cys Lys Asn Asn Pro Pro Gly Gln Leu Phe Val
                485                 490                 495

Lys Ile Ala Pro Asn Leu Thr Asp Asp Phe Asn Ala Asp Ser Pro Gln
            500                 505                 510

Gln Pro Arg Ile Ile Thr Tyr Ser Asn Phe Trp Trp Lys Gly Thr Leu
        515                 520                 525

Thr Phe Thr Ala Lys Met Arg Ser Ser Asn Met Trp Asn Pro Ile Gln
    530                 535                 540

Gln His Thr Thr Thr Ala Glu Asn Ile Gly Asn Tyr Ile Pro Thr Asn
545                 550                 555                 560

Ile Gly Gly Ile Arg Met Phe Pro Glu Tyr Ser Gln Leu Ile Pro Arg
                565                 570                 575

Lys Leu Tyr

<210> SEQ ID NO 12
<211> LENGTH: 579
<212> TYPE: PRT
<213> ORGANISM: Porcine parvovirus

<400> SEQUENCE: 12

Met Ser Glu Asn Val Glu Gln His Asn Pro Ile Asn Ala Gly Thr Glu
1               5                   10                  15

Leu Ser Ala Thr Gly Asn Glu Ser Gly Gly Gly Gly Gly Gly Gly Gly
                20                  25                  30

Gly Arg Gly Ala Gly Gly Val Gly Val Ser Thr Gly Ser Phe Asn Asn
            35                  40                  45

Gln Thr Glu Phe Gln Tyr Leu Gly Glu Gly Leu Val Arg Ile Thr Ala
        50                  55                  60

His Ala Ser Arg Leu Ile His Leu Asn Met Pro Glu His Glu Thr Tyr
65                  70                  75                  80

Lys Arg Ile His Val Leu Asn Ser Glu Ser Gly Val Ala Gly Gln Met
                85                  90                  95

Val Gln Asp Asp Ala His Thr Gln Met Val Thr Pro Trp Ser Leu Ile
            100                 105                 110

Asp Ala Asn Ala Trp Gly Val Trp Phe Asn Pro Ala Asp Trp Gln Leu
        115                 120                 125

Ile Ser Asn Asn Met Thr Glu Ile Asn Leu Val Ser Phe Glu Gln Glu
    130                 135                 140

Ile Phe Asn Val Val Leu Lys Thr Ile Thr Glu Ser Ala Thr Ser Pro
145                 150                 155                 160

Pro Thr Lys Ile Tyr Asn Asn Asp Leu Thr Ala Ser Leu Met Val Ala
                165                 170                 175

Leu Asp Thr Asn Asn Thr Leu Pro Tyr Thr Pro Ala Ala Pro Arg Ser
            180                 185                 190

Glu Thr Leu Gly Phe Tyr Pro Trp Leu Pro Thr Lys Pro Thr Gln Tyr
        195                 200                 205

Arg Tyr Tyr Leu Ser Cys Thr Arg Asn Leu Asn Pro Pro Thr Tyr Thr
    210                 215                 220

Gly Gln Ser Glu Gln Ile Thr Asp Ser Ile Gln Thr Gly Leu His Ser
```

```
            225                 230                 235                 240
Asp Ile Met Phe Tyr Thr Ile Glu Asn Ala Val Pro Ile His Leu Leu
                    245                 250                 255

Arg Thr Gly Asp Glu Phe Ser Thr Gly Ile Tyr His Phe Asp Thr Lys
                260                 265                 270

Pro Leu Lys Leu Thr His Ser Trp Gln Thr Asn Arg Ser Leu Gly Leu
            275                 280                 285

Pro Pro Lys Leu Leu Thr Glu Pro Thr Thr Glu Gly Asp Gln His Pro
        290                 295                 300

Gly Thr Leu Pro Ala Ala Asn Thr Arg Lys Gly Tyr His Gln Thr Ile
305                 310                 315                 320

Asn Asn Ser Tyr Thr Glu Ala Thr Ala Ile Arg Pro Ala Gln Val Gly
                    325                 330                 335

Tyr Asn Thr Pro Tyr Met Asn Phe Glu Tyr Ser Asn Gly Gly Pro Phe
                340                 345                 350

Leu Thr Pro Ile Val Pro Thr Ala Asp Thr Gln Tyr Asn Asp Asp Glu
            355                 360                 365

Pro Asn Gly Ala Ile Arg Phe Thr Met Gly Tyr Gln His Gly Gln Leu
        370                 375                 380

Thr Thr Ser Ser Gln Glu Leu Glu Arg Tyr Thr Phe Asn Pro Gln Ser
385                 390                 395                 400

Lys Cys Gly Arg Ala Pro Lys Gln Gln Phe Asn Gln Ser Pro Leu
                    405                 410                 415

Asn Leu Gln Asn Thr Asn Asn Gly Thr Leu Leu Pro Ser Asp Pro Ile
                420                 425                 430

Gly Gly Lys Thr Asn Met His Phe Met Asn Thr Leu Asn Thr Tyr Gly
            435                 440                 445

Pro Leu Thr Ala Leu Asn Asn Thr Ala Pro Val Phe Pro Asn Gly Gln
        450                 455                 460

Ile Trp Asp Lys Glu Leu Asp Thr Asp Leu Lys Pro Arg Leu His Val
465                 470                 475                 480

Thr Ala Pro Phe Val Cys Lys Asn Asn Pro Pro Gly Gln Leu Phe Val
                    485                 490                 495

Lys Ile Ala Pro Asn Leu Thr Asp Asp Phe Asn Ala Asp Ser Pro Gln
                500                 505                 510

Gln Pro Arg Ile Ile Thr Tyr Ser Asn Phe Trp Trp Lys Gly Thr Leu
            515                 520                 525

Thr Phe Thr Ala Lys Met Arg Ser Ser Asn Met Trp Asn Pro Ile Gln
        530                 535                 540

Gln His Thr Thr Thr Ala Glu Asn Ile Gly Asn Tyr Ile Pro Thr Asn
545                 550                 555                 560

Ile Gly Gly Ile Lys Met Phe Pro Glu Tyr Ser Gln Leu Ile Pro Arg
                    565                 570                 575

Lys Leu Tyr

<210> SEQ ID NO 13
<211> LENGTH: 579
<212> TYPE: PRT
<213> ORGANISM: Porcine parvovirus

<400> SEQUENCE: 13

Met Ser Glu Asn Val Glu Gln His Asn Pro Ile Asn Ala Gly Thr Glu
1               5                   10                  15

Leu Ser Ala Thr Gly Asn Glu Ser Gly Gly Gly Gly Gly Gly Gly Gly
```

```
                    20                  25                  30
Gly Arg Gly Ala Gly Val Gly Val Ser Thr Gly Ser Phe Asn Asn
                35                  40                  45
Gln Thr Glu Phe Gln Tyr Leu Gly Glu Gly Leu Val Arg Ile Thr Ala
        50                  55                  60
His Ala Ser Arg Leu Ile His Leu Asn Met Pro Glu His Glu Thr Tyr
65                      70                  75                  80
Lys Arg Ile His Val Leu Asn Ser Glu Ser Gly Val Ala Gly Gln Met
                    85                  90                  95
Val Gln Asp Asp Ala His Thr Gln Met Val Thr Pro Trp Ser Leu Ile
            100                 105                 110
Asp Ala Asn Ala Trp Gly Val Trp Phe Asn Pro Ala Asp Trp Gln Leu
                115                 120                 125
Ile Ser Asn Asn Met Thr Glu Ile Asn Leu Val Ser Phe Glu Gln Glu
            130                 135                 140
Ile Phe Asn Val Val Leu Lys Thr Ile Thr Glu Ser Ala Thr Ser Pro
145                 150                 155                 160
Pro Thr Lys Ile Tyr Asn Asn Asp Leu Thr Ala Ser Leu Met Val Ala
                165                 170                 175
Leu Asp Thr Asn Asn Thr Leu Pro Tyr Thr Pro Ala Ala Pro Arg Ser
            180                 185                 190
Glu Thr Leu Gly Phe Tyr Pro Trp Leu Pro Thr Lys Pro Thr Gln Tyr
            195                 200                 205
Arg Tyr Tyr Leu Ser Cys Thr Arg Asn Leu Asn Pro Pro Thr Tyr Thr
    210                 215                 220
Gly Gln Ser Glu Gln Ile Thr Asp Ser Ile Gln Thr Gly Leu His Ser
225                 230                 235                 240
Asp Ile Met Phe Tyr Thr Ile Glu Asn Ala Val Pro Ile His Leu Leu
                245                 250                 255
Arg Thr Gly Asp Glu Phe Ser Thr Gly Ile Tyr His Phe Asp Thr Lys
            260                 265                 270
Pro Leu Lys Leu Thr His Ser Trp Gln Thr Asn Arg Ser Leu Gly Leu
            275                 280                 285
Pro Pro Lys Leu Leu Thr Glu Pro Thr Thr Glu Gly Asp Gln His Pro
        290                 295                 300
Gly Thr Leu Pro Ala Ala Asn Thr Arg Lys Gly Tyr His Gln Thr Ile
305                 310                 315                 320
Asn Asn Ser Tyr Thr Glu Ala Thr Ala Ile Arg Pro Ala Gln Val Gly
                325                 330                 335
Tyr Asn Thr Pro Tyr Met Asn Phe Glu Tyr Ser Asn Gly Gly Pro Phe
            340                 345                 350
Phe Ile Pro Ile Val Pro Thr Ala Asp Thr Gln Tyr Asn Asp Asp Glu
        355                 360                 365
Pro Asn Gly Gly Ile Arg Phe Thr Met Gly Tyr Gln His Gly Gln Leu
        370                 375                 380
Ile Thr Ser Ser Gln Glu Val Glu Arg Tyr Thr Phe Asn Pro Gln Arg
385                 390                 395                 400
Lys Cys Gly Arg Gly Ala Lys Gln Gln Phe Asn Gln Gln Ser Pro Leu
                405                 410                 415
Asn Ile Gln Asn Thr Asn Asn Gly Thr Ile Leu Pro Ser Asp Pro Ile
            420                 425                 430
Gly Gly Lys Thr Asn Met His Phe Met Asn Thr Pro Asn Thr Tyr Gly
            435                 440                 445
```

-continued

```
Pro Leu Thr Ala Val Asn Asn Thr Ala Pro Val Phe Pro Asn Gly Gln
    450                 455                 460

Ile Trp Asp Lys Glu Leu Asp Thr Asp Leu Lys Pro Arg Leu His Val
465                 470                 475                 480

Thr Ala Pro Phe Val Cys Lys Asn Asn Pro Pro Gly Gln Leu Phe Val
                    485                 490                 495

Lys Ile Ala Pro Asn Leu Thr Asp Asp Phe Asn Ala Asp Ser Pro Gln
                500                 505                 510

Gln Pro Arg Ile Ile Thr Tyr Ser Asn Phe Trp Trp Lys Gly Thr Leu
            515                 520                 525

Thr Phe Thr Ala Lys Met Arg Ser Ser Asn Met Trp Asn Pro Ile Gln
    530                 535                 540

Gln His Thr Thr Thr Ala Glu Asn Ile Gly Asn Tyr Ile Pro Thr Asn
545                 550                 555                 560

Ile Gly Gly Ile Lys Met Phe Pro Glu Tyr Ser Gln Leu Ile Pro Arg
                565                 570                 575

Lys Leu Tyr

<210> SEQ ID NO 14
<211> LENGTH: 579
<212> TYPE: PRT
<213> ORGANISM: Porcine parvovirus

<400> SEQUENCE: 14

Met Ser Glu Asn Val Glu Gln His Asn Pro Ile Asn Ala Gly Thr Glu
1               5                   10                  15

Leu Ser Ala Thr Gly Asn Glu Ser Gly Gly Gly Gly Gly Gly Gly Gly
                20                  25                  30

Gly Arg Gly Ala Gly Gly Val Gly Val Ser Thr Gly Ser Phe Asn Asn
            35                  40                  45

Gln Thr Glu Phe Gln Tyr Leu Gly Glu Gly Leu Val Arg Ile Thr Ala
    50                  55                  60

His Ala Ser Arg Leu Ile His Leu Asn Met Pro Glu His Glu Thr Tyr
65                  70                  75                  80

Lys Arg Ile His Val Leu Asn Ser Glu Ser Gly Val Ala Gly Gln Met
                85                  90                  95

Val Gln Asp Asp Ala His Thr Gln Met Val Thr Pro Trp Ser Leu Ile
            100                 105                 110

Asp Ala Asn Ala Trp Gly Val Trp Phe Asn Pro Ala Asp Trp Gln Leu
        115                 120                 125

Ile Ser Asn Asn Met Thr Glu Ile Asn Leu Val Ser Phe Glu Gln Ala
130                 135                 140

Ile Phe Asn Val Val Leu Lys Thr Ile Thr Glu Ser Ala Thr Ser Pro
145                 150                 155                 160

Pro Thr Lys Ile Tyr Asn Asn Asp Leu Thr Ala Ser Leu Met Val Ala
                165                 170                 175

Leu His Thr Asn Asn Thr Leu Pro Tyr Thr Pro Ala Ala Pro Arg Ser
            180                 185                 190

Glu Thr Leu Gly Phe Tyr Pro Trp Leu Pro Thr Lys Pro Thr Gln Tyr
        195                 200                 205

Arg Tyr Tyr Leu Ser Cys Ile Arg Asn Leu Asn Pro Pro Thr Tyr Thr
    210                 215                 220

Gly Gln Ser Glu Gln Ile Thr Asp Ser Ile Gln Thr Gly Leu His Ser
225                 230                 235                 240
```

```
Asp Ile Met Phe Tyr Thr Ile Glu Asn Ala Val Pro Ile His Leu Leu
                245                 250                 255

Arg Thr Gly Asp Glu Phe Ser Thr Gly Ile Tyr His Phe Asp Thr Lys
            260                 265                 270

Pro Leu Lys Leu Thr His Ser Trp Gln Thr Asn Arg Ser Leu Gly Leu
        275                 280                 285

Pro Pro Lys Leu Leu Thr Glu Pro Thr Thr Glu Gly Asp Gln His Pro
    290                 295                 300

Gly Thr Leu Pro Ala Ala Asn Thr Arg Lys Gly Tyr His Gln Thr Ile
305                 310                 315                 320

Asn Asn Ser Tyr Thr Glu Ala Thr Ala Ile Arg Pro Ala Gln Val Gly
                325                 330                 335

Tyr Asn Thr Pro Tyr Met Asn Phe Glu Tyr Ser Asn Gly Gly Pro Phe
            340                 345                 350

Leu Thr Pro Ile Val Pro Thr Ala Asp Thr Gln Tyr Asn Asp Asp Glu
        355                 360                 365

Pro Asn Gly Ala Ile Arg Phe Thr Met Asp Tyr Gln His Gly His Leu
    370                 375                 380

Thr Thr Ser Ser Gln Glu Leu Glu Arg Tyr Thr Phe Asn Pro Gln Ser
385                 390                 395                 400

Lys Cys Gly Arg Thr Pro Lys Gln Gln Phe Asn Gln Ser Pro Leu
                405                 410                 415

Asn Leu Gln Asn Thr Asn Asn Gly Thr Leu Leu Pro Ser Asp Pro Ile
            420                 425                 430

Gly Gly Lys Thr Asn Met His Phe Met Asn Thr Leu Asn Thr Tyr Gly
        435                 440                 445

Pro Leu Thr Ala Leu Asn Asn Thr Ala Pro Val Phe Pro Asn Gly Gln
    450                 455                 460

Ile Trp Asp Lys Glu Leu Asp Thr Asp Leu Lys Pro Arg Leu His Val
465                 470                 475                 480

Thr Ala Pro Phe Val Cys Lys Asn Asn Pro Pro Gly Gln Leu Phe Val
                485                 490                 495

Lys Ile Ala Pro Asn Leu Thr Asp Asp Phe Asn Ala Asp Ser Pro Gln
            500                 505                 510

Gln Pro Arg Ile Ile Thr Tyr Ser Asn Phe Trp Trp Lys Gly Thr Leu
        515                 520                 525

Thr Phe Thr Ala Lys Met Arg Ser Ser Asn Met Trp Asn Pro Ile Gln
    530                 535                 540

Gln His Thr Thr Thr Ala Glu Asn Ile Gly Lys Tyr Ile Pro Thr Asn
545                 550                 555                 560

Ile Gly Gly Ile Lys Met Phe Pro Glu Tyr Ser Gln Leu Ile Pro Arg
                565                 570                 575

Lys Leu Tyr

<210> SEQ ID NO 15
<211> LENGTH: 579
<212> TYPE: PRT
<213> ORGANISM: Porcine parvovirus

<400> SEQUENCE: 15

Met Ser Glu Asn Val Glu Gln His Asn Pro Ile Asn Ala Gly Thr Glu
1               5                   10                  15

Leu Ser Ala Thr Gly Asn Glu Ser Gly Gly Gly Gly Gly Gly Gly Gly
            20                  25                  30
```

-continued

Gly Arg Gly Ala Gly Val Gly Val Ser Thr Gly Ser Phe Asn Asn
          35                  40                  45

Gln Thr Glu Phe Gln Tyr Leu Gly Glu Gly Leu Val Arg Ile Thr Ala
 50                      55                  60

His Ala Ser Arg Leu Ile His Leu Asn Met Pro Glu His Glu Thr Tyr
 65                  70                  75                  80

Lys Arg Ile His Val Leu Asn Ser Glu Ser Val Ala Gly Gln Met
                 85                  90                  95

Val Gln Asp Asp Ala His Thr Gln Met Val Thr Pro Trp Ser Leu Ile
                100                 105                 110

Asp Ala Asn Ala Trp Gly Val Trp Phe Asn Pro Ala Asp Trp Gln Leu
                115                 120                 125

Ile Ser Asn Asn Met Thr Glu Ile Asn Leu Val Ser Phe Glu Gln Glu
    130                 135                 140

Ile Phe Asn Val Val Leu Lys Thr Ile Thr Glu Ser Ala Thr Ser Pro
145                 150                 155                 160

Pro Thr Lys Ile Tyr Asn Asn Asp Leu Thr Ala Ser Leu Met Val Ala
                    165                 170                 175

Leu Asp Thr Asn Asn Thr Leu Pro Tyr Thr Pro Ala Ala Pro Arg Ser
                180                 185                 190

Glu Thr Leu Gly Phe Tyr Pro Trp Leu Pro Thr Lys Pro Thr Gln Tyr
                195                 200                 205

Arg Tyr Tyr Leu Ser Cys Thr Arg Asn Leu Asn Pro Pro Thr Tyr Thr
        210                 215                 220

Gly Gln Ser Glu Gln Ile Thr Asp Ser Ile Gln Thr Gly Leu His Ser
225                 230                 235                 240

Asp Ile Met Phe Tyr Thr Ile Glu Asn Ala Val Pro Ile His Leu Leu
                245                 250                 255

Arg Thr Gly Asp Glu Phe Ser Thr Gly Ile Tyr His Phe Asp Thr Lys
                260                 265                 270

Pro Leu Lys Leu Thr His Ser Trp Gln Thr Asn Arg Ser Leu Gly Leu
            275                 280                 285

Pro Pro Lys Leu Leu Thr Glu Pro Thr Thr Glu Gly Asp Gln His Pro
        290                 295                 300

Gly Thr Leu Pro Ala Ala Asn Thr Arg Lys Gly Tyr His Gln Thr Ile
305                 310                 315                 320

Asn Asn Ser Tyr Thr Glu Ala Thr Ala Ile Arg Pro Ala Gln Val Gly
                325                 330                 335

Tyr Asn Thr Pro Tyr Met Asn Phe Glu Tyr Ser Asn Gly Gly Pro Phe
                340                 345                 350

Leu Thr Pro Ile Val Pro Thr Ala Asp Thr Gln Tyr Asn Asp Asp Glu
            355                 360                 365

Pro Asn Gly Ala Ile Arg Phe Thr Met Gly Tyr Gln His Gly Gln Leu
        370                 375                 380

Thr Thr Ser Ser Gln Glu Leu Glu Arg Tyr Thr Phe Asn Pro Gln Ser
385                 390                 395                 400

Lys Cys Gly Arg Ala Pro Lys Gln Gln Phe Asn Gln Gln Ser Pro Leu
                405                 410                 415

Asn Leu Gln Asn Thr Asn Asn Gly Thr Leu Leu Pro Ser Asp Pro Ile
            420                 425                 430

Gly Gly Lys Thr Asn Met His Phe Met Ser Thr Leu Asn Thr Tyr Gly
        435                 440                 445

```
Pro Leu Thr Ala Leu Asn Asn Thr Ala Pro Val Phe Pro Asn Gly Gln
            450                 455                 460

Ile Trp Asp Lys Glu Leu Asp Thr Asp Leu Lys Pro Arg Leu His Val
465                 470                 475                 480

Thr Ala Pro Phe Val Cys Lys Asn Asn Pro Pro Gly Gln Leu Phe Val
                485                 490                 495

Lys Ile Ala Pro Asn Leu Thr Asp Asp Phe Asn Ala Asp Ser Pro Gln
                500                 505                 510

Gln Pro Arg Ile Ile Thr Tyr Ser Asn Phe Trp Trp Lys Gly Thr Leu
            515                 520                 525

Thr Phe Thr Ala Lys Met Arg Ser Ser Asn Met Trp Asn Pro Ile Gln
530                 535                 540

Gln His Thr Thr Thr Ala Glu Asn Ile Gly Asn Tyr Ile Pro Thr Asn
545                 550                 555                 560

Ile Gly Gly Ile Lys Met Phe Pro Glu Tyr Ser Gln Leu Ile Pro Arg
                565                 570                 575

Lys Leu Tyr

<210> SEQ ID NO 16
<211> LENGTH: 579
<212> TYPE: PRT
<213> ORGANISM: Porcine parvovirus

<400> SEQUENCE: 16

Met Ser Glu Asn Val Glu Gln His Asn Pro Ile Asn Ala Gly Thr Glu
1               5                   10                  15

Leu Ser Ala Thr Gly Asn Glu Ser Gly Gly Gly Gly Gly Gly Gly Gly
                20                  25                  30

Gly Arg Gly Ala Gly Gly Val Gly Val Ser Thr Gly Ser Phe Asn Asn
            35                  40                  45

Gln Thr Glu Phe Gln Tyr Leu Gly Glu Gly Leu Val Arg Ile Thr Ala
    50                  55                  60

His Ala Ser Arg Leu Ile His Leu Asn Met Pro Glu His Glu Thr Tyr
65                  70                  75                  80

Lys Arg Ile His Val Leu Asn Ser Glu Ser Gly Val Ala Gly Gln Met
                85                  90                  95

Val Gln Asp Asp Ala His Thr Gln Met Val Thr Pro Trp Ser Leu Ile
            100                 105                 110

Asp Ala Asn Ala Trp Gly Val Trp Phe Asn Pro Ala Asp Trp Gln Leu
        115                 120                 125

Ile Ser Asn Asn Met Thr Glu Ile Asn Leu Val Ser Phe Glu Gln Glu
    130                 135                 140

Ile Phe Asn Val Val Leu Lys Thr Ile Thr Glu Ser Ala Thr Ser Pro
145                 150                 155                 160

Pro Thr Lys Ile Tyr Asn Asn Asp Leu Thr Ala Ser Leu Met Val Ala
                165                 170                 175

Leu Asp Thr Asn Asn Thr Leu Pro Tyr Thr Pro Ala Ala Pro Arg Ser
            180                 185                 190

Glu Thr Leu Gly Phe Tyr Pro Trp Leu Pro Thr Lys Pro Thr Gln Tyr
        195                 200                 205

Arg Tyr Tyr Leu Ser Cys Thr Arg Asn Leu Asn Pro Pro Thr Tyr Thr
    210                 215                 220

Gly Gln Ser Glu Gln Ile Thr Asp Ser Ile Gln Thr Gly Leu His Ser
225                 230                 235                 240
```

```
Asp Ile Met Phe Tyr Thr Ile Glu Asn Ala Val Pro Ile His Leu Leu
                245                 250                 255

Arg Thr Gly Asp Glu Phe Ser Thr Gly Ile Tyr His Phe Asp Thr Lys
            260                 265                 270

Pro Leu Lys Leu Thr His Ser Trp Gln Thr Asn Arg Ser Leu Gly Leu
        275                 280                 285

Pro Pro Lys Leu Leu Thr Glu Pro Thr Thr Glu Gly Asp Gln His Pro
290                 295                 300

Gly Thr Leu Pro Ala Ala Asn Thr Arg Lys Gly Tyr His Gln Thr Thr
305                 310                 315                 320

Asn Asn Ser Tyr Thr Glu Ala Thr Ala Ile Arg Pro Ala Gln Val Gly
                325                 330                 335

Tyr Asn Thr Pro Tyr Met Asn Phe Glu Tyr Ser Asn Gly Gly Pro Phe
            340                 345                 350

Leu Thr Pro Ile Val Pro Thr Ala Asp Thr Gln Tyr Asn Asp Asp Glu
        355                 360                 365

Pro Asn Gly Ala Ile Arg Phe Thr Met Gly Tyr Gln His Gly Gln Leu
370                 375                 380

Thr Thr Ser Ser Gln Glu Leu Glu Arg Tyr Thr Phe Asn Pro Gln Ser
385                 390                 395                 400

Lys Cys Gly Arg Ala Pro Lys Gln Gln Phe Asn Gln Ser Pro Leu
                405                 410                 415

Asn Leu Gln Asn Thr Asn Asn Gly Thr Leu Leu Pro Ser Asp Pro Ile
            420                 425                 430

Gly Gly Lys Thr Asn Met His Phe Met Asn Thr Leu Asn Thr Tyr Gly
        435                 440                 445

Pro Leu Thr Ala Leu Asn Asn Thr Ala Pro Val Phe Pro Asn Gly Gln
450                 455                 460

Ile Trp Asp Lys Glu Leu Asp Thr Asp Leu Lys Pro Arg Leu His Val
465                 470                 475                 480

Thr Ala Pro Phe Val Cys Lys Asn Asn Pro Pro Gly Gln Leu Phe Val
                485                 490                 495

Lys Ile Ala Pro Asn Leu Thr Asp Asp Phe Asn Ala Asp Ser Pro Gln
            500                 505                 510

Gln Pro Arg Ile Ile Thr Tyr Ser Asn Phe Trp Trp Lys Gly Thr Leu
        515                 520                 525

Thr Phe Thr Ala Lys Met Arg Ser Ser Asn Met Trp Asn Pro Ile Gln
530                 535                 540

Gln His Thr Thr Thr Ala Glu Asn Ile Gly Asn Tyr Ile Pro Thr Asn
545                 550                 555                 560

Ile Gly Gly Ile Lys Met Phe Pro Glu Tyr Ser Gln Leu Ile Pro Arg
                565                 570                 575

Lys Leu Tyr

<210> SEQ ID NO 17
<211> LENGTH: 15111
<212> TYPE: DNA
<213> ORGANISM: Porcine reproductive and respiratory syndrome virus

<400> SEQUENCE: 17
atgatgtgta gggtattccc cctacataca cgacacttct agtgtttgtg taccttggag    60
gcgtgggtac agccccgccc cacccctttgg cccctgttct agcccaacag gtatccttct   120
ctctcggggc gagtgcgccg cctgctgctc ccttgcagcg ggaaggacct cccgagtatt   180
```

```
tccggagagc acctgcttta cgggatctcc acccttttaac catgtctggg acgttctccc    240
ggtgcatgtg cacccccggct gcccgggtat tttggaacgc cggccaagtc ttttgcacac    300
ggtgtctcag tgcgcggtct cttctctctc cagagcttca ggacactgac ctcggtgcag    360
ttggcttgtt ttacaagcct agggacaagc ttcactggaa agtccctatc ggcatccctc    420
aggtggaatg tactccatcc gggtgctgtt ggctctcagc tgttttccct ttggcgcgta    480
tgacctccgg caatcacaac ttcctccaac gacttgtgaa ggttgctgat gttttgtacc    540
gtgacggttg cttggcacct cgacaccttc gtgaactcca agtttacgag cgcggctgca    600
actggtaccc gatcacgggg cccgtgcccg ggatgggttt gtttgcgaac tccatgcacg    660
tatccgacca gccgttccct ggtgccaccc atgtgttgac taactcgcct ttgcctcaac    720
aggcttgtcg gcagccgttc tgtccatttg aggaggctca ttctagcgtg tacaggtgga    780
agaaatttgt ggttttcacg gactcctccc tcaacggtcg atctcgcatg atgtggacgc    840
cggaatccga tgattcagcc gccctggagg tactaccgcc tgagttagaa cgtcaggtcg    900
aaatcctcat tcggagtttt cctgctcatc accctgtcga cctggccgac tgggagctca    960
ctgagtcccc tgagaacggt ttttccttca acacgtctca ttcttgcggt caccttgtcc   1020
agaaccccga cgtgtttgat ggcaagtgct ggctctcctg ctttttgggc cagtcggtcg   1080
aagtgcgctg ccatgaggaa catctagctg acgccttcgg ttaccaaacc aagtggggcg   1140
tgcatggtaa gtacctccag cgcaggcttc aagttcgcgg cattcgtgct gtagtcgatc   1200
ctgatggtcc cattcacgtt gaagcgctgt cttgcccccca gtcttggatc aggcacctga   1260
ctctggatga tgatgtcacc ccaggattcg ttcgcctgac atcccttcgc attgtgccga   1320
acacagagcc taccacttcc cggatctttc ggtttggagc gcataagtgg tatggcgctg   1380
ccggcaaacg ggctcgtgct aagcgtgccg ctaaaagtga aaggattcg gctcccaccc   1440 ccaaggttgc cctgccggtc cccacctgtg gaattaccac ctactctcca ccgacagacg   1500
ggtcttgtgg ttggcatgtc cttgccgcca taatgaaccg gatgataaat ggtgacttca   1560
cgtcccctct gactcagtac aacagaccag aggatgattg ggcttctgat tatgatcttg   1620
ttcaggcgat tcaatgtcta cgactgcctg ctaccgtggt tcggaatcgc gcctgtccta   1680
acgccaagta ccttataaaa cttaacggag ttcactggga ggtagaggtg aggtctggaa   1740
tggctcctcg ctcccttct cgtgaatgtg tggttggcgt ttgctctgaa ggctgtgtcg   1800
caccgcctta tccagcagac gggctaccta acgtgcact cgaggccttg gcgtctgctt   1860
acagactacc ctccgattgt gttagctctg gtattgctga cttctttgct aatccacctc   1920
ctcaggaatt ctggacccatc gacaaaatgt tgacctcccc gtcaccagag cggtccggct   1980
tctctagttt gtataaatta ctattagagg ttgttccgca aaaatgcggt gccacggaag   2040
gggctttcat ctatgctgtt gagaggatgt tgaaggattg tccgagctcc aaacaggcca   2100
tggcccttct ggcaaaaatt aaagttccat cctcaaaggc cccgtctgtg tccctggacg   2160
agtgtttccc tacggatgtt ttagccgact tcgagccagc atctcaggaa aggccccaaa   2220
gttccggcgc tgctgttgtc ctgtgttcac cggatgcaaa agagttcgag gaagcagccc   2280
cggaagaagt tcaagagagt ggccacaagg ccgtccactc tgcactcctt gccgagggtc   2340
ctaacaatga gcaggtacag gtggttgccg gtgagcaact gaagctcggc ggttgtggtt   2400
tggcagtcgg gaatgctcat gaaggtgctc tggtctcagc tggtctaatt aacctggtag   2460
gcgggaattt gtccccctca gaccccatga agaaaacat gctcaatagc cgggaagacg   2520
aaccactgga tttgtcccaa ccagcaccag cttccacaac gaccccttgtg agagagcaaa   2580
```

```
cacccgacaa cccaggttct gatgccggtg ccctccccgt caccgttcga gaatttgtcc    2640
cgacggggcc tatactctgt catgttgagc actgcggcac ggagtcgggc gacagcagtt    2700
cgcctttgga tctatctgat gcgcaaaccc tggaccagcc tttaaatcta tccctggccg    2760
cttggccagt gagggccacc gcgtctgacc ctggctgggt ccacggtagg cgcgagcctg    2820
tctttgtaaa gcctcgaaat gctttctctg atggcgattc agcccttcag ttcggggagc    2880
tttctgaatc cagctctgtc atcgagtttg accggacaaa agatgctccg gtggttgacg    2940
cccctgtcga cttgacgact tcgaacgagg ccctctctgt agtcgatcct ttcgaatttg    3000
ccgaactcaa gcgcccgcgt ttctccgcac aagccttaat tgaccgaggc ggtccacttg    3060
ccgatgtcca tgcaaaaata aagaaccggg tatatgaaca gtgcctccaa gcttgtgagc    3120
ccggtagtcg tgcaaccccca gccaccaggg agtggctcga caaatgtggg gataggtgg    3180 acatgaaaac ttggcgctgc acctcgcagt tccaagctgg tcgcattctt gcgtccctca    3240
aattcctccc tgacatgatt caagacacac cgcctcctgt tcccaggaag aaccgagcta    3300
gtgacaatgc cggcctgaag caactggtgg cacagtggga taggaaattg agtgtgaccc    3360
cccccccaaa accggtttggg ccagtgcttg accagatcgt ccctccgcct acggatatcc    3420
agcaagaaga tgtcaccccc tccgatgggc caccccatgc gccggatttt cctagtcgag    3480
tgagcacggg cggagttgg aaaggcctta tgctttccgg cacccgtctc gcggggtcta    3540
tcagccagcg ccttatgaca tgggttttg aagttttctc ccacctccca gcttttatgc    3600
tcacactttt ctcgccgcgg ggctctatgg ctccaggtga ttggttgttt gcaggtgtcg    3660
ttttacttgc tctcttgctc tgtcgttctt acccgatact cggatgcctt cccttattgg    3720
gtgtcttttc tggttctttg cggcgtgttc gtctgggtgt ttttggttct tggatggctt    3780
ttgctgtatt tttattctcg actccatcca acccagtcgg ttcttcttgt gaccacgatt    3840
cgccggagtg tcatgctgag cttttggctc ttgagcagcg ccaactttgg gaacctgtgc    3900
gcggccttgt ggtcggcccc tcaggcctct tatgtgtcat tcttggcaag ttactcggtg    3960
ggtcacgtta tctctggcat gttctcctac gtttatgcat gcttgcagat ttggcccttt    4020
ctcttgttta tgtggtgtcc cagggcgtt gtcacaagtg ttggggaaag tgtataagga    4080
cagctcctgc ggaggtggct cttaatgtat ttccttctc gcgcgccacc cgtgtctctc    4140
ttgtatcctt gtgtgatcga ttccaaacgc caaaagggg tgatcctgtg cacttggcaa    4200
cgggttggcg cgggtgctgg cgtggtgaga gccccatcca tcaaccacac caaaagccca    4260
tagcttatgc caatttggat gaaaagaaaa tgtctgccca acggtggtt gctgtcccat    4320 acgatcccag tcaggctatc aaatgcctga agttctgca ggcggggggg gccatcgtgg    4380
accagcctac acctgaggtc gttcgtgtgt ccgagatccc cttctcagcc ccatttttcc    4440
caaaagttcc agtcaaccca gattgcaggg ttgtggtaga ttcggacact tttgtggctg    4500
cggttcgctg cggttactcg acagcacaac tggttctggg ccggggcaac tttgccaagt    4560
taaatcagac ccccccagg aactctatct ccaccaaaac gactggtggg gcctcttaca    4620
cccttgctgt ggctcaagtg tctgcgtgga ctcttgttca tttcatcctc ggtctttggt    4680
tcacatcacc tcaagtgtgt ggccgaggaa ccgctgaccc atggtgttca aatccttttt    4740
catatcctac ctatggcccc ggagttgtgt gctcctctcg actttgtgtg tctgccgacg    4800
gggtcaccct gccattgttc tcagccgtgg cacaactctc cggtagagag gtggggattt    4860 ttatttttggt gctcgtctcc ttgactgctt tggcccaccg catggctctt aaggcagaca    4920
```

```
tgttagtggt cttttcggct ttttgtgctt acgcctggcc catgagctcc tggttaatct    4980
gcttctttcc tatactcttg aagtgggtta cccttcaccc tcttactatg ctttgggtgc    5040
actcattctt ggtgttttgt ctgccagcag ccggcatcct ctcactaggg ataactggcc    5100
ttctttgggc aattggccgc tttacccagg ttgccggaat tattacacct tatgacatcc    5160
accagtacac ctctgggcca cgtggtgcag ctgctgtggc cacagcccca gaaggcactt    5220
atatggccgc cgtccggaga gctgctttaa ctgggcgaac tttaatcttc accccgtctg    5280
cagttggatc ccttctcgaa ggtgctttca ggactcataa accctgcctt aacaccgtga    5340
atgttgtagg ctcttccctt ggttccggag gggttttcac cattgatggc agaagaactg    5400
tcgtcactgc tgcccatgtg ttgaacggcg acacagctag agtcaccggc gactcctaca    5460
accgcatgca cactttcaag accaatggtg attatgcctg gtcccatgct gatgactggc    5520
agggcgttgc ccctgtggtc aaggttgcga aggggtaccg cggtcgtgcc tactggcaaa    5580
catcaactgg tgtcgaaccc ggtatcattg gggaagggtt cgccttctgt tttactaact    5640
gcggcgattc ggggtcaccc gtcatctcag aatctggtga tcttattgga atccacaccg    5700
gttcaaacaa acttggttct ggtcttgtga caacccctga aggggagacc tgcaccatca    5760
aagaaaccaa gctctctgac cttttccagac attttgcagg cccaagcgtt cctcttgggg    5820
acattaaatt gagtccggcc atcatccctg atgtaacatc cattccgagt gacttggcat    5880
cgctcctagc ctccgtccct gtagtggaag gcggcctctc gaccgttcaa cttttgtgtg    5940 tcttttttcct tctctggcgc atgatgggcc atgcctggac acccattgtt gccgtgggct    6000 tcttttttgct gaatgaaatt cttccagcag ttttggtccg agccgtgttt tcttttgcac    6060
tctttgtgct tgcatgggcc acccctggt ctgcacaggt gttgatgatt agactcctca    6120
cggcatctct caaccgcaac aagctttctc tggcgttcta cgcactcggg ggtgtcgtcg    6180
gtttggcagc tgaaatcggg acttttgctg gcagattgtc tgaattgtct caagctcttt    6240
cgacatactg cttcttacct agggtccttg ctatgaccag ttgtgttccc accatcatca    6300
ttggtggact ccataccctc ggtgtgattc tgtggttatt caaataccgg tgcctccaca    6360
acatgctggt tggtgatggg agttttttcaa gcgccttctt cctacggtat tttgcagagg    6420
gtaatctcag aaaaggtgtt tcacagtcct gtggcatgaa taacgagtcc ctaacggctg    6480
ctttagcttg caagttgtca caggctgacc ttgattttt gtccagctta acgaacttca    6540
agtgctttgt atctgcttca aacatgaaaa atgctgccgg ccagtacatt gaagcagcgt    6600
atgccaaggc cctgcgccaa gagttggcct ctctagttca gattgacaaa atgaaaggag    6660
ttttgtccaa gctcgaggcc tttgctgaaa cagccacccc gtcccttgac ataggtgacg    6720
tgattgttct gctgggcaa catcctcacg gatccatcct cgatattaat gtggggactg    6780
aaaggaaaac tgtgtccgtg caagagaccc ggagcctagg cggctccaaa ttcagtgttt    6840
gtactgtcgt gtccaacaca cccgtggacg ccttgaccgg catcccactc cagacaccaa    6900
cccctctttt tgagaatggt ccgcgtcatc gcagcgagga agacgatctt aaagtcgaga    6960
ggatgaagaa acactgtgta tccctcggct tccacaacat caatggcaaa gtttactgca    7020
aaatttggga caagtctacc ggtgacacct tttacgcga tgattcccgg tacacccaag    7080
accatgcttt tcaggacagg tcagccgact acagagacag ggactatgag ggtgtgcaaa    7140 ccaccccccca acagggattt gatccaaagt ctgaaacccc tgttggcact gttgtgatcg    7200
gcggtattac gtataacagg tatctgatca aaggtaagga ggttctggtc cccaagcctg    7260
acaactgcct tgaagctgcc aagctgtccc ttgagcaagc tctcgctggg atgggccaaa    7320
```

-continued

```
cttgcgacct tacagctgcc gaggtggaaa agctaaagcg catcattagt caactccaag    7380
gtttgaccac tgaacaggct ttaaactgtt agccgccagc ggcttgaccc gctgtggccg    7440
cggcggccta gttgtgactg aaacggcggt aaaaattata aaataccaca gcagaacttt    7500
caccttaggc cctttagacc taaaagtcac ttccgaggtg gaggtaaaga aatcaactga    7560
gcagggccac gctgttgtgg caaacttatg ttccggtgtc atcttgatga gacctcaccc    7620
accgtcccttt gtcgacgttc ttctgaaacc cggacttgac acaatacccg gcattcaacc    7680
agggcatggg gccgggaata tgggcgtgga cggttctatt tgggattttg aaaccgcacc    7740
cacaaaggca gaactcgagt tatccaagca aataatccaa gcatgtgaag ttaggcgcgg    7800
ggacgccccg aacctccaac tcccttacaa gctctatcct gttaggggga atcctgagcg    7860
gcataaaggc cgccttatca ataccaggtt tggagattta ccttacaaaa ctcctcaaga    7920
caccaagtcc gcaatccacg cggcttgttg cctgcacccc aacggggccc ccgtgtctga    7980
tggtaaatcc acactaggta ccactcttca acatggtttc gagctttatg tccctactgt    8040
gccctatagt gtcatggagt accttgattc acgccctgac ccccttttta tgtgtactaa    8100
acatggcact tccaaggctg ctgcagagga cctccaaaaa tacgacctat ccacccaagg    8160
atttgtcctg cctggggtcc tacgcctagt acgcagattc atctttggcc atattggtaa    8220
ggcgccgcca ttgttcctcc catcaaccta tcccgccaag aactctatgg cagggatcaa    8280
tggccagagg ttcccaacaa aggacgttca gagcatacct gaaattgatg aaatgtgtgc    8340
ccgcgctgtc aaggagaatt ggcaaactgt gacaccttgc accctcaaga aacagtactg    8400
ttccaagccc aaaaccagga ccatcctggg caccaacaac tttattgcct tggctcacag    8460
atcggcgctc agtggtgtca cccaggcatt catgaagaag gcttggaagt ccccaattgc    8520
cttggggaaa aacaaattca aggagctgca ttgcactgtc gccggcaggt gtcttgaggc    8580
cgacttggcc tcctgtgacc gcagcacccc cgccattgta agatggtttg ttgccaacct    8640
cctgtatgaa cttgcaggat gtgaagagta cttgcctagc tatgtgctta attgctgcca    8700
tgacctcgtg gcaacacagg atggtgcctt cacaaaacgc ggtggcctgt cgtccgggga    8760
ccccgtcacc agtgtgtcca acaccgtata ttcactggta atttatgccc agcacatggt    8820
attgtcggcc ttgaaaatgg gtcatgaaat tggtcttaag ttcctcgagg aacagctcaa    8880
gttcgaggac ctccttgaaa ttcagccat gttggtatac tctgatgatc ttgtcttgta    8940
cgctgaaaga cccacatttc caattacca ctggtgggtc gagcaccttg acctgatgct    9000
gggtttcaga acgacccaa agaaaaccgt cataactgat aaacccagct tcctcggctg    9060
cagaattgag gcagggcgac agctagtccc caatcgcgac cgcatcctgg ctgctcttgc    9120
atatcacatg aaggcgcaga acgcctcaga gtattatgcg tctgctgccg caatcctgat    9180
ggattcatgt gcttgcattg accatgaccc tgagtggtat gaggacctca tctgcggtat    9240
tgcccggtgc gcccgccagg atggttatag cttcccaggt ccggcatttt tcatgtccat    9300
gtgggagaag ctgagaagtc ataatgaagg gaagaaattc gccactgcg gcatctgcga    9360
cgccaaagcc gactatgcgt ccgcctgtgg gcttgatttg tgtttgttcc attcgcactt    9420
tcatcaacac tgcccctgtca ctctgagctg cggtcaccat gccggttcaa aggaatgttc    9480
gcagtgtcag tcacctgttg gggctggcag atcccctctt gatgccgtgc taaaacaaat    9540
tccatacaaa cctcctcgta ctgtcatcat gaaggtgggt aataaaacaa cggccctcga    9600
tccggggagg taccagtccc gtcgaggtct cgttgcagtc aagaggggta ttgcaggcaa    9660
```

-continued

```
tgaagttgat ctttctgatg gggactacca agtggtgcct cttttgccga cttgcaaaga    9720
cataaacatg gtgaaggtgg cttgcaatgt actactcagc aagttcatag tagggccacc    9780
aggttccgga aagaccacct ggctactgag tcaagtccag gacgatgatg tcatttacac    9840
acccacccat cagactatgt ttgatatagt cagtgctctc aaagtttgca ggtattccat    9900
tccaggagcc tcaggactcc cttccccacc acctgccagg tccgggccgt gggttaggct    9960
tattgccagc gggcacgtcc ctggccgagt atcatacctc gatgaggctg gatattgtaa   10020
tcatctggac attcttagac tgcttttcca aacacccctt gtgtgtttgg gtgaccttca   10080
gcaacttcac cctgtcggct ttgattccta ctgttatgtg ttcgatcaga tgcctcagaa   10140
gcagctgacc actatttaca gatttggccc taacatctgc gcagccatcc agccttgtta   10200
cagggagaaa cttgaatcta aggctaggaa cactagggtg gttttttacca cccggcctgt   10260
ggcctttggt caggtgctga caccatacca taaagatcgc atcggctctg cgataaccat   10320
agattcatcc caggggggcca cctttgatat tgtgacattg catctaccat cgccaaagtc   10380
cctaaataaa tcccgagcac ttgtagccat cactcgggca agacacgggt tgttcattta   10440
tgaccctcat aaccagctcc aggagttttt caacttaacc cctgagcgca ctgattgtaa   10500
ccttgtgttc agccgtgggg atgagctggt agttctgaat gcggataatg cagtcacaac   10560
tgtagcgaag gcccttgaga caggtccatc tcgatttcga gtatcagacc cgaggtgcaa   10620
gtctctctta gccgcttgtt cggccagtct ggaagggagc tgtatgccac taccgcaagt   10680
ggcacataac ctggggtttt acttttcccc ggacagtcca acatttgcac ctctgccaaa   10740
agagttggcg ccacattggc cagtggttac ccaccagaat aatcgggcgt ggcctgatcg   10800
acttgtcgct agtatgcgcc caattgatgc ccgctacagc aagccaatgg tcggtgcagg   10860
gtatgtggtc gggccgtcca cctttcttgg tactcctggt gtggtgtcat actatctcac   10920
actatacatc aggggtgagc cccaggcctt gccagaaaca ctcgtttcaa cagggcgtat   10980
agccacagat tgtcgggagt atctcgacgc ggctgaggaa gaggcagcaa aagaactccc   11040
ccacgcattc attggcgatg tcaaaggtac cacggttggg gggtgtcatc acattacatc   11100
aaaataccta cctaggtccc tgcctaagga ctctgttgcc gtagttggag taagttcgcc   11160
cggcagggct gctaaagccg tgtgcactct caccgatgtg tacctccccg aactccggcc   11220
atatctgcaa cctgagacgg catcaaaatg ctggaaactc aaattagact tcagggacgt   11280
ccgactaatg gtctggaaag gagccaccgc ctatttccag ttggaagggc ttacatggtc   11340
ggcgctgccc gactatgcca ggtttattca gctgcccaag gatgccgttg tatacattga   11400
tccgtgtata ggaccggcaa cagccaaccg taaggtcgtg cgaaccacag actggcgggc   11460
cgacctggca gtgacaccgt atgattacgg tgcccagaac atttttgacaa cagcctggtt   11520
cgaggacctc gggccgcagt ggaagatttt ggggttgcag ccctttaggc gagcatttgg   11580
ctttgaaaac actgaggatt gggcaatcct tgcacgccgt atgaatgacg caaggacta    11640
cactgactat aactggaact gtgttcgaga acgcccacac gccatctacg ggcgtgctcg   11700
tgaccatacg tatcattttg cccctggcac agaattgcag gtagagctag gtaaaccccg   11760
gctgccgcct gggcaagtgc cgtgaattcg gggtgatgca atgggtcac tgtggagtaa    11820
aatcagccag ctgttcgtgg acgccttcac tgagttcctt gttagtgtgg ttgatattgc   11880
cattttcctt gccatactgt ttgggttcac cgtcgcagga tggttactgg tctttcttct   11940
cagagtggtt tgctccgcgc ttctccgttc gcgctctgcc attcactctc ccgaactatc   12000
gaaggtccta tgaaggcttg ttgcccaact gcagaccgga tgtcccacaa tttgcagtca   12060
```

```
agcacccatt gggtatgttt tggcacatgc gagtttccca cttgattgat gagatggtct   12120
ctcgtcgcat ttaccagacc atggaacatt caggtcaagc ggcctggaag caggtggttg   12180
gtgaggccac tctcacgaag ctgtcagggc tcgatatagt tactcatttc caacacctgg   12240
ccgcagtgga ggcggattct tgccgctttc tcagctcacg actcgtgatg ctaaaaaatc   12300
ttgccgttgg caatgtgagc ctacagtaca acaccacgtt ggaccgcgtt gagctcatct   12360
tccccacgcc aggtacgagg cccaagttga ccgatttcag acaatggctc atcagtgtgc   12420
acgcttccat tttttcctct gtggcttcat ctgttacctt gttcatagtg ctttggcttc   12480
gaattccagc tctacgctat gttttttggtt tccattggcc cacggcaaca catcattcga   12540
gctgaccatc aactacacca tatgcatgcc ctgttctacc agtcaagcgg ctcgccaaag   12600
gctcgagccc ggtcgtaaca tgtggtgcaa aatagggcat gacaggtgtg aggagcgtga   12660
ccatgatgag ttgttaatgt ccatcccgtc cgggtacgac aacctcaaac ttgagggtta   12720
ttatgcttgg ctggcttttt tgtccttttc ctacgcggcc caattccatc cggagttgtt   12780
cgggataggg aatgtgtcgc gcgtcttcgt ggacaagcga caccagttca tttgtgccga   12840
gcatgatgga cacaattcaa ccgtatctac cggacacaac atctccgcat tatatgcggc   12900
atattaccac caccaaatag acgggggcaa ttggttccat ttggaatggc tgcggccact   12960
cttttcttcc tggctggtgc tcaacatatc atggtttctg aggcgttcgc ctgtaagccc   13020
tgtttctcga cgcatctatc agatattgag accaacacga ccgcggctgc cggtttcatg   13080
gtccttcagg acatcaattg tttccgacct cacggggtct cagcagcgca agagaaaatt   13140
tccttcggaa agtcgtccca atgtcgtgaa gccgtcggta ctccccagta catcacgata   13200
acggctaacg tgaccgacga atcatacttg tacaacgcgg acctgctgat gctttctgcg   13260
tgccttttct acgcctcaga aatgagcgag aaaggcttca aagtcatctt tgggaatgtc   13320
tctggcgttg tttctgcttg tgtcaatttc acagattatg tggcccatgt gacccaacat   13380
acccagcagc atcatctggt aattgatcac attcggttgc tgcatttcct gacaccatct   13440
gcaatgaggt gggctacaac cattgcttgt ttgttcgcca ttctcttggc aatatgagat   13500
gttctcacaa attgggggcgt tcttgactc cgcactcttg cttctggtgg cttttttttgc   13560 tgtgtaccgg cttgtcctgg tcctttgccg atggcaacgg cgacagctcg ataccaat   13620 acatatataa cttgacgata tgcgagctga atgggaccga ctggttgtcc agccattttg   13680
gttgggcagt cgagaccttt gtgctttacc cggttgccac tcatatcctc tcactgggtt   13740
ttctcacaac aagccatttt tttgacgcgc tcggtctcgg cgctgtatcc actgcaggat   13800
ttgttggcgg gcggtacgta ctctgcagcg tctacggcgc ttgtgctttc gcagcgttcg   13860 tatgtttttgt catccgtgct gctaaaaatt gcatggcctg ccgctatgcc cgtacccggt   13920
ttaccaactt cattgtggac gaccggggga gagttcatcg atggaagtct ccaatagtgg   13980
tagaaaaatt gggcaaagcc gaagtcgatg gcaacctcgt caccatcaaa catgtcgtcc   14040 tcgaagggt taaagctcaa cccttgacga ggacttcggc tgagcaatgg gaggcctaga   14100 cgattttgc aacgatccta tcgccgcaca aaagctcgtg ctagccttta gcatcacata   14160
cacacctata atgatatacg cccttaaggt gtcacgcgg cgactcctgg ggctgttgca   14220
catcctaata tttctgaact gttccttac attcggatac atgacatatg tgcattttca   14280
atccaccaac cgtgtcgcac ttaccctggg ggctgttgtc gcccttctgt ggggtgttta   14340
cagcttcaca gagtcatgga agtttatcac ttccagatgc agattgtgtt gccttggccg   14400
```

-continued

```
gcgatacatt ctggccoctg cccatcacgt agaaagtgct gcaggtctcc attcaatctc    14460
agcgtctggt aaccgagcat acgctgtgag aaagcccgga ctaacatcag tgaacggcac    14520
tctagtacca ggacttcgga gcctcgtgct gggcggcaaa cgagctgtta acgaggagt    14580 ggttaacctc gtcaagtatg gccggtaaaa accagagcca aagaaaaag aaaagtacag    14640 ctccgatggg gaatggccag ccagtcaatc aactgtgcca gttgctgggt gcaatgataa    14700
agtcccagcg ccagcaacct aggggaggac aggccaaaaa gaaaaagcct gagaagccac    14760
attttcccct ggctgctgaa gatgacatcc ggcaccacct cacccagact gaacgctccc    14820
tctgcttgca atcgatccag acggctttca atcaaggcgc aggaactgcg tcgctttcat    14880
ccagcgggaa ggtcagtttt caggttgagt ttatgctgcc ggttgctcat acagtgcgcc    14940
tgattcgcgt gacttctaca tccgccagtc agggtgcaag ttaatttgac agtcaggtga    15000
atggccgcga ttggcgtgtg gcctctgagt cacctattca attagggcga tcacatgggg    15060
gtcatactta atcaggcagg aaccatgtga ccgaaattaa aaaaaaaaaa a            15111
```

```
<210> SEQ ID NO 18
<211> LENGTH: 15182
<212> TYPE: DNA
<213> ORGANISM: Porcine reproductive and respiratory syndrome virus

<400> SEQUENCE: 18
```

```
tttctccacc cctttaacca tgtctgggat acttgatcgg tgcacgtgta cccccaatgc      60
cagggtgttt atggcggagg gccaagtcta ctgcacacga tgcctcagtg cacggtctct    120
ccttcccctg aacctccaag tttctgagct cggggtgcta ggcctattct acaggcccga    180
agagccactc cggtggacgt tgccacgtgc attccccact gttgagtgct ccccgccgg     240 ggcctgctgg ctctctgcaa tctttccaat cgcacgaatg accagtggaa acctgaactt    300
ccaacaaaga atgatacggg tcgcagctga gctttacaga gccggccagc tcacccctgc    360
agtcttgaag gctctacaag tttatgaacg gggttgccgc tggtacccca ttgttggacc    420 tgccccctgga gtggccgttt acgccaattc cctacatgtg agtgataaac cttccccggg    480
agcaactcac gtgttgacca acctgccgct cccgcagaga cccaagcctg aagacttttg    540
cccctttgag tgtgctatgg ctactgtcta tgacattggt catgacgccg tcatgtatgt    600
ggccgaaagg aaaatctcct gggcccctcg tggcggggat gaagtgaaat ttgaagctgt    660
ccccggggag ttgaggttga ttgcgaaccg gctccgcacc tccttcccgc ccaccacac    720 agtggacatg tctaagttcg ccttcacagc ccctgggtgt ggtgtttcta tgcgggttga    780
acgccaacac ggctgccttc ccgctgacac tgtccctgaa ggcaactgct ggtggagctt    840
gtttgactcg cttccactgg aagttcagaa caaagaaatt cgccatgcta accaatttgg    900
ctaccagacc aagcatggtg tctctggcaa gtacctacag cggaggctgc aagttaatgg    960
tctccgagca gtaactgacc taaacggacc tatcgtcgta cagtacttct ccgttaagga   1020
gagttggatc cgccatttga aactggcggg agaacccagc tactctgggt ttgaggacct   1080
cctcagaata agggttgagc ctaacacgtc gccattggct gacaaggaag aaaaaattt    1140 ccggtttggc agtcacaagt ggtacggcgc tggaaagaga gcaagaaaag cacgctcttg   1200
tgcgactgcc acagtcgctg gccgcgcttt gtccgttcgt gaaacccggc aggccaagga   1260
gcacgaggtt gccggcgcca acaaggctga gcacctcaaa cactactccc cgcctgccga   1320
agggaattgt ggttggcatt gcatttccgc catcgccaac cggatggtga attccaaatt   1380
tgaaaccacc cttcccgaaa gagtgagacc tccagatgac tgggctactg acgaggatct   1440
```

```
tgtgaatgcc atccaaatcc tcagactccc tgcggcctta gacaggaacg gtgcttgtac    1500
tagcgccaag tacgtactta agctggaagg tgagcattgg actgtcactg tggcccctgg    1560
gatgtcccct tctttgctcc ctcttgaatg tgttcagggc tgttgtgggc acaagggcgg    1620
tcttggttcc ccagatgcag tcgaggtctc cggatttgac cctgcctgcc ttgaccggct    1680
ggctgaggtg atgcacctgc ctagcagtgc tatcccagcc gctctggccg aaatgtctgg    1740
cgattccgat cgttcggctt ctccggtcac caccgtgtgg actgtttcgc agttctttgc    1800
ccgtcacagc ggagggaatc accctgatca agtgcgctta gggaaaatta tcagcctttg    1860
tcaggtgatt gaggactgct gctgttccca gaacaaaacc aaccgggtca ccccggagga    1920
ggtcgcagca agattgacc tgtacctccg tggtgcaaca aatcttgaag aatgcttggc    1980
caggcttgag aaagcgcgcc cgccacgcgt aatcgacacc ttctttgatt gggatgttgt    2040
gctccctggg gttgaggcgg caacccagac gatcaagctg ccccaggtca accagtgtcg    2100
tgctctggtc cctgttgtga ctcaaaagtc cttggacgac aactcggtcc ccctgaccgc    2160
cttttcactg gctaactact actaccgtgc gcaaggtgac gaagttcgtc accgtgaaag    2220
actaaccgcc gtgctctcca agttggaaaa ggttgttcga gaagaatatg ggctcatgcc    2280
aaccgagcct ggtccacggc ccacactgcc acgcgggctc gacgaactca agaccagat    2340 ggaggaggac ttgctgaagc tggctaacgc ccagacgact tcggacatga tggcctgggc    2400
agtcgagcag gttgacctaa aaacttgggt caagaactac ccgcggtgga caccaccacc    2460
ccctccgcca aaagttcagc ctcgaaaaac gaagcctgtc aagagcttgc cggagagaaa    2520
gcctgtcccc gccccgcgca ggaaggttgg gtccgattgt ggcagcccgg tttcattagg    2580
cggcgatgtc tctaacagtt gggaagattt ggctgttagt agccccttg atctcccgac    2640 cccacctgag ccggcaacac cttcaagtga gctggtgatt gtgtcctcac cgcaatgcat    2700
cttcaggccg cgacaccct tgagtgagcc ggctccaatt cccgcacctc gcggaactgt    2760
gtctcgaccg gtgacaccct tgagtgagcc gatcccgtg cccgcaccgc ggcgtaagtt    2820
tcagcaggtg aaaagattga gttcggcggc ggcaatccca ccgtaccaga acgagcccct    2880
ggatttgtct gcttcctcac agactgaaca tgaggcctct cccccagcac cgccgcagag    2940
cgggggcgtt ccgggagtag aggggcatga agctgaggaa accctgagtg aaatctcgga    3000
catgtcgggt aacattaaac ctgcgtccgt gtcatcaagc agctccttgt ccagcgtgag    3060
aatcacacgc ccaaaatact cagctcaagc catcatcgac tcgggcgggc cctgcagtgg    3120
gcatctccaa gaggtaaagg aaacatgcct tagtgtcatg cgcgaggcat gtgatgcgac    3180
taagcttgat gaccctgcta cgcaggaatg gctttctcgc atgtgggatc gggtggacat    3240
gctgacttgg cgcaacacgt ctgtttacca ggcgatttgc accttagatg gcaggttaaa    3300
gttcctccca aaaatgatac tcgagacacc gccgcctat ccgtgtgagt ttgtgatgat    3360
gcctcacacg cctgcacctt ccgtaggtgc ggagagcgac cttaccattg gctcagttgc    3420
tactgaagat gttccacgca tcctcgagaa aatagaaaat gtcggcgaga tggccaacca    3480
gggacccttg gccttctccg aggataaacc ggtagatgac caacttgtca acgacccccg    3540
gatatcgtcg cggaggcctg acgagagcac atcagctccg tccgcaggca caggtggcgc    3600
cggctctttt accgatttgc cgccttcaga tggcgcggat acggacgggg gggggccgtt    3660
tcggacggca aaaagaaaag ctgaaaggct ctttgaccaa ctgagccgtc aggttttga    3720 cctcgtctcc catctcctg ttttcttctc acgccttttc taccctggcg gtggttattc    3780
```

```
tccgggtgat tggggttttg cagcttttac tctattgtgc ctcttttttat gttacagtta    3840 cccagccttt ggtattgctc ccctcttggg tgtgttttct gggtcttctc ggcgcgttcg    3900
aatgggggtt tttggctgct ggttggcttt tgctgttggt ctgttcaagc ctgtgtccga    3960
cccagtcggc gctgcttgtg agtttgactc gccagagtgt agaaacatcc ttcattcttt    4020
tgagcttctc aaaccttggg accctgttcg cagccttgtt gtgggccccg tcggtctcgg    4080
tcttgccatt cttggcaggt tactgggcgg ggcacgctgc atctggcact ttttgcttag    4140
gcttggcatt gttgcagact gtatcttggc tggagcttac gtgctttctc aaggtaggtg    4200
taaaaagtgc tggggatctt gtataagaac tgctcctaat gaggtcgctt ttaacgtgtt    4260
tcctttcaca cgtgcgacca ggtcgtcact tatcgacctg tgcgatcggt tttgtgcgcc    4320
aaaaggaatg gacccatttt ttctcgccac tgggtggcgc gggtgctggg ccggccgaag    4380
ccccattgag caaccctctg aaaaacccat cgcgtttgcc caattggatg aaaagaagat    4440
tacggctagg actgtggtcg cccagcctta tgacccaac caagccgtaa agtgcttgcg    4500
ggtattgcag gcgggtgggg cgatggtggc taaggcggtc ccaaaagtgg ttaaggtttc    4560
cgctgttcca ttccgagctc ccttctttcc cactggagtg aaagttgacc ctgattgcag    4620
ggtcgtggtt gaccctgaca cttttcactgc agctctccgg tctggctact ccaccacaaa    4680
cctcgtcctt ggtgtagggg actttgccca gctaaatgga ttaaaaatca ggcaaatttc    4740
caagccttca gggggaggcc cacatctcat ggctgccctg catgttgcct gctcgatggc    4800
tctgcacatg cttgctggga tttatgtgac tgcggtgggt tcttgcggca ccggcaccaa    4860
cgacccgtgg tgcgctaacc cgtttgccgt ccctggctac ggacctggct ctctctgtac    4920
gtccagattg tgcatttccc aacacggcct taccctgccc ttgtcagcac ttgtggcggg    4980
attcggtatt caagaaattg ccttggtcgt tttgattttt gtttccatcg gaggcatggc    5040
tcataggttg agctgtaagg ctgacatgct gtgtgttttg cttgcaattg ccagctatgt    5100
ttgggtacct cttacctggt tgctttgtgt gtttccttgc tggttgcgct gtttttctttt    5160 gcacccccct ccatcctat ggttggtgtt tttcttgatt tctgtgaata tgccttcagg    5220
aatcttggcc atggtgttgt tggttttctct ttggcttctt ggtcgttata ctaatgttgc    5280
tggccttgtc accccctacg acattcatca ttacaccagt ggccccgcg tgttgccgc    5340 cttggctacc gcaccagatg ggacctactt ggccgctgtc cgccgcgctg cgttgactgg    5400
ccgcaccatg ctgtttaccc cgtcccagct tgggtctctt cttgagggtg ccttcagaac    5460
tcgaaagccc tcactgaaca ccgtcaatgt gatcgggtcc tccatgggct ctggcggggt    5520
gtttaccatc gacgggaaag tcaagtgcgt aactgccgca catgtcctta cgggcaattc    5580
agctcgggtt tccggggtcg gcttcaatca aatgcttgac tttgacgtaa agggagattt    5640
cgctatcgct gattgcccga attggcaagg gctgcccc aagacccaat ctgcacgga    5700 tggatggact ggccgtgcct attggctaac atcctctggc gtcgaacccg gcgtcattgg    5760
aaaaggattc gccttctgct tcaccgcatg tggcgattcc gggtccccag tgatcaccga    5820
ggccggtgag cttgtcggcg ttcacacggg atcgaataaa caagggggg gcattgttac    5880 gcgcccctca ggccagtttt gtaatgtggc acccatcaag ctaagcgaat taagtgaatt    5940
ctttgctggg cctaaggtcc cgctcggtga tgtgaaggtc ggcagccaca taattaaaga    6000
cataagcgag gtgccttcag atctttgtgc cttgcttgct gccaaacctg aactggaagg    6060
aggcctctcc accgtccaac ttctttgtgt gttttttctc ctgtggagaa tgatgggaca    6120
tgcctggacg cccttggttg ctgtgagttt ctttatttg aatgaggttc tccctgccgt    6180
```

```
cctggtccgg agtgttttct cctttggaat gtttgtgcta tcctggctca cgccatggtc    6240
tgcgcaagtt ctgatgatca ggcttctgac agcagctctt aacaggaaca gatggtcact    6300 tgccttttc agcctcggtg cagtgaccgg ttttgtcgca gatcttgcgg ccactcaggg     6360
gcatccgttg caggcagtga tgaatttgag cacctatgca ttcctgcctc ggatgatggt    6420
tgtgacctca ccagtcccag tgatcacgtg tggtgtcgtg cacctacttg ccatcatttt    6480
gtacttgttt aagtaccgtg gcctgcacca tatccttgtt ggcgatggag tgttctctgc    6540
ggctttcttc ttgagatact ttgccgaggg aaagttgagg aagggtgt cgcaatcctg      6600 cggaatgaat catgagtctc tgactggtgc cctcgctatg agactcaatg acgaggactt    6660
ggatttcctt atgaaatgga ctgattttaa gtgctttgtt tctgcgtcca acatgaggaa    6720
tgcagcgggt caatttatcg aggctgccta tgctaaagca cttagagtag aactggccca    6780
gttggtacag gttgataaag ttcgaggtac tttggccaaa cttgaagctt tgctgatac    6840 cgtggctcct caactctcgc ccggtgacat tgttgtcgct ctcggccaca cgcctgttgg    6900
cagtatcttc gacctaaagg ttggtagcac caagcatacc ctccaagcca ttgagaccag    6960
agtccttgct gggtccaaaa tgaccgtggc gcgcgtcgtc gacccgaccc ccacgccccc    7020
acccgcaccc gtgcccatcc cctcccacc gaaagttctg gagaatggcc caacgcttg     7080 gggggatgag gaccgtttga ataagaagaa gaggcgcagg atggaagccc tcggcatcta    7140
tgttatgggc gggaaaaagt accagaaatt ttgggacaag aattccggtg atgtgtttta    7200
tgaggaggtc cataataaca cagatgagtg ggagtgtctc agagttggcg accctgccga    7260
ctttgaccct gagaagggaa ctctgtgtgg acatgtcacc attgaaaata aggcttacca    7320
tgtttacacc tccccatctg gtaagaagtt cttggtcccc gtcaacccag agaatggaag    7380
agttcaatgg gaagctgcaa gcttttccgt ggagcaggcc ctaggtatga tgaatgtcga    7440
cggcgaactg actgccaaag aactggagaa actgaaaaga ataattgaca aactccaggg    7500
cctgactaag gagcagtgtt taaactgcta gccgccagcg acttgacccg ctgtggtcgc    7560
ggcggcttgg ttgttactga acagcggta aaaatagtca aatttcacaa ccggaccttc     7620
accctgggac ctgtgaattt aaaagtggcc agtgaggttg agctaaaaga cgcggttgag    7680
cacaaccaac acccggttgc gagaccgatc gatggtggag ttgtgctctt gcgttccgcg    7740
gttccttcgc ttatagacgt cttgatctcc ggtgctgatg catctcccaa gttacttgcc    7800
catcacgggc cgggaaacac tgggatcgat ggcacgctct gggattttga gtccgaagcc    7860
actaaagagg aagtcgcact cagtgcgcaa ataatacagg cttgtgacat taggcgcggc    7920
gacgctcctg aaattggtct cccttacaag ctgtaccctg ttaggggtaa ccctgagcgg    7980
gtgaaaggag ttctgcagaa tacaaggttt ggagacatac cttacaaaac ccccagtgac    8040
actggaagcc cagtgcacgc ggctgcctgc cttacgccca cgccactcc ggtgactgat     8100 gggcgctccg tcttggccac gaccatgccc cccgggtttg agttatatgt accgaccata    8160
ccagcgtctg tccttgatta ccttgactct aggcctgact gccctaaaca gctgacagag    8220
cacggctgcg aagatgccgc actgaaagac ctctctaaat atgacttgtc cacccaaggc    8280
tttgttttac ctggagttct tcgccttgtg cggaaatacc tgtttgccca tgtaggtaag    8340
tgcccacccg ttcatcggcc ttctacttac cctgctaaga attctatggc tggaataaat    8400
gggaacaggt tccaaccaa ggacattcag agcgtccctg aaatcgacgt tctgtgcgca     8460
caggctgtgc gagaaaactg gcaaactgtc acccccttgta ctcttaagaa acagtattgc    8520
```

```
gggaagaaga agactaggac catactcggc accaataact tcatcgcact agcccaccga      8580
gcagtgttga gtggtgttac ccagggcttc atgaaaaagg cgtttaactc gcccatcgcc      8640
ctcggaaaga acaagtttaa ggagctacag actccggtcc tgggcaggtg ccttgaagct      8700
gatctcgcat cctgcgatcg atccacgcct gcaattgtcc gctggtttgc cgccaacctt      8760
ctttatgaac ttgcctgtgc tgaagagcat ctaccgtcgt acgtgctgaa ctgctgccac      8820
gacttactgg tcacgcagtc cggcgcagtg actaagagag gtggcctgtc gtctggcgac      8880
ccgatcacct ctgtgtctaa caccatttat agtttggtga tctatgcaca gcatatggtg      8940
cttagttact tcaaaagtgg tcaccccccat ggccttctgt tcttacaaga ccagctaaag      9000
tttgaggaca tgctcaaggt tcaaccctg atcgtctatt cggacgacct cgtgctgtat      9060
gccgagtctc ccaccatgcc aaactatcac tggtgggttg aacatctgaa tttgatgctg      9120
gggtttcaga cggacccaaa aagacagca ataacagact cgccatcatt tctaggctgt      9180
agaataataa atgggcgcca gctagtcccc aaccgtgaca ggatcctcgc ggccctcgcc      9240
tatcacatga aggcgagtaa tgtttctgaa tactatgcct cagcggctgc aatactcatg      9300
gacagctgtg cttgtttgga gtatgatcct gaatggtttg aagaacttgt agttggaata      9360
gcgcagtgcg cccgcaagga cggctacagt tttcccggca cgccgttctt catgtccatg      9420
tgggaaaaac tcaggtccaa ttatgagggg aagaagtcga gagtgtgcgg gtactgcggg      9480
gccccggccc cgtacgctac tgcctgtggc ctcgacgtct gcatttacca cacccacttc      9540
caccagcatt gtccagtcac aatctggtgt ggccatccag cgggttctgg ttcttgtagt      9600
gagtgcaaat cccctgtagg gaaaggcaca agcccttag acgaggtgct ggaacaagtc      9660
ccgtataagc ccccacggac cgttatcatg catgtggagc agggtctcac ccccttgat      9720 ccaggtagat accaaactcg ccgcggacta gtctctgtca ggcgtggaat taggggaaat      9780
gaagttgaac taccagacgg tgattatgct agcaccgcct tgctccctac ctgcaaagag      9840
atcaacatgg tcgctgtcgc ttccaatgta ctgcgcagca ggttcatcat cggcccaccc      9900
ggtgctggga aaacatactg gctccttcaa caggtccagg atggtgatgt tatttacaca      9960
ccaactcacc agaccatgct tgacatgatt agggctttgg ggacgtgccg gttcaacgtc     10020
ccggcaggca caacgctgca attccccgtc ccctcccgca ccggtccgtg ggttcgcatc     10080
ctagccggcg gttggtgtcc tggcaagaat tccttcctag atgaagcagc gtattgcaat     10140
caccttgatg ttttgaggct tcttagtaaa actacccta cctgtctagg agacttcaag     10200
caactccacc cagtgggttt tgattctcat tgctatgttt ttgacatcat gcctcaaact     10260
caactgaaga ccatctggag gtttggacag aatatctgtg atgccgttca gccagattac     10320
agggacaaac tcatgtccat ggtcaacaca cccgtgtga cctacgtgga aaaacctgtc     10380
aggtatgggc aggtcctcac ccctaccac agggaccgag aggacgacgc catcactatt     10440
gactccagtc aaggcgccac attcgatgtg gttacattgc atttgcccac taaagattca     10500
ctcaacaggc aaagagccct tgttgccatc accagggcaa gacacgctat ctttgtgtat     10560
gacccacaca ggcagctgca gggcttgttt gatcttcctg caaaaggcac acccgtcaac     10620
ctcgcagtgc accgcgacgg gcagctgatc gtgctggata aaataacaa agaatgcacg     10680 gtcgctcagg ctctaggcaa cgggggataaa tttagggcca cagataagcg tgttgtagat     10740
tctctccgcg ccatttgtgc tgatctagaa gggtcgagct ctccgctccc caaggtcgca     10800
cacaacttgg gattttattt ctcacctgat ttaacacagt tgctaaaact cccagtagaa     10860
cttgcacctc actggcccgt ggtgacaacc cagaacaatg aaaagtggcc agatcggctg     10920
```

```
gttgccagcc ttcgccctat ccataaatac agccgcgcgt gcatcggtgc cggctatatg   10980
gtgggccctt cggtgtttct aggcactcct ggggtcgtgt catactatct cacaaaattt   11040
gttaagggcg aggctcaatt gcttccggag acggttttca gcaccggccg aattgaggta   11100
gactgccggg aatatcttga tgatcgggag cgagaagttg ctgcgtccct cccacacgct   11160
ttcattggcg acgtcaaagg cactaccgtt ggaggatgtc atcatgtcac ctccagatac   11220
ctcccacgcg tccttcccaa ggaatcagtt gcggtagtcg gggtttcaag ccccggaaaa   11280
gccgcgaaag cattgtgcac actgacagat gtgtacctcc cagatcttga cgcctatctc   11340
cacccggaga cccagtccaa gtgctggaaa atgatgttgg acttcaaaga agttcgacta   11400
atggtctgga aagacaaaac agcctatttc caacttgaag gtcgctattt cacctggtat   11460
cagcttgcca gctatgcctc gtacatccgt gttcctgtca actctacggt gtacttggac   11520
ccctgcatgg gccccgccct ttgcaacagg agagtcgtcg ggtccaccca ctgggggggct   11580
gacctcgcgc tcaccccta tgattacggc gctaaaatta tcctgtctag cgcgtaccat   11640
ggtgaaatgc cccccggata caaaattctg gcgtgcgcgg agttctcgtt ggatgaccca   11700
gttaagtaca acatacctg ggggtttgaa tcggatacag cgtatctgta tgagttcacc   11760
ggaaacggtg aggactggga ggattacaat gatgcgtttc gtgcgcgcca ggaagggaaa   11820
atttataagg ccactgccac cagcttgaag ttttattttc ccccgggccc tgtcattgaa   11880
ccaactttag gcctgaattg aaatgaaatg gggtccatgc aaagccttt ttacaaaatt   11940
ggccaacttt ttgtggatgc tttcacggag ttccttggtgt ccattgttga tatcactata   12000
tttttggcca ttttgtttgg cttcaccatc gccggttggc tggtggtctt ttgcatcaga   12060
ttggtttgct ccgcgatact ccgtacgcgc tctgccattc actctgagca attacagaag   12120
atcttatgag gcctttcttt cccagtgcca agtggacatt cccacctggg gaactaaaca   12180
tcctttgggg atgctttggc accataaggt gtcaaccctg attgatgaaa tggtgtcgcg   12240
tcgaatgtac cgcatcatgg aaaaagcagg gcaggctgcc tggaaacagg tggtgagcga   12300
ggctacgctg tctcgcatta gtagtttgga tgtggtggct catttcagc atctagccgc   12360
cattgaagcc gagacctgta aatatttggc ctcccggctg cccatgctac acaacctgcg   12420
catgacaggt tcaaatgtaa ccatagtgta taatagcact ttgaatcagg tgtttgctat   12480
ttttccaacc cctggttccc ggccaaagct taatgatttt cagcaatggt taatagctgt   12540
acattcctcc atattttcct ctgttgcaac ttcttgtact ctttttgttg tgctgtggtt   12600
gcgggttcca atactacgta ctgcttttgg tttccgctgg ttaggggcaa ttttctttc   12660
gaactcacag tgaattacac ggtgtgtcca ccttgcctca cccggcaagc agccgcagag   12720
atctacgaac ccgtaggtc tctttggtgc aggatagggt atgaccgatg tgaggaggat   12780
gatcatgacg agctagggtt tatggtaccg cctggcctct ccagcgaagg ccacttgact   12840
agtgtttacg cctggttggc gttcttgtcc ttcagctaca cggcccagtt ccatcccgag   12900
atattcggga tagggaatgt gagtcgagtt tatgttgaca tcaaacatca actcatctgc   12960
gccgaacatg acgggcagaa caccaccttg cctcgtcatg acaacatttc agccgtgttt   13020
cagacctatt accaacatca agtcgacggc ggcaattggt ttcacctaga atggcttcgt   13080
cccttctttt cctcgtggtt ggttttaaat gtctcttggt ttctcaggcg ttcgcctgca   13140
aaccatgttt cagttcgagt cttgcagata ttaagaccaa caccaccgca gcggcaagct   13200
ttgctgtcct ccaagacatc agttgcctta ggcatcgcga ctcggcctct gaggcgattc   13260
```

-continued

```
gcaaatccc tcagtgccgt acggcgatag ggacacccgt gtatgttacc atcacagcca      13320
atgtgacaga tgagaattat ttacattctt ctgatctcct catgctttct tcttgccttt     13380
tctatgcttc tgagatgagt gaaaagggat ttaaggtggt atttggcaat gtgtcaggca     13440
tcgtggctgt gtgtgtcaat tttaccagct acgtccaaca tgtcaaggag tttacccaac     13500
gctccctggt ggtcgaccat gtgcggttgc tccatttcat gacacctgag accatgaggt     13560
gggcaactgt tttagcctgt cttttttgcca ttctgttggc aatttgaatg tttaagtatg    13620
ttggagaaat gcttgaccgc gggctgttac tcgcaattgc tttctttgtg gtgtatcgtg     13680
ccgttctgtt ttgctgtgct cgtcaacgcc agcaacgaca gcagctccca tctacagctg     13740
atttacaact tgacgctatg tgagctgaat ggcacagatt ggctagctaa caaatttgat     13800
tgggcagtgg agagttttgt catctttccc gttttgactc acattgtctc ctatggtgcc     13860
ctcactacta gccatttcct tgacacagtc gctttagtca ctgtgtctac cgccgggttt    13920
gttcacgggc ggtatgtcct aagtagcatc tacgcggtct gtgccctggc tgcgttgact    13980
tgcttcgtca ttaggtttgc aaagaattgc atgtcctggc gctacgcgtg taccagatat    14040
accaactttc ttctggacac taagggcaga ctctatcgtt ggcggtcgcc tgtcatcata    14100
gagaaaaggg gcaaagttga ggtcgaaggt catctgatcg acctcaaaag agttgtgctt    14160
gatggttccg tggcaacccc tataaccaga gtttcagcgg aacaatgggg tcgtccttag    14220
atgacttctg tcatgatagc acggctccac aaaaggtgct tttggcgttt tctattacct    14280
acacgccagt gatgatatat gccctaaagg tgagtcgcgg ccgactgcta gggcttctgc    14340
accttttgat cttcctgaat tgtgctttca ccttcgggta catgactttc gcgcactttc    14400
agagtacaaa taaggtcgcg ctcactatgg gagcagtagt tgcactcctt tgggggtgt     14460
actcagccat agaaacctgg aaattcatca cctccagatg ccgtttgtgc ttgctaggcc    14520
gcaagtacat tctggcccct gcccaccacg ttgaaagtgc cgcaggcttt catccgattg    14580
cggcaaatga taaccacgca tttgtcgtcc ggcgtcccgg ctccactacg gtcaacggca    14640
cattggtgcc cgggttaaaa agcctcgtgt tgggtggcag aaaagctgtt aaacagggag    14700
tggtaaacct tgtcaaatat gccaaataac aacggcaagc agcagaatag aaagaagggg    14760
gatggccagc cagtcaatca gctgtgccag atgctgggta agatcatcgc tcagcaaaac    14820
cagtccagag gcaagggacc gggaaagaaa aataagaaga aaaacccgga gaagccccat    14880
tttcctctag cgactgaaga tgatgtcaga catcacttta cccctagtga gcggcaattg    14940
tgtctgtcgt caatccagac cgcctttaat caaggcgctg ggacttgcac cctgtcagat    15000
tcagggagga taagttacac tgtggagttt agtttgccta cgcatcatac tgtgcgcctg    15060
attcgcgtca cagcatcacc ctcagcatga tgggctggca ttcttgaggc atctcagtgt    15120
ttgaattgga agaatgtgtg gtgaatggca ctgattgaca ttgtgcctct aagcactata    15180
tt                                                                    15182
```